US012545713B2

(12) United States Patent
Jin et al.

(10) Patent No.: US 12,545,713 B2
(45) Date of Patent: Feb. 10, 2026

(54) MODIFIED IMMUNOGLOBULIN Fc-FUSION PROTEIN AND USE THEREOF

(71) Applicant: PROGEN CO., LTD., Seoul (KR)

(72) Inventors: Hyun-Tak Jin, Seongnam-si (KR); Eun Joo Nam, Seoul (KR); Je-In Youn, Seoul (KR)

(73) Assignee: PROGEN CO., LTD., Seoul (KR)

( * ) Notice: Subject to any disclaimer, the term of this patent is extended or adjusted under 35 U.S.C. 154(b) by 1123 days.

(21) Appl. No.: 17/611,318

(22) PCT Filed: May 14, 2020

(86) PCT No.: PCT/KR2020/006346
§ 371 (c)(1),
(2) Date: Nov. 15, 2021

(87) PCT Pub. No.: WO2020/231199
PCT Pub. Date: Nov. 19, 2020

(65) Prior Publication Data

US 2023/0174617 A1 Jun. 8, 2023

Related U.S. Application Data

(60) Provisional application No. 62/847,470, filed on May 14, 2019.

(51) Int. Cl.
*C07K 14/705* (2006.01)
*C07K 14/735* (2006.01)
*C12N 15/63* (2006.01)

(52) U.S. Cl.
CPC ........ *C07K 14/70535* (2013.01); *C12N 15/63* (2013.01); *C07K 2319/30* (2013.01)

(58) Field of Classification Search
CPC .......... C07K 14/70535; C07K 2317/52; C07K 2317/94
See application file for complete search history.

(56) References Cited

U.S. PATENT DOCUMENTS

| | | | |
|---|---|---|---|
| 5,447,851 A | 9/1995 | Beutler et al. | |
| 8,883,134 B2 | 11/2014 | Cho et al. | |
| 10,208,099 B2 | 2/2019 | Yang et al. | |
| 2006/0074225 A1 | 4/2006 | Chamberlain et al. | |
| 2011/0091416 A1* | 4/2011 | Yang | A61P 37/06 514/7.7 |
| 2014/0356381 A1 | 12/2014 | Moore et al. | |

FOREIGN PATENT DOCUMENTS

| | | |
|---|---|---|
| CN | 104080811 | 9/2019 |
| EP | 2635607 | 9/2013 |
| EP | 3995508 | 5/2022 |
| JP | S52-026844 | 2/1977 |
| JP | 2006-512087 | 4/2006 |
| JP | 2007-531707 | 11/2007 |
| JP | 2008-500585 | 1/2008 |
| JP | 2009-105396 | 5/2009 |
| JP | 2010-531134 | 9/2010 |
| JP | 2018-138022 | 9/2018 |
| KR | 10-2008-0095141 | 10/2008 |
| KR | 10-0897938 | 5/2009 |
| KR | 10-2016-0083810 | 7/2016 |
| KR | 10-2018-0119135 | 11/2018 |
| RU | 2 530 168 | 10/2014 |
| WO | 2004/035752 | 4/2004 |
| WO | 2004-092219 | 10/2004 |
| WO | 2008-147143 | 12/2008 |
| WO | 2011/125370 | 10/2011 |
| WO | 2018-185043 | 10/2018 |
| WO | 2018-199595 | 11/2018 |
| WO | 2019-182425 | 9/2019 |
| WO | 2020-231199 | 11/2020 |

OTHER PUBLICATIONS

Datta-Mannan, Amita, et al. "Influence of improved FcRn binding on the subcutaneous bioavailability of monoclonal antibodies in cynomolgus monkeys." mAbs, 4:2, pp. 267-273, DOI: 10.4161/mabs.4.2.19364. (Mar. 1, 2012).
Capon et al., "Designing CD4 immunoadhesins for AIDS therapy", Nature 337: 525-531, Feb. 9, 1989.
Pierre Bruhns et al., "Specificity and affinity of human Fc receptors and their polymorphic variants for human IgG subclasses", Blood 113(16): 3716-3725, 2009.
Kathryn L. Armour et al., "Recombinant human IgG molecules lacking Fcgamma receptor I binding and monocyte triggering activities", Immunol., 29(8): 2613-2624, 1999.
Robert L. Shields et al., "High resolution mapping of the binding site on human IgG1 for Fc gamma RI, Fc gamma RII, Fc gamma RIII, and FcRn and design of IgG1 variants with improved binding to the Fc gamma R", J. Biol. Chem. 276 (9): 6591-6604, 2001.
Esohe E. Idusogie et al., "Mapping of the C1q Binding Site on Rituxan, a Chimeric Antibody with a Human IgG1 Fc", J. Immunol. 164(8): 4178-4184, 2000.
Tilman Schlothauer et al., "Novel human IgG1 and IgG4 Fc-engineered antibodies with completely abolished immune 6 effector functions", Protein Engineering, Design & Selection, 2016, pp. 1-10, doi: 10.1093/protein/gzw040.
Amita Datta-Mannan et al., "Influence of improved FcRin binding on the subcutaneous bioavailability of monoclonal antibodies in cynomolgus monkeys", mAbs. vol. 4. No. 2. 267-273, Taylor & Francis, Mar. 2012.

(Continued)

*Primary Examiner* — Aurora M Fontainhas
*Assistant Examiner* — Jennifer A Benavides
(74) *Attorney, Agent, or Firm* — LEX IP MEISTER, PLLC

(57) ABSTRACT

The present invention relates to a novel immunoglobulin Fc domain variant protein and use thereof, and when expressed in the form of a fusion protein with another biologically active protein, an immunoglobulin Fc domain variant protein according to an embodiment of the present invention can prolong the half-life in vivo of the biologically active protein as well as effectively suppress effector functions such as ADCC or CDC to minimize unexpected side effects.

11 Claims, 33 Drawing Sheets

Specification includes a Sequence Listing.

(56) References Cited

OTHER PUBLICATIONS

Muller, Sylviane, et al. "Spliceosomal peptide P140 for immunotherapy of systemic lupus erythematosus: results of an early phase II clinical trial." Arthritis & Rheumatism: Official Journal of the American College of Rheumatology 58.12 (May 13, 2008): 3873-3883.
El-Amine, Moustapha, et al. "In vivo induction of tolerance by an Ig peptide is not affected by the deletion of FcR or a mutated IgG Fc fragment." International immunology 14.7 (Jul. 1, 2002): 761-766.
Jonnalagadda, Mahesh, et al. "Chimeric antigen receptors with mutated IgG4 Fc spacer avoid fc receptor binding and improve T cell persistence and antitumor efficacy." Molecular Therapy 23.4 (Feb. 17, 2015): 757-768.
An, Zhiqiang, et al. "IgG2m4, an engineered antibody isotype with reduced Fc function." mAbs. vol. 1. No. 6. Landes Bioscience (Nov. 1, 2009):572-579.
Brinkmann, Ulrich, and Roland E. Kontermann. "The making of bispecific antibodies." MAbs. vol. 9. No. 2. Taylor & Francis, (Jan. 10, 2017):182-212.
Amita Datta-Mannan et al., "FcRn Affinity-Pharmacokinetic Relationship of Five Human IgG4 Antibodies Engineered for Improved In Vitro FcRn Binding Properties in Cynomolgus Monkeys", Drug Metabolism and Disposition, vol. 40, Issue 8, Aug. 2012, pp. 1545-1555.

* cited by examiner

Column : TSK-GEL G3000SWxL (7.8 * 300 mm)
Mobile phase : 50mM Na-Pi, 300mM NaCl, 10% ACN pH 7.0
Flow rate : 0.5 ml/min
Running time : 40 min
Injection Volume 1mg/ml, 20uL

| | RT | Area | % Area | Height |
|---|---|---|---|---|
| 1 | 16.660 | 1009679 | 1.65 | 14209 |
| 2 | 18.376 | 59999347 | 98.35 | 1534356 |

| Lane | Sample name |
|---|---|
| M | Size Marker |
| 1 | PG 22 NR |
| 2 | PG 22 R |

BIO-RAD 4-15% TGX™ gel
200 V, 30 min running, 1X TGS buffer

Column : TSK-GEL G3000SWxL (7.8 * 300 mm)
Mobile phase : 50 mM NaPi, 300 mM NaCl, 20% ACN pH 7.0
Flow rate : 0.5 mL/min
Running time : 30 min
Injection Volume: 1mg/mL, 20 uL

| | RT | Area | % Area | Height |
|---|---|---|---|---|
| 1 | 9.926 | 1178442 | 4.65 | 19816 |
| 2 | 11.288 | 24163774 | 95.35 | 826305 |

| Lane | Sample name |
|---|---|
| M | Size Marker |
| 1 | PG 088 NR |
| 2 | PG 088 R |

BIO-RAD 4-15% TGX™ gel
200 V, 30 min running, 1X TGS buffer

Column : TSK-GEL G3000SWxL (7.8 * 300 mm)
Mobile phase : 50 mM NaPi, 300 mM NaCl, 10% ACN pH 7.0
Flow rate : 0.5 mL/min
Running time : 40 min
Injection Volume: 1mg/mL, 20 uL

| | RT | Area | % Area | Height |
|---|---|---|---|---|
| 1 | 12.117 | 112879 | 0.34 | 2169 |
| 2 | 17.709 | 32877027 | 98.72 | 924034 |
| 3 | 21.888 | 313720 | 0.94 | 5985 |

| Lane | Sample name |
|---|---|
| M | Size Marker |
| 1 | NTIG-IL10vm NR |
| 2 | NTIG-IL10vm R |

Bio-rad 4-15% TGX gel
200 V, 30 min running, 1X TGX buffer

Column : TSK-GEL G3000SWxL (7.8 * 300 mm)
Mobile phase : 50 mM NaPi, 300 mM NaCl, 10% ACN pH 7.0
Flow rate : 0.5 mL/min
Running time : 30 min
Injection Volume: 1mg/mL, 20 uL

| | RT | Area | % Area | Height |
|---|---|---|---|---|
| 1 | 14.034 | 316694 | 0.94 | 8250 |
| 2 | 16.261 | 33517509 | 99.06 | 1039166 |

| Lane | Sample name | Loading amount |
|---|---|---|
| M | Size Marker | 3ul |
| 1 | PG 075 NR | 3ug |
| M | Size Marker | 3ul |
| 2 | PG 075 R | 3ug |

BIO-RAD 4-15% TGX™ gel
200 V, 30 min running, 1X TGS buffer

| Lane | Loading sample | |
|---|---|---|
| 1 | PG-075 (100ng) | Non-Reducing |
| 2 | | |
| 3 | PG-075 (400ng) | Reducing |
| 4 | | |

| 시험조건 | |
|---|---|
| Gel | 3-8 Tris-Acetate |
| Loading condition | 150V 60min |
| Size maker | HiMark™ Pre-Stained Protein Standard |

Primary: Antibody IgG (1:10000)
Secondary: Mouse Alkaline Phosphatase IgG4 (1:10000)

| Lane | Sample name |
|---|---|
| M | Size Marker |
| 1 | PG 110-1 (NR) |
| 2 | PG 110-1 (R) |

Bio-rad 4-15% TGX gel
200 V, 35 min running, 1X TGX buffer

Column : TSK-GEL G3000SWxL (7.8 * 300 mm)
Mobile phase : 50 mM NaPi, 300 mM NaCl, 10% ACN pH 7.0
Flow rate : 0.5 mL/min
Running time : 40 min
Injection Volume: 1mg/mL, 20 uL

| | RT | Area | % Area | Height |
|---|---|---|---|---|
| 1 | 11.987 | 2200058 | 4.45 | 41513 |
| 2 | 13.970 | 46969173 | 94.98 | 1234691 |
| 3 | 16.117 | 284189 | 0.57 | 2440 |

| Lane | Sample name |
|---|---|
| M | Size Marker |
| 1 | PG 129 NR |
| 2 | PG 129 R |

Column : TSK-GEL G3000SWxL (7.8 * 300 mm)
Mobile phase : 50mM Na-Pi, 300mM NaCl, 10% ACN pH 7.0
Flow rate : 0.5 ml/min
Running time : 40 min
Injection Volume 1mg/ml, 20uL

| | RT | Area | % Area | Height |
|---|---|---|---|---|
| 1 | 13.910 | 1045557 | 2.10 | 17926 |
| 2 | 16.691 | 48811510 | 97.90 | 1517214 |

| Lane | Sample name |
|---|---|
| M | Size Marker |
| 1 | PG-400 |
| 2 | Control(Herceptin) |

| Integration Results | | | | | | | |
|---|---|---|---|---|---|---|---|
| No. | Peak Name | Retention Time min | Area mAU*min | Height mAU | Relative Area % | Relative Height % | Amount n.a. |
| 1 | | 8.328 | 27.572 | 89.932 | 99.45 | 99.48 | n.a. |
| 2 | | 9.449 | 0.153 | 0.475 | 0.55 | 0.52 | n.a. |
| **Total:** | | | **27.725** | **90.407** | **100.00** | **100.00** | |

| | |
|---|---|
| Column | SRT-C SEC300, 5 um, 7.8 mm x 300 mm (Sepax, 235300-7830) |
| Instrument: | Ultimate3000 (Thermo) |
| Mobile phase | PBS, pH 7.4 |
| Flow rate | 1 mL/min |
| Injection | 20 ug |

| Lane | Sample name |
|---|---|
| M | Size Marker |
| 1 | PG-410 |
| 2 | Control(Herceptin) |

| | |
|---|---|
| Instrument | Ultimate 3000 (Thermo) |
| Column | SRT-C SEC 300, 7.8 x 300 mm<br>U 5um, 300 Å (Sepax) |
| Flow rate | 1 mL/min |
| Detection | 280 nm |
| Injection | 20 ug |
| Mobile phase | D-PBS, pH 7.4 |
| Elution | isocratic elution |
| Run time | 20 min |

| Lane | Protein (loading amount) |
|---|---|
| M | Size marker (3 ~ 10 uL) |
| 4 | MG12-4 (3 ug) |
| 5 | MG12-5 (3 ug) |

| Lane | Sample name | Loading amount |
|---|---|---|
| M | Size Marker | 3ul |
| 1 | Input | Max |
| 2 | FT | Max |
| 3 | Elute | 3 ug |
| 4 | Elute_N | 3 ug |
| M | Size Marker | 3ul |
| 5 | Input | Max |
| 6 | FT | Max |
| 7 | Elute | 3 ug |
| 8 | Elute_N | 3 ug |

| PG 050-1 | Purity (%) |
|---|---|
| #1 | 7.5 |
| #2 | 75.5 |
| #3 | 10.9 |
| #4 | 3.9 |
| #5 | 2.2 |

| Lane | Sample name | Loading amount |
|---|---|---|
| M | Size Marker | 3ul |
| 1 | Input | Max |
| 2 | FT | Max |
| 3 | Elute | 3 ug |
| 4 | Elute_N | 3 ug |
| M | Size Marker | 3ul |
| 5 | Input | Max |
| 6 | FT | Max |
| 7 | Elute | 3 ug |
| 8 | Elute_N | 3 ug |

| PG 050-2 | Purity (%) |
|---|---|
| #1 | 2.6 |
| #2 | 2.7 |
| #3 | 90.7 |
| #4 | 4.0 |

| | RT | Area | % Area | Height |
|---|---|---|---|---|
| 1 | 12.093 | 749726 | 5.80 | 13604 |
| 2 | 14.333 | 764561 | 5.91 | 7697 |
| 3 | 16.077 | 11412013 | 88.29 | 264387 |

| | RT | Area | % Area | Height |
|---|---|---|---|---|
| 1 | 12.115 | 291681 | 4.24 | 4463 |
| 2 | 14.098 | 342404 | 4.98 | 4184 |
| 3 | 15.930 | 6243681 | 90.78 | 156860 |

| Preconditioning | Association | Dissociation |
|---|---|---|
| pH 7.3 | pH 6.0 | pH 7.3 |
| 120 s | 180 s | 180 s |

| Preconditioning | Association | Dissociation |
|---|---|---|
| pH 7.3 | pH 6.0 | pH 7.3 |
| 120 s | 180 s | 180 s |

SEQUENCE LISTING

```
<160> NUMBER OF SEQ ID NOS: 77

<210> SEQ ID NO 1
<211> LENGTH: 214
<212> TYPE: PRT
<213> ORGANISM: Artificial Sequence
<220> FEATURE:
<223> OTHER INFORMATION: modified IgG4 Fc C-term lysine deleted

<400> SEQUENCE: 1

Ser His Thr Gln Pro Leu Gly Val Phe Leu Phe Pro Pro Lys Pro Lys
1               5                   10                  15

Asp Thr Leu Met Ile Ser Arg Thr Pro Glu Val Thr Cys Val Val Val
            20                  25                  30

Asp Val Ser Gln Glu Asp Pro Glu Val Gln Phe Asn Trp Tyr Val Asp
        35                  40                  45

Gly Val Glu Val His Asn Ala Lys Thr Lys Pro Arg Glu Glu Gln Phe
```

```
    50                  55                  60

Asn Ser Thr Tyr Arg Val Val Ser Val Leu Thr Val Leu His Gln Asp
65                  70                  75                  80

Trp Leu Asn Gly Lys Glu Tyr Lys Cys Lys Val Ser Asn Lys Gly Leu
                85                  90                  95

Pro Ser Ser Ile Glu Lys Thr Ile Ser Lys Ala Lys Gly Gln Pro Arg
            100                 105                 110

Glu Pro Gln Val Tyr Thr Leu Pro Pro Ser Gln Glu Glu Met Thr Lys
        115                 120                 125

Asn Gln Val Ser Leu Thr Cys Leu Val Lys Gly Phe Tyr Pro Ser Asp
    130                 135                 140

Ile Ala Val Glu Trp Glu Ser Asn Gly Gln Pro Glu Asn Asn Tyr Lys
145                 150                 155                 160

Thr Thr Pro Pro Val Leu Asp Ser Asp Gly Ser Phe Phe Leu Tyr Ser
                165                 170                 175

Arg Leu Thr Val Asp Lys Ser Arg Trp Gln Glu Gly Asn Val Phe Ser
            180                 185                 190

Cys Ser Val Met His Glu Ala Leu His Asn His Tyr Thr Gln Lys Ser
        195                 200                 205

Leu Ser Leu Ser Leu Gly
    210


<210> SEQ ID NO 2
<211> LENGTH: 215
<212> TYPE: PRT
<213> ORGANISM: Artificial Sequence
<220> FEATURE:
<223> OTHER INFORMATION: modified IgG4 Fc

<400> SEQUENCE: 2

Ser His Thr Gln Pro Leu Gly Val Phe Leu Phe Pro Pro Lys Pro Lys
1               5                   10                  15

Asp Thr Leu Met Ile Ser Arg Thr Pro Glu Val Thr Cys Val Val Val
            20                  25                  30

Asp Val Ser Gln Glu Asp Pro Glu Val Gln Phe Asn Trp Tyr Val Asp
        35                  40                  45

Gly Val Glu Val His Asn Ala Lys Thr Lys Pro Arg Glu Glu Gln Phe
    50                  55                  60

Asn Ser Thr Tyr Arg Val Val Ser Val Leu Thr Val Leu His Gln Asp
65                  70                  75                  80

Trp Leu Asn Gly Lys Glu Tyr Lys Cys Lys Val Ser Asn Lys Gly Leu
                85                  90                  95

Pro Ser Ser Ile Glu Lys Thr Ile Ser Lys Ala Lys Gly Gln Pro Arg
            100                 105                 110

Glu Pro Gln Val Tyr Thr Leu Pro Pro Ser Gln Glu Glu Met Thr Lys
        115                 120                 125

Asn Gln Val Ser Leu Thr Cys Leu Val Lys Gly Phe Tyr Pro Ser Asp
    130                 135                 140

Ile Ala Val Glu Trp Glu Ser Asn Gly Gln Pro Glu Asn Asn Tyr Lys
145                 150                 155                 160

Thr Thr Pro Pro Val Leu Asp Ser Asp Gly Ser Phe Phe Leu Tyr Ser
                165                 170                 175

Arg Leu Thr Val Asp Lys Ser Arg Trp Gln Glu Gly Asn Val Phe Ser
            180                 185                 190

Cys Ser Val Met His Glu Ala Leu His Asn His Tyr Thr Gln Lys Ser
```

```
        195                 200                 205

Leu Ser Leu Ser Leu Gly Lys
    210                 215


<210> SEQ ID NO 3
<211> LENGTH: 215
<212> TYPE: PRT
<213> ORGANISM: Artificial Sequence
<220> FEATURE:
<223> OTHER INFORMATION: modified IgG4 Fc Knob

<400> SEQUENCE: 3

Ser His Thr Gln Pro Leu Gly Val Phe Leu Phe Pro Pro Lys Pro Lys
1               5                   10                  15

Asp Thr Leu Met Ile Ser Arg Thr Pro Glu Val Thr Cys Val Val Val
            20                  25                  30

Asp Val Ser Gln Glu Asp Pro Glu Val Gln Phe Asn Trp Tyr Val Asp
        35                  40                  45

Gly Val Glu Val His Asn Ala Lys Thr Lys Pro Arg Glu Glu Gln Phe
    50                  55                  60

Asn Ser Thr Tyr Arg Val Val Ser Val Leu Thr Val Leu His Gln Asp
65                  70                  75                  80

Trp Leu Asn Gly Lys Glu Tyr Lys Cys Lys Val Ser Asn Lys Gly Leu
                85                  90                  95

Pro Ser Ser Ile Glu Lys Thr Ile Ser Lys Ala Lys Gly Gln Pro Arg
            100                 105                 110

Glu Pro Gln Val Tyr Thr Leu Pro Pro Cys Gln Glu Glu Met Thr Lys
        115                 120                 125

Asn Gln Val Ser Leu Trp Cys Leu Val Lys Gly Phe Tyr Pro Ser Asp
    130                 135                 140

Ile Ala Val Glu Trp Glu Ser Asn Gly Gln Pro Glu Asn Asn Tyr Lys
145                 150                 155                 160

Thr Thr Pro Pro Val Leu Asp Ser Asp Gly Ser Phe Phe Leu Tyr Ser
                165                 170                 175

Arg Leu Thr Val Asp Lys Ser Arg Trp Gln Glu Gly Asn Val Phe Ser
            180                 185                 190

Cys Ser Val Met His Glu Ala Leu His Asn His Tyr Thr Gln Lys Ser
        195                 200                 205

Leu Ser Leu Ser Leu Gly Lys
    210                 215


<210> SEQ ID NO 4
<211> LENGTH: 215
<212> TYPE: PRT
<213> ORGANISM: Artificial Sequence
<220> FEATURE:
<223> OTHER INFORMATION: modified IgG4 Fc Hole

<400> SEQUENCE: 4

Ser His Thr Gln Pro Leu Gly Val Phe Leu Phe Pro Pro Lys Pro Lys
1               5                   10                  15

Asp Thr Leu Met Ile Ser Arg Thr Pro Glu Val Thr Cys Val Val Val
            20                  25                  30

Asp Val Ser Gln Glu Asp Pro Glu Val Gln Phe Asn Trp Tyr Val Asp
        35                  40                  45

Gly Val Glu Val His Asn Ala Lys Thr Lys Pro Arg Glu Glu Gln Phe
    50                  55                  60
```

```
Asn Ser Thr Tyr Arg Val Val Ser Val Leu Thr Val Leu His Gln Asp
65                  70                  75                  80

Trp Leu Asn Gly Lys Glu Tyr Lys Cys Lys Val Ser Asn Lys Gly Leu
                85                  90                  95

Pro Ser Ser Ile Glu Lys Thr Ile Ser Lys Ala Lys Gly Gln Pro Arg
            100                 105                 110

Glu Pro Gln Val Cys Thr Leu Pro Pro Ser Gln Glu Glu Met Thr Lys
        115                 120                 125

Asn Gln Val Ser Leu Ser Cys Ala Val Lys Gly Phe Tyr Pro Ser Asp
    130                 135                 140

Ile Ala Val Glu Trp Glu Ser Asn Gly Gln Pro Glu Asn Asn Tyr Lys
145                 150                 155                 160

Thr Thr Pro Pro Val Leu Asp Ser Asp Gly Ser Phe Phe Leu Val Ser
                165                 170                 175

Arg Leu Thr Val Asp Lys Ser Arg Trp Gln Glu Gly Asn Val Phe Ser
            180                 185                 190

Cys Ser Val Met His Glu Ala Leu His Asn His Tyr Thr Gln Lys Ser
        195                 200                 205

Leu Ser Leu Ser Leu Gly Lys
    210                 215


<210> SEQ ID NO 5
<211> LENGTH: 214
<212> TYPE: PRT
<213> ORGANISM: Artificial Sequence
<220> FEATURE:
<223> OTHER INFORMATION: NTIG consensus
<220> FEATURE:
<221> NAME/KEY: VARIANT
<222> LOCATION: (18)
<223> OTHER INFORMATION: asparagine, lysine or glutamine
<220> FEATURE:
<221> NAME/KEY: VARIANT
<222> LOCATION: (196)
<223> OTHER INFORMATION: alanine, phenylalanine, isoleucien, leucine,
      valine, proline or tryptophan

<400> SEQUENCE: 5

Ser His Thr Gln Pro Leu Gly Val Phe Leu Phe Pro Pro Lys Pro Lys
1               5                   10                  15

Asp Xaa Leu Met Ile Ser Arg Thr Pro Glu Val Thr Cys Val Val Val
            20                  25                  30

Asp Val Ser Gln Glu Asp Pro Glu Val Gln Phe Asn Trp Tyr Val Asp
        35                  40                  45

Gly Val Glu Val His Asn Ala Lys Thr Lys Pro Arg Glu Glu Gln Phe
    50                  55                  60

Asn Ser Thr Tyr Arg Val Val Ser Val Leu Thr Val Leu His Gln Asp
65                  70                  75                  80

Trp Leu Asn Gly Lys Glu Tyr Lys Cys Lys Val Ser Asn Lys Gly Leu
                85                  90                  95

Pro Ser Ser Ile Glu Lys Thr Ile Ser Lys Ala Lys Gly Gln Pro Arg
            100                 105                 110

Glu Pro Gln Val Tyr Thr Leu Pro Pro Ser Gln Glu Glu Met Thr Lys
        115                 120                 125

Asn Gln Val Ser Leu Thr Cys Leu Val Lys Gly Phe Tyr Pro Ser Asp
    130                 135                 140

Ile Ala Val Glu Trp Glu Ser Asn Gly Gln Pro Glu Asn Asn Tyr Lys
145                 150                 155                 160
```

```
Thr Thr Pro Pro Val Leu Asp Ser Asp Gly Ser Phe Phe Leu Tyr Ser
                165                 170                 175

Arg Leu Thr Val Asp Lys Ser Arg Trp Gln Glu Gly Asn Val Phe Ser
            180                 185                 190

Cys Ser Val Xaa His Glu Ala Leu His Asn His Tyr Thr Gln Lys Ser
        195                 200                 205

Leu Ser Leu Ser Leu Gly
    210


<210> SEQ ID NO 6
<211> LENGTH: 214
<212> TYPE: PRT
<213> ORGANISM: Artificial Sequence
<220> FEATURE:
<223> OTHER INFORMATION: NTIG C-term lysine deleted

<400> SEQUENCE: 6

Ser His Thr Gln Pro Leu Gly Val Phe Leu Phe Pro Pro Lys Pro Lys
1               5                   10                  15

Asp Gln Leu Met Ile Ser Arg Thr Pro Glu Val Thr Cys Val Val Val
            20                  25                  30

Asp Val Ser Gln Glu Asp Pro Glu Val Gln Phe Asn Trp Tyr Val Asp
        35                  40                  45

Gly Val Glu Val His Asn Ala Lys Thr Lys Pro Arg Glu Glu Gln Phe
    50                  55                  60

Asn Ser Thr Tyr Arg Val Val Ser Val Leu Thr Val Leu His Gln Asp
65                  70                  75                  80

Trp Leu Asn Gly Lys Glu Tyr Lys Cys Lys Val Ser Asn Lys Gly Leu
                85                  90                  95

Pro Ser Ser Ile Glu Lys Thr Ile Ser Lys Ala Lys Gly Gln Pro Arg
            100                 105                 110

Glu Pro Gln Val Tyr Thr Leu Pro Pro Ser Gln Glu Glu Met Thr Lys
        115                 120                 125

Asn Gln Val Ser Leu Thr Cys Leu Val Lys Gly Phe Tyr Pro Ser Asp
    130                 135                 140

Ile Ala Val Glu Trp Glu Ser Asn Gly Gln Pro Glu Asn Asn Tyr Lys
145                 150                 155                 160

Thr Thr Pro Pro Val Leu Asp Ser Asp Gly Ser Phe Phe Leu Tyr Ser
                165                 170                 175

Arg Leu Thr Val Asp Lys Ser Arg Trp Gln Glu Gly Asn Val Phe Ser
            180                 185                 190

Cys Ser Val Leu His Glu Ala Leu His Asn His Tyr Thr Gln Lys Ser
        195                 200                 205

Leu Ser Leu Ser Leu Gly
    210


<210> SEQ ID NO 7
<211> LENGTH: 215
<212> TYPE: PRT
<213> ORGANISM: Artificial Sequence
<220> FEATURE:
<223> OTHER INFORMATION: NTIG

<400> SEQUENCE: 7

Ser His Thr Gln Pro Leu Gly Val Phe Leu Phe Pro Pro Lys Pro Lys
1               5                   10                  15

Asp Gln Leu Met Ile Ser Arg Thr Pro Glu Val Thr Cys Val Val Val
            20                  25                  30
```

```
Asp Val Ser Gln Glu Asp Pro Glu Val Gln Phe Asn Trp Tyr Val Asp
        35                  40                  45

Gly Val Glu Val His Asn Ala Lys Thr Lys Pro Arg Glu Glu Gln Phe
    50                  55                  60

Asn Ser Thr Tyr Arg Val Val Ser Val Leu Thr Val Leu His Gln Asp
65                  70                  75                  80

Trp Leu Asn Gly Lys Glu Tyr Lys Cys Lys Val Ser Asn Lys Gly Leu
                85                  90                  95

Pro Ser Ser Ile Glu Lys Thr Ile Ser Lys Ala Lys Gly Gln Pro Arg
            100                 105                 110

Glu Pro Gln Val Tyr Thr Leu Pro Pro Ser Gln Glu Glu Met Thr Lys
        115                 120                 125

Asn Gln Val Ser Leu Thr Cys Leu Val Lys Gly Phe Tyr Pro Ser Asp
    130                 135                 140

Ile Ala Val Glu Trp Glu Ser Asn Gly Gln Pro Glu Asn Asn Tyr Lys
145                 150                 155                 160

Thr Thr Pro Pro Val Leu Asp Ser Asp Gly Ser Phe Phe Leu Tyr Ser
                165                 170                 175

Arg Leu Thr Val Asp Lys Ser Arg Trp Gln Glu Gly Asn Val Phe Ser
            180                 185                 190

Cys Ser Val Leu His Glu Ala Leu His Asn His Tyr Thr Gln Lys Ser
        195                 200                 205

Leu Ser Leu Ser Leu Gly Lys
    210                 215


<210> SEQ ID NO 8
<211> LENGTH: 215
<212> TYPE: PRT
<213> ORGANISM: Artificial Sequence
<220> FEATURE:
<223> OTHER INFORMATION: NTIG Knob

<400> SEQUENCE: 8

Ser His Thr Gln Pro Leu Gly Val Phe Leu Phe Pro Pro Lys Pro Lys
1               5                   10                  15

Asp Gln Leu Met Ile Ser Arg Thr Pro Glu Val Thr Cys Val Val Val
            20                  25                  30

Asp Val Ser Gln Glu Asp Pro Glu Val Gln Phe Asn Trp Tyr Val Asp
        35                  40                  45

Gly Val Glu Val His Asn Ala Lys Thr Lys Pro Arg Glu Glu Gln Phe
    50                  55                  60

Asn Ser Thr Tyr Arg Val Val Ser Val Leu Thr Val Leu His Gln Asp
65                  70                  75                  80

Trp Leu Asn Gly Lys Glu Tyr Lys Cys Lys Val Ser Asn Lys Gly Leu
                85                  90                  95

Pro Ser Ser Ile Glu Lys Thr Ile Ser Lys Ala Lys Gly Gln Pro Arg
            100                 105                 110

Glu Pro Gln Val Tyr Thr Leu Pro Pro Cys Gln Glu Glu Met Thr Lys
        115                 120                 125

Asn Gln Val Ser Leu Trp Cys Leu Val Lys Gly Phe Tyr Pro Ser Asp
    130                 135                 140

Ile Ala Val Glu Trp Glu Ser Asn Gly Gln Pro Glu Asn Asn Tyr Lys
145                 150                 155                 160

Thr Thr Pro Pro Val Leu Asp Ser Asp Gly Ser Phe Phe Leu Tyr Ser
                165                 170                 175
```

Arg Leu Thr Val Asp Lys Ser Arg Trp Gln Glu Gly Asn Val Phe Ser
180 185 190

Cys Ser Val Leu His Glu Ala Leu His Asn His Tyr Thr Gln Lys Ser
195 200 205

Leu Ser Leu Ser Leu Gly Lys
210 215

<210> SEQ ID NO 9
<211> LENGTH: 215
<212> TYPE: PRT
<213> ORGANISM: Artificial Sequence
<220> FEATURE:
<223> OTHER INFORMATION: NTIG Hole

<400> SEQUENCE: 9

Ser His Thr Gln Pro Leu Gly Val Phe Leu Phe Pro Pro Lys Pro Lys
1 5 10 15

Asp Gln Leu Met Ile Ser Arg Thr Pro Glu Val Thr Cys Val Val Val
20 25 30

Asp Val Ser Gln Glu Asp Pro Glu Val Gln Phe Asn Trp Tyr Val Asp
35 40 45

Gly Val Glu Val His Asn Ala Lys Thr Lys Pro Arg Glu Glu Gln Phe
50 55 60

Asn Ser Thr Tyr Arg Val Val Ser Val Leu Thr Val Leu His Gln Asp
65 70 75 80

Trp Leu Asn Gly Lys Glu Tyr Lys Cys Lys Val Ser Asn Lys Gly Leu
85 90 95

Pro Ser Ser Ile Glu Lys Thr Ile Ser Lys Ala Lys Gly Gln Pro Arg
100 105 110

Glu Pro Gln Val Cys Thr Leu Pro Pro Ser Gln Glu Glu Met Thr Lys
115 120 125

Asn Gln Val Ser Leu Ser Cys Ala Val Lys Gly Phe Tyr Pro Ser Asp
130 135 140

Ile Ala Val Glu Trp Glu Ser Asn Gly Gln Pro Glu Asn Asn Tyr Lys
145 150 155 160

Thr Thr Pro Pro Val Leu Asp Ser Asp Gly Ser Phe Phe Leu Val Ser
165 170 175

Arg Leu Thr Val Asp Lys Ser Arg Trp Gln Glu Gly Asn Val Phe Ser
180 185 190

Cys Ser Val Leu His Glu Ala Leu His Asn His Tyr Thr Gln Lys Ser
195 200 205

Leu Ser Leu Ser Leu Gly Lys
210 215

<210> SEQ ID NO 10
<211> LENGTH: 642
<212> TYPE: DNA
<213> ORGANISM: Artificial Sequence
<220> FEATURE:
<223> OTHER INFORMATION: polynucleotide encoding NTIG C-term lysine deleted

<400> SEQUENCE: 10
tctcataccc agcctctggg cgtgttcctg tttcctccaa agcctaagga ccagctgatg 60
atctctcgga cccctgaagt gacctgcgtg gtggtggatg tgtctcaaga ggaccccgag 120
gtgcagttca attggtacgt ggacggcgtg gaagtgcaca acgccaagac caagcctaga 180
gaggaacagt tcaactccac ctacagagtg gtgtccgtgc tgaccgtgct gcaccaggat 240
tggctgaacg gcaaagagta caagtgcaag gtgtccaaca agggcctgcc ttccagcatc 300
gaaaagacca tctccaaggc taagggccag cctcgggaac ctcaggttta caccctgcct 360
ccaagccaag aggaaatgac caagaaccag gtgtccctga cctgcctggt caagggcttc 420
tacccttccg atatcgccgt ggaatgggag tccaatggcc agcctgagaa caactacaag 480
acaacccctc ctgtgctgga ctccgacggc tcctttttc tgtactcccg cctgaccgtg 540
gacaagtcca gatggcaaga gggcaacgtg ttctcctgct ctgtgctgca cgaggccctg 600
cacaatcact acacccagaa gtccctgtct ctgtctctgg ga 642

<210> SEQ ID NO 11
<211> LENGTH: 645
<212> TYPE: DNA
<213> ORGANISM: Artificial Sequence
<220> FEATURE:
<223> OTHER INFORMATION: polynucleotide encoding NTIG

<400> SEQUENCE: 11
tctcataccc agcctctggg cgtgttcctg tttcctccaa agcctaagga ccagctgatg 60
atctctcgga cccctgaagt gacctgcgtg gtggtggatg tgtctcaaga ggaccccgag 120
gtgcagttca attggtacgt ggacggcgtg gaagtgcaca acgccaagac caagcctaga 180
gaggaacagt tcaactccac ctacagagtg gtgtccgtgc tgaccgtgct gcaccaggat 240
tggctgaacg gcaaagagta caagtgcaag gtgtccaaca agggcctgcc ttccagcatc 300
gaaaagacca tctccaaggc taagggccag cctcgggaac ctcaggttta caccctgcct 360
ccaagccaag aggaaatgac caagaaccag gtgtccctga cctgcctggt caagggcttc 420
tacccttccg atatcgccgt ggaatgggag tccaatggcc agcctgagaa caactacaag 480
acaacccctc ctgtgctgga ctccgacggc tcctttttc tgtactcccg cctgaccgtg 540
gacaagtcca gatggcaaga gggcaacgtg ttctcctgct ctgtgctgca cgaggccctg 600
cacaatcact acacccagaa gtccctgtct ctgtctctgg gaaag 645

<210> SEQ ID NO 12
<211> LENGTH: 645
<212> TYPE: DNA
<213> ORGANISM: Artificial Sequence
<220> FEATURE:
<223> OTHER INFORMATION: polynucleotide encoding NTIG Knob

<400> SEQUENCE: 12
tctcacacac agcctctggg cgtgttcctg tttcctccaa agcctaagga ccagctgatg 60
atctctcgga cccctgaagt gacctgcgtg gtggtggatg tgtctcaaga ggaccccgag 120
gtgcagttca attggtacgt ggacggcgtg gaagtgcaca acgccaagac caagcctaga 180
gaggaacagt tcaactccac ctacagagtg gtgtccgtgc tgaccgtgct gcaccaggat 240
tggctgaacg gcaaagagta caagtgcaag gtgtccaaca agggcctgcc tagctccatc 300
gaaaagacca tctccaaggc taagggccag cctcgggaac ctcaggttta caccctgcct 360
ccatgccaag aggaaatgac caagaaccag gtgtccctgt ggtgcctggt caagggcttc 420
tacccttccg acattgccgt ggaatgggag tccaatggcc agcctgagaa caactacaag 480
accacacctc ctgtgctgga ctccgacggc tccttctttc tgtactctcg cctgaccgtg 540
gacaagtcta ggtggcaaga gggcaacgtg ttctcctgct ctgtgctgca cgaggccctg 600
cacaatcact acacccagaa gtccctgtct ctgtccctgg ggaag 645

<210> SEQ ID NO 13
<211> LENGTH: 645
<212> TYPE: DNA
<213> ORGANISM: Artificial Sequence
<220> FEATURE:
<223> OTHER INFORMATION: polynucleotide encoding NTIG hole

<400> SEQUENCE: 13
tctcacacac agcccctggg cgtgttcctg tttcctccaa agcctaagga ccagctgatg 60
atctctcgga cccctgaagt gacctgcgtg gtggtggatg tgtctcaaga ggaccccgag 120
gtgcagttca attggtacgt ggacggcgtg gaagtgcaca acgccaagac caagcctaga 180
gaggaacagt tcaactccac ctacagagtg gtgtccgtgc tgaccgtgct gcaccaggat 240
tggctgaacg gcaaagagta caagtgcaag gtgtccaaca agggcctgcc ttccagcatc 300
gaaaagacca tctccaaggc taagggccag cctcgggaac ctcaagtctg taccctgcct 360
cctagccaag aagagatgac caagaaccag gtgtccctgt cttgcgccgt gaagggcttc 420
tacccttccg acattgccgt ggaatgggag tccaatggcc agcctgagaa caactacaag 480
accacacctc ctgtgctgga ctccgacggc tctttctttc tggtgtctcg cctgaccgtg 540
gacaagtcca gatggcaaga gggcaacgtg ttctcctgct ctgtgctgca cgaggccctg 600
cacaatcact acacccagaa gtccctgagc ctgtctctgg gcaag 645

<210> SEQ ID NO 14
<211> LENGTH: 33
<212> TYPE: PRT
<213> ORGANISM: Artificial Sequence
<220> FEATURE:
<223> OTHER INFORMATION: linker peptide

<400> SEQUENCE: 14

Gly Gly Gly Gly Ser Gly Gly Gly Gly Ser Gly Gly Gly Gly Ser Glu
1               5                   10                  15

Lys Glu Lys Glu Glu Gln Glu Glu Arg Thr His Thr Cys Pro Pro Cys
            20                  25                  30

Pro

<210> SEQ ID NO 15
<211> LENGTH: 30
<212> TYPE: PRT
<213> ORGANISM: Artificial Sequence
<220> FEATURE:
<223> OTHER INFORMATION: linker peptide

<400> SEQUENCE: 15

Arg Asn Thr Gly Arg Gly Gly Glu Glu Lys Lys Gly Ser Lys Glu Lys
1               5                   10                  15

Glu Glu Gln Glu Glu Arg Glu Thr Lys Thr Pro Glu Cys Pro
            20                  25                  30

<210> SEQ ID NO 16
<211> LENGTH: 30
<212> TYPE: PRT
<213> ORGANISM: Artificial Sequence
<220> FEATURE:
<223> OTHER INFORMATION: linker peptide

<400> SEQUENCE: 16

Gly Gly Gly Gly Ser Gly Gly Gly Gly Ser Gly Gly Gly Gly Ser Glu
1               5                   10                  15

```
Pro Lys Ser Cys Asp Lys Thr His Thr Cys Pro Pro Cys Pro
            20                  25                  30


<210> SEQ ID NO 17
<211> LENGTH: 26
<212> TYPE: PRT
<213> ORGANISM: Artificial Sequence
<220> FEATURE:
<223> OTHER INFORMATION: linker peptide

<400> SEQUENCE: 17

Gly Ser Gly Gly Gly Ser Gly Thr Leu Val Thr Val Ser Ser Glu Ser
1               5                   10                  15

Lys Tyr Gly Pro Pro Cys Pro Pro Cys Pro
            20                  25


<210> SEQ ID NO 18
<211> LENGTH: 30
<212> TYPE: PRT
<213> ORGANISM: Artificial Sequence
<220> FEATURE:
<223> OTHER INFORMATION: linker peptide

<400> SEQUENCE: 18

Gly Gly Gly Gly Ser Gly Gly Gly Gly Ser Gly Gly Gly Gly Ser Glu
1               5                   10                  15

Pro Lys Ser Ser Asp Lys Thr His Thr Cys Pro Pro Cys Pro
            20                  25                  30


<210> SEQ ID NO 19
<211> LENGTH: 15
<212> TYPE: PRT
<213> ORGANISM: Artificial Sequence
<220> FEATURE:
<223> OTHER INFORMATION: linker peptide

<400> SEQUENCE: 19

Glu Pro Lys Ser Ser Asp Lys Thr His Thr Cys Pro Pro Cys Pro
1               5                   10                  15


<210> SEQ ID NO 20
<211> LENGTH: 15
<212> TYPE: PRT
<213> ORGANISM: Artificial Sequence
<220> FEATURE:
<223> OTHER INFORMATION: linker peptide

<400> SEQUENCE: 20

Glu Pro Lys Ser Cys Asp Lys Thr His Thr Cys Pro Pro Cys Pro
1               5                   10                  15


<210> SEQ ID NO 21
<211> LENGTH: 55
<212> TYPE: PRT
<213> ORGANISM: Artificial Sequence
<220> FEATURE:
<223> OTHER INFORMATION: linker peptide

<400> SEQUENCE: 21

Gly Gly Gly Gly Ser Gly Gly Gly Gly Ser Gly Gly Gly Gly Ser Ala
1               5                   10                  15

Lys Asn Thr Thr Ala Pro Ala Thr Thr Arg Asn Thr Thr Arg Gly Gly
            20                  25                  30

Glu Glu Lys Lys Lys Glu Lys Glu Lys Glu Glu Gln Glu Glu Arg Thr
```

```
        35                  40                  45

His Thr Cys Pro Pro Cys Pro
    50                  55


<210> SEQ ID NO 22
<211> LENGTH: 46
<212> TYPE: PRT
<213> ORGANISM: Artificial Sequence
<220> FEATURE:
<223> OTHER INFORMATION: linker peptide

<400> SEQUENCE: 22

Ala Glu Ala Ala Ala Lys Glu Ala Ala Ala Lys Glu Ala Ala Ala Lys
1               5                   10                  15

Glu Ala Ala Ala Lys Ala Leu Glu Ala Glu Ala Ala Ala Lys Glu Ala
            20                  25                  30

Ala Ala Lys Glu Ala Ala Ala Lys Glu Ala Ala Ala Lys Ala
        35                  40                  45


<210> SEQ ID NO 23
<211> LENGTH: 5
<212> TYPE: PRT
<213> ORGANISM: Artificial Sequence
<220> FEATURE:
<223> OTHER INFORMATION: linker peptide

<400> SEQUENCE: 23

Gly Gly Gly Gly Ser
1               5


<210> SEQ ID NO 24
<211> LENGTH: 6
<212> TYPE: PRT
<213> ORGANISM: Artificial Sequence
<220> FEATURE:
<223> OTHER INFORMATION: linker peptide

<400> SEQUENCE: 24

Gly Ser Ser Gly Gly Ser
1               5


<210> SEQ ID NO 25
<211> LENGTH: 25
<212> TYPE: PRT
<213> ORGANISM: Artificial Sequence
<220> FEATURE:
<223> OTHER INFORMATION: linker peptide

<400> SEQUENCE: 25

Ser Gly Gly Gly Ser Gly Gly Gly Gly Ser Gly Gly Gly Gly Ser Gly
1               5                   10                  15

Gly Glu Glu Gln Glu Glu Gly Gly Ser
            20                  25


<210> SEQ ID NO 26
<211> LENGTH: 20
<212> TYPE: PRT
<213> ORGANISM: Artificial Sequence
<220> FEATURE:
<223> OTHER INFORMATION: linker peptide

<400> SEQUENCE: 26

Ala Ala Gly Ser Gly Gly Gly Gly Gly Ser Gly Gly Gly Gly Ser Gly
1               5                   10                  15
```

Gly Gly Gly Ser
20

<210> SEQ ID NO 27
<211> LENGTH: 18
<212> TYPE: PRT
<213> ORGANISM: Artificial Sequence
<220> FEATURE:
<223> OTHER INFORMATION: linker peptide

<400> SEQUENCE: 27

Lys Glu Ser Gly Ser Val Ser Ser Glu Gln Leu Ala Gln Phe Arg Ser
1 5 10 15

Leu Asp

<210> SEQ ID NO 28
<211> LENGTH: 14
<212> TYPE: PRT
<213> ORGANISM: Artificial Sequence
<220> FEATURE:
<223> OTHER INFORMATION: linker peptide

<400> SEQUENCE: 28

Glu Gly Lys Ser Ser Gly Ser Gly Ser Glu Ser Lys Ser Thr
1 5 10

<210> SEQ ID NO 29
<211> LENGTH: 12
<212> TYPE: PRT
<213> ORGANISM: Artificial Sequence
<220> FEATURE:
<223> OTHER INFORMATION: linker peptide

<400> SEQUENCE: 29

Gly Ser Ala Gly Ser Ala Ala Gly Ser Gly Glu Phe
1 5 10

<210> SEQ ID NO 30
<211> LENGTH: 5
<212> TYPE: PRT
<213> ORGANISM: Artificial Sequence
<220> FEATURE:
<223> OTHER INFORMATION: linker peptide

<400> SEQUENCE: 30

Glu Ala Ala Ala Lys
1 5

<210> SEQ ID NO 31
<211> LENGTH: 12
<212> TYPE: PRT
<213> ORGANISM: Artificial Sequence
<220> FEATURE:
<223> OTHER INFORMATION: linker peptide

<400> SEQUENCE: 31

Cys Arg Arg Arg Arg Arg Arg Glu Ala Glu Ala Cys
1 5 10

<210> SEQ ID NO 32
<211> LENGTH: 8
<212> TYPE: PRT
<213> ORGANISM: Artificial Sequence
<220> FEATURE:
<223> OTHER INFORMATION: linker peptide

<400> SEQUENCE: 32

Gly Gly Gly Gly Gly Gly Gly Gly
1 5

<210> SEQ ID NO 33
<211> LENGTH: 6
<212> TYPE: PRT
<213> ORGANISM: Artificial Sequence
<220> FEATURE:
<223> OTHER INFORMATION: linker peptide

<400> SEQUENCE: 33

Gly Gly Gly Gly Gly Gly
1 5

<210> SEQ ID NO 34
<211> LENGTH: 5
<212> TYPE: PRT
<213> ORGANISM: Artificial Sequence
<220> FEATURE:
<223> OTHER INFORMATION: linker peptide

<400> SEQUENCE: 34

Pro Ala Pro Ala Pro
1 5

<210> SEQ ID NO 35
<211> LENGTH: 17
<212> TYPE: PRT
<213> ORGANISM: Artificial Sequence
<220> FEATURE:
<223> OTHER INFORMATION: linker peptide

<400> SEQUENCE: 35

Val Ser Gln Thr Ser Lys Leu Thr Arg Ala Glu Thr Val Phe Pro Asp
1 5 10 15

Val

<210> SEQ ID NO 36
<211> LENGTH: 6
<212> TYPE: PRT
<213> ORGANISM: Artificial Sequence
<220> FEATURE:
<223> OTHER INFORMATION: linker peptide

<400> SEQUENCE: 36

Pro Leu Gly Leu Trp Ala
1 5

<210> SEQ ID NO 37
<211> LENGTH: 10
<212> TYPE: PRT
<213> ORGANISM: Artificial Sequence
<220> FEATURE:
<223> OTHER INFORMATION: linker peptide

<400> SEQUENCE: 37

Thr Arg His Arg Gln Pro Arg Gly Trp Glu
1 5 10

<210> SEQ ID NO 38
<211> LENGTH: 10
<212> TYPE: PRT
<213> ORGANISM: Artificial Sequence
<220> FEATURE:
<223> OTHER INFORMATION: linker peptide

<400> SEQUENCE: 38

Ala Gly Asn Arg Val Arg Arg Ser Val Gly
1 5 10

<210> SEQ ID NO 39
<211> LENGTH: 8
<212> TYPE: PRT
<213> ORGANISM: Artificial Sequence
<220> FEATURE:
<223> OTHER INFORMATION: linker peptide

<400> SEQUENCE: 39

Arg Arg Arg Arg Arg Arg Arg Arg
1 5

<210> SEQ ID NO 40
<211> LENGTH: 31
<212> TYPE: PRT
<213> ORGANISM: Artificial Sequence
<220> FEATURE:
<223> OTHER INFORMATION: linker peptide

<400> SEQUENCE: 40

Gly Ser Ser Gly Gly Ser Gly Ser Ser Gly Gly Ser Gly Gly Gly Asp
1 5 10 15

Glu Ala Asp Gly Ser Arg Gly Ser Gln Lys Ala Gly Val Asp Glu
20 25 30

<210> SEQ ID NO 41
<211> LENGTH: 15
<212> TYPE: PRT
<213> ORGANISM: Artificial Sequence
<220> FEATURE:
<223> OTHER INFORMATION: linker peptide

<400> SEQUENCE: 41

Gly Gly Gly Gly Ser Gly Gly Gly Gly Ser Gly Gly Gly Gly Ser
1 5 10 15

<210> SEQ ID NO 42
<211> LENGTH: 13
<212> TYPE: PRT
<213> ORGANISM: Artificial Sequence
<220> FEATURE:
<223> OTHER INFORMATION: linker peptide

<400> SEQUENCE: 42

Ala Glu Ala Ala Ala Lys Glu Ala Ala Ala Ala Lys Ala
1 5 10

<210> SEQ ID NO 43
<211> LENGTH: 4
<212> TYPE: PRT
<213> ORGANISM: Artificial Sequence
<220> FEATURE:
<223> OTHER INFORMATION: linker peptide

<400> SEQUENCE: 43

Gly Phe Leu Gly
1

<210> SEQ ID NO 44
<211> LENGTH: 40
<212> TYPE: PRT
<213> ORGANISM: Artificial Sequence
<220> FEATURE:

<223> OTHER INFORMATION: linker peptide

<400> SEQUENCE: 44

Ala Lys Ala Thr Thr Ala Pro Ala Thr Thr Arg Asn Thr Gly Arg Gly
1 5 10 15

Gly Glu Glu Lys Lys Lys Glu Lys Glu Lys Glu Glu Gln Glu Glu Arg
20 25 30

Glu Thr Lys Thr Pro Glu Cys Pro
35 40

<210> SEQ ID NO 45
<211> LENGTH: 5
<212> TYPE: PRT
<213> ORGANISM: Artificial Sequence
<220> FEATURE:
<223> OTHER INFORMATION: linker peptide

<400> SEQUENCE: 45

Gly Gly Ser Gly Gly
1 5

<210> SEQ ID NO 46
<211> LENGTH: 9
<212> TYPE: PRT
<213> ORGANISM: Artificial Sequence
<220> FEATURE:
<223> OTHER INFORMATION: linker peptide

<400> SEQUENCE: 46

Gly Gly Ser Gly Gly Ser Gly Gly Ser
1 5

<210> SEQ ID NO 47
<211> LENGTH: 6
<212> TYPE: PRT
<213> ORGANISM: Artificial Sequence
<220> FEATURE:
<223> OTHER INFORMATION: linker peptide

<400> SEQUENCE: 47

Gly Gly Gly Ser Gly Gly
1 5

<210> SEQ ID NO 48
<211> LENGTH: 15
<212> TYPE: PRT
<213> ORGANISM: Artificial Sequence
<220> FEATURE:
<223> OTHER INFORMATION: linker peptide

<400> SEQUENCE: 48

Gly Ser Thr Ser Gly Ser Gly Lys Pro Gly Ser Gly Glu Gly Ser
1 5 10 15

<210> SEQ ID NO 49
<211> LENGTH: 39
<212> TYPE: PRT
<213> ORGANISM: Artificial Sequence
<220> FEATURE:
<223> OTHER INFORMATION: GLP-1/Exendin hybrid peptide

<400> SEQUENCE: 49

His Gly Glu Gly Thr Phe Thr Ser Asp Val Ser Ser Tyr Leu Glu Gly
1 5 10 15

Gln Ala Ala Lys Glu Phe Ile Ala Trp Leu Val Lys Gly Gly Pro Ser

```
            20                  25                  30

Ser Gly Ala Pro Pro Pro Ser
        35


<210> SEQ ID NO 50
<211> LENGTH: 287
<212> TYPE: PRT
<213> ORGANISM: Artificial Sequence
<220> FEATURE:
<223> OTHER INFORMATION: GLP-1E-NTIG

<400> SEQUENCE: 50

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Pro Ser
            20                  25                  30

Ser Gly Ala Pro Pro Pro Ser Gly Gly Gly Gly Ser Gly Gly Gly Gly
        35                  40                  45

Ser Gly Gly Gly Gly Ser Glu Lys Glu Lys Glu Glu Gln Glu Glu Arg
    50                  55                  60

Thr His Thr Cys Pro Pro Cys Pro Ser His Thr Gln Pro Leu Gly Val
65                  70                  75                  80

Phe Leu Phe Pro Pro Lys Pro Lys Asp Gln Leu Met Ile Ser Arg Thr
                85                  90                  95

Pro Glu Val Thr Cys Val Val Val Asp Val Ser Gln Glu Asp Pro Glu
            100                 105                 110

Val Gln Phe Asn Trp Tyr Val Asp Gly Val Glu Val His Asn Ala Lys
        115                 120                 125

Thr Lys Pro Arg Glu Glu Gln Phe Asn Ser Thr Tyr Arg Val Val Ser
    130                 135                 140

Val Leu Thr Val Leu His Gln Asp Trp Leu Asn Gly Lys Glu Tyr Lys
145                 150                 155                 160

Cys Lys Val Ser Asn Lys Gly Leu Pro Ser Ser Ile Glu Lys Thr Ile
                165                 170                 175

Ser Lys Ala Lys Gly Gln Pro Arg Glu Pro Gln Val Tyr Thr Leu Pro
            180                 185                 190

Pro Ser Gln Glu Glu Met Thr Lys Asn Gln Val Ser Leu Thr Cys Leu
        195                 200                 205

Val Lys Gly Phe Tyr Pro Ser Asp Ile Ala Val Glu Trp Glu Ser Asn
    210                 215                 220

Gly Gln Pro Glu Asn Asn Tyr Lys Thr Thr Pro Pro Val Leu Asp Ser
225                 230                 235                 240

Asp Gly Ser Phe Phe Leu Tyr Ser Arg Leu Thr Val Asp Lys Ser Arg
                245                 250                 255

Trp Gln Glu Gly Asn Val Phe Ser Cys Ser Val Leu His Glu Ala Leu
            260                 265                 270

His Asn His Tyr Thr Gln Lys Ser Leu Ser Leu Ser Leu Gly Lys
        275                 280                 285


<210> SEQ ID NO 51
<211> LENGTH: 25
<212> TYPE: PRT
<213> ORGANISM: Artificial Sequence
<220> FEATURE:
<223> OTHER INFORMATION: tPA signal peptide

<400> SEQUENCE: 51
```

```
Met Asp Ala Met Leu Arg Gly Leu Cys Cys Val Leu Leu Leu Cys Gly
1               5                   10                  15

Ala Val Phe Val Ser Pro Ser His Ala
            20                  25


<210> SEQ ID NO 52
<211> LENGTH: 33
<212> TYPE: PRT
<213> ORGANISM: Artificial Sequence
<220> FEATURE:
<223> OTHER INFORMATION: GLP-2-2G (Teduglutide)

<400> SEQUENCE: 52

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp


<210> SEQ ID NO 53
<211> LENGTH: 281
<212> TYPE: PRT
<213> ORGANISM: Artificial Sequence
<220> FEATURE:
<223> OTHER INFORMATION: GLP-2-2G-NTIG

<400> SEQUENCE: 53

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Gly Gly Gly Gly Ser Gly Gly Gly Gly Ser Gly Gly Gly Gly Ser
        35                  40                  45

Glu Lys Glu Lys Glu Glu Gln Glu Glu Arg Thr His Thr Cys Pro Pro
    50                  55                  60

Cys Pro Ser His Thr Gln Pro Leu Gly Val Phe Leu Phe Pro Pro Lys
65                  70                  75                  80

Pro Lys Asp Gln Leu Met Ile Ser Arg Thr Pro Glu Val Thr Cys Val
                85                  90                  95

Val Val Asp Val Ser Gln Glu Asp Pro Glu Val Gln Phe Asn Trp Tyr
            100                 105                 110

Val Asp Gly Val Glu Val His Asn Ala Lys Thr Lys Pro Arg Glu Glu
        115                 120                 125

Gln Phe Asn Ser Thr Tyr Arg Val Val Ser Val Leu Thr Val Leu His
    130                 135                 140

Gln Asp Trp Leu Asn Gly Lys Glu Tyr Lys Cys Lys Val Ser Asn Lys
145                 150                 155                 160

Gly Leu Pro Ser Ser Ile Glu Lys Thr Ile Ser Lys Ala Lys Gly Gln
                165                 170                 175

Pro Arg Glu Pro Gln Val Tyr Thr Leu Pro Pro Ser Gln Glu Glu Met
            180                 185                 190

Thr Lys Asn Gln Val Ser Leu Thr Cys Leu Val Lys Gly Phe Tyr Pro
        195                 200                 205

Ser Asp Ile Ala Val Glu Trp Glu Ser Asn Gly Gln Pro Glu Asn Asn
    210                 215                 220

Tyr Lys Thr Thr Pro Pro Val Leu Asp Ser Asp Gly Ser Phe Phe Leu
225                 230                 235                 240
```

```
Tyr Ser Arg Leu Thr Val Asp Lys Ser Arg Trp Gln Glu Gly Asn Val
                245                 250                 255

Phe Ser Cys Ser Val Leu His Glu Ala Leu His Asn His Tyr Thr Gln
            260                 265                 270

Lys Ser Leu Ser Leu Ser Leu Gly Lys
        275                 280


<210> SEQ ID NO 54
<211> LENGTH: 160
<212> TYPE: PRT
<213> ORGANISM: Artificial Sequence
<220> FEATURE:
<223> OTHER INFORMATION: IL-10V

<400> SEQUENCE: 54

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ala Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160


<210> SEQ ID NO 55
<211> LENGTH: 425
<212> TYPE: PRT
<213> ORGANISM: Artificial Sequence
<220> FEATURE:
<223> OTHER INFORMATION: NTIG-IL-10V

<400> SEQUENCE: 55

Gly Gly Gly Gly Ser Gly Gly Gly Gly Ser Gly Gly Gly Gly Ser Glu
1               5                   10                  15

Pro Lys Ser Ser Asp Lys Thr His Thr Cys Pro Pro Cys Pro Ser His
            20                  25                  30

Thr Gln Pro Leu Gly Val Phe Leu Phe Pro Pro Lys Pro Lys Asp Gln
        35                  40                  45

Leu Met Ile Ser Arg Thr Pro Glu Val Thr Cys Val Val Val Asp Val
    50                  55                  60

Ser Gln Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

Thr Tyr Arg Val Val Ser Val Leu Thr Val Leu His Gln Asp Trp Leu
            100                 105                 110
```

Asn Gly Lys Glu Tyr Lys Cys Lys Val Ser Asn Lys Gly Leu Pro Ser
115 120 125

Ser Ile Glu Lys Thr Ile Ser Lys Ala Lys Gly Gln Pro Arg Glu Pro
130 135 140

Gln Val Tyr Thr Leu Pro Pro Ser Gln Glu Glu Met Thr Lys Asn Gln
145 150 155 160

Val Ser Leu Thr Cys Leu Val Lys Gly Phe Tyr Pro Ser Asp Ile Ala
165 170 175

Val Glu Trp Glu Ser Asn Gly Gln Pro Glu Asn Asn Tyr Lys Thr Thr
180 185 190

Pro Pro Val Leu Asp Ser Asp Gly Ser Phe Phe Leu Tyr Ser Arg Leu
195 200 205

Thr Val Asp Lys Ser Arg Trp Gln Glu Gly Asn Val Phe Ser Cys Ser
210 215 220

Val Leu His Glu Ala Leu His Asn His Tyr Thr Gln Lys Ser Leu Ser
225 230 235 240

Leu Ser Leu Gly Lys Ala Ala Gly Ser Gly Gly Gly Gly Gly Ser Gly
245 250 255

Gly Gly Gly Ser Gly Gly Gly Gly Ser Ser Pro Gly Gln Gly Thr Gln
260 265 270

Ser Glu Asn Ser Cys Thr His Phe Pro Gly Asn Leu Pro Asn Met Leu
275 280 285

Arg Asp Leu Arg Asp Ala Phe Ser Arg Val Lys Thr Phe Phe Gln Met
290 295 300

Lys Asp Gln Leu Asp Asn Leu Leu Leu Lys Glu Ser Leu Leu Glu Asp
305 310 315 320

Phe Lys Gly Tyr Leu Gly Cys Gln Ala Leu Ser Glu Met Ile Gln Phe
325 330 335

Tyr Leu Glu Glu Val Met Pro Gln Ala Glu Asn Gln Asp Pro Asp Ala
340 345 350

Lys Ala His Val Asn Ser Leu Gly Glu Asn Leu Lys Thr Leu Arg Leu
355 360 365

Arg Leu Arg Arg Cys His Arg Phe Leu Pro Cys Glu Asn Lys Ser Lys
370 375 380

Ala Val Glu Gln Val Lys Asn Ala Phe Asn Lys Leu Gln Glu Lys Gly
385 390 395 400

Ile Tyr Lys Ala Met Ser Glu Phe Asp Ile Phe Ile Asn Tyr Ile Glu
405 410 415

Ala Tyr Met Thr Met Lys Ile Arg Asn
420 425

<210> SEQ ID NO 56
<211> LENGTH: 169
<212> TYPE: PRT
<213> ORGANISM: Artificial Sequence
<220> FEATURE:
<223> OTHER INFORMATION: IL-10Vm

<400> SEQUENCE: 56

Ser Pro Gly Gln Gly Thr Gln Ser Glu Asn Ser Cys Thr His Phe Pro
1 5 10 15

Gly Asn Leu Pro Asn Met Leu Arg Asp Leu Arg Asp Ala Phe Ser Arg
20 25 30

Val Lys Thr Phe Phe Gln Met Lys Asp Gln Leu Asp Asn Leu Leu Leu
35 40 45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ala Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Gly Gly Ser Gly Gly Ser Gly Gly Ser Lys Ser Lys
        115                 120                 125

Ala Val Glu Gln Val Lys Asn Ala Phe Asn Lys Leu Gln Glu Lys Gly
    130                 135                 140

Ile Tyr Lys Ala Met Ser Glu Phe Asp Ile Phe Ile Asn Tyr Ile Glu
145                 150                 155                 160

Ala Tyr Met Thr Met Lys Ile Arg Asn
                165

<210> SEQ ID NO 57
<211> LENGTH: 403
<212> TYPE: PRT
<213> ORGANISM: Artificial Sequence
<220> FEATURE:
<223> OTHER INFORMATION: NTIG-IL-10Vm

<400> SEQUENCE: 57

Ser His Thr Gln Pro Leu Gly Val Phe Leu Phe Pro Pro Lys Pro Lys
1               5                   10                  15

Asp Gln Leu Met Ile Ser Arg Thr Pro Glu Val Thr Cys Val Val Val
            20                  25                  30

Asp Val Ser Gln Glu Asp Pro Glu Val Gln Phe Asn Trp Tyr Val Asp
        35                  40                  45

Gly Val Glu Val His Asn Ala Lys Thr Lys Pro Arg Glu Glu Gln Phe
    50                  55                  60

Asn Ser Thr Tyr Arg Val Val Ser Val Leu Thr Val Leu His Gln Asp
65                  70                  75                  80

Trp Leu Asn Gly Lys Glu Tyr Lys Cys Lys Val Ser Asn Lys Gly Leu
                85                  90                  95

Pro Ser Ser Ile Glu Lys Thr Ile Ser Lys Ala Lys Gly Gln Pro Arg
            100                 105                 110

Glu Pro Gln Val Tyr Thr Leu Pro Pro Ser Gln Glu Glu Met Thr Lys
        115                 120                 125

Asn Gln Val Ser Leu Thr Cys Leu Val Lys Gly Phe Tyr Pro Ser Asp
    130                 135                 140

Ile Ala Val Glu Trp Glu Ser Asn Gly Gln Pro Glu Asn Asn Tyr Lys
145                 150                 155                 160

Thr Thr Pro Pro Val Leu Asp Ser Asp Gly Ser Phe Phe Leu Tyr Ser
                165                 170                 175

Arg Leu Thr Val Asp Lys Ser Arg Trp Gln Glu Gly Asn Val Phe Ser
            180                 185                 190

Cys Ser Val Leu His Glu Ala Leu His Asn His Tyr Thr Gln Lys Ser
        195                 200                 205

Leu Ser Leu Ser Leu Gly Ala Ala Gly Ser Gly Gly Gly Gly Ser
    210                 215                 220

Gly Gly Gly Gly Ser Gly Gly Gly Gly Ser Ser Pro Gly Gln Gly Thr
225                 230                 235                 240

```
Gln Ser Glu Asn Ser Cys Thr His Phe Pro Gly Asn Leu Pro Asn Met
                245                 250                 255

Leu Arg Asp Leu Arg Asp Ala Phe Ser Arg Val Lys Thr Phe Phe Gln
            260                 265                 270

Met Lys Asp Gln Leu Asp Asn Leu Leu Leu Lys Glu Ser Leu Leu Glu
        275                 280                 285

Asp Phe Lys Gly Tyr Leu Gly Cys Gln Ala Leu Ser Glu Met Ile Gln
    290                 295                 300

Phe Tyr Leu Glu Glu Val Met Pro Gln Ala Glu Asn Gln Asp Pro Asp
305                 310                 315                 320

Ala Lys Ala His Val Asn Ser Leu Gly Glu Asn Leu Lys Thr Leu Arg
                325                 330                 335

Leu Arg Leu Arg Arg Cys His Arg Phe Leu Pro Cys Glu Asn Gly Gly
            340                 345                 350

Ser Gly Gly Ser Gly Gly Ser Lys Ser Lys Ala Val Glu Gln Val Lys
        355                 360                 365

Asn Ala Phe Asn Lys Leu Gln Glu Lys Gly Ile Tyr Lys Ala Met Ser
    370                 375                 380

Glu Phe Asp Ile Phe Ile Asn Tyr Ile Glu Ala Tyr Met Thr Met Lys
385                 390                 395                 400

Ile Arg Asn


<210> SEQ ID NO 58
<211> LENGTH: 180
<212> TYPE: PRT
<213> ORGANISM: Artificial Sequence
<220> FEATURE:
<223> OTHER INFORMATION: FceRIa

<400> SEQUENCE: 58

Val Pro Gln Lys Pro Lys Val Ser Leu Asn Pro Pro Trp Asn Arg Ile
1               5                   10                  15

Phe Lys Gly Glu Asn Val Thr Leu Thr Cys Asn Gly Asn Asn Phe Phe
            20                  25                  30

Glu Val Ser Ser Thr Lys Trp Phe His Asn Gly Ser Leu Ser Glu Glu
        35                  40                  45

Thr Asn Ser Ser Leu Asn Ile Val Asn Ala Lys Phe Glu Asp Ser Gly
    50                  55                  60

Glu Tyr Lys Cys Gln His Gln Gln Val Asn Glu Ser Glu Pro Val Tyr
65                  70                  75                  80

Leu Glu Val Phe Ser Asp Trp Leu Leu Leu Gln Ala Ser Ala Glu Val
                85                  90                  95

Val Met Glu Gly Gln Pro Leu Phe Leu Arg Cys His Gly Trp Arg Asn
            100                 105                 110

Trp Asp Val Tyr Lys Val Ile Tyr Tyr Lys Asp Gly Glu Ala Leu Lys
        115                 120                 125

Tyr Trp Tyr Glu Asn His Asn Ile Ser Ile Thr Asn Ala Thr Val Glu
    130                 135                 140

Asp Ser Gly Thr Tyr Tyr Cys Thr Gly Lys Val Trp Gln Leu Asp Tyr
145                 150                 155                 160

Glu Ser Glu Pro Leu Asn Ile Thr Val Ile Lys Ala Pro Arg Glu Lys
                165                 170                 175

Tyr Trp Leu Gln
            180
```

```
<210> SEQ ID NO 59
<211> LENGTH: 605
<212> TYPE: PRT
<213> ORGANISM: Artificial Sequence
<220> FEATURE:
<223> OTHER INFORMATION: FceRIa-NTIG-IL-10V

<400> SEQUENCE: 59

Val Pro Gln Lys Pro Lys Val Ser Leu Asn Pro Pro Trp Asn Arg Ile
1               5                   10                  15

Phe Lys Gly Glu Asn Val Thr Leu Thr Cys Asn Gly Asn Asn Phe Phe
            20                  25                  30

Glu Val Ser Ser Thr Lys Trp Phe His Asn Gly Ser Leu Ser Glu Glu
        35                  40                  45

Thr Asn Ser Ser Leu Asn Ile Val Asn Ala Lys Phe Glu Asp Ser Gly
    50                  55                  60

Glu Tyr Lys Cys Gln His Gln Gln Val Asn Glu Ser Glu Pro Val Tyr
65                  70                  75                  80

Leu Glu Val Phe Ser Asp Trp Leu Leu Leu Gln Ala Ser Ala Glu Val
                85                  90                  95

Val Met Glu Gly Gln Pro Leu Phe Leu Arg Cys His Gly Trp Arg Asn
            100                 105                 110

Trp Asp Val Tyr Lys Val Ile Tyr Tyr Lys Asp Gly Glu Ala Leu Lys
        115                 120                 125

Tyr Trp Tyr Glu Asn His Asn Ile Ser Ile Thr Asn Ala Thr Val Glu
    130                 135                 140

Asp Ser Gly Thr Tyr Tyr Cys Thr Gly Lys Val Trp Gln Leu Asp Tyr
145                 150                 155                 160

Glu Ser Glu Pro Leu Asn Ile Thr Val Ile Lys Ala Pro Arg Glu Lys
                165                 170                 175

Tyr Trp Leu Gln Gly Gly Gly Gly Ser Gly Gly Gly Gly Ser Gly Gly
            180                 185                 190

Gly Gly Ser Glu Pro Lys Ser Ser Asp Lys Thr His Thr Cys Pro Pro
        195                 200                 205

Cys Pro Ser His Thr Gln Pro Leu Gly Val Phe Leu Phe Pro Pro Lys
    210                 215                 220

Pro Lys Asp Gln Leu Met Ile Ser Arg Thr Pro Glu Val Thr Cys Val
225                 230                 235                 240

Val Val Asp Val Ser Gln Glu Asp Pro Glu Val Gln Phe Asn Trp Tyr
                245                 250                 255

Val Asp Gly Val Glu Val His Asn Ala Lys Thr Lys Pro Arg Glu Glu
            260                 265                 270

Gln Phe Asn Ser Thr Tyr Arg Val Val Ser Val Leu Thr Val Leu His
        275                 280                 285

Gln Asp Trp Leu Asn Gly Lys Glu Tyr Lys Cys Lys Val Ser Asn Lys
    290                 295                 300

Gly Leu Pro Ser Ser Ile Glu Lys Thr Ile Ser Lys Ala Lys Gly Gln
305                 310                 315                 320

Pro Arg Glu Pro Gln Val Tyr Thr Leu Pro Pro Ser Gln Glu Glu Met
                325                 330                 335

Thr Lys Asn Gln Val Ser Leu Thr Cys Leu Val Lys Gly Phe Tyr Pro
            340                 345                 350

Ser Asp Ile Ala Val Glu Trp Glu Ser Asn Gly Gln Pro Glu Asn Asn
        355                 360                 365
```

```
Tyr Lys Thr Thr Pro Pro Val Leu Asp Ser Asp Gly Ser Phe Phe Leu
    370                 375                 380

Tyr Ser Arg Leu Thr Val Asp Lys Ser Arg Trp Gln Glu Gly Asn Val
385                 390                 395                 400

Phe Ser Cys Ser Val Leu His Glu Ala Leu His Asn His Tyr Thr Gln
                405                 410                 415

Lys Ser Leu Ser Leu Ser Leu Gly Lys Ala Ala Gly Ser Gly Gly Gly
            420                 425                 430

Gly Gly Ser Gly Gly Gly Gly Ser Gly Gly Gly Gly Ser Ser Pro Gly
        435                 440                 445

Gln Gly Thr Gln Ser Glu Asn Ser Cys Thr His Phe Pro Gly Asn Leu
    450                 455                 460

Pro Asn Met Leu Arg Asp Leu Arg Asp Ala Phe Ser Arg Val Lys Thr
465                 470                 475                 480

Phe Phe Gln Met Lys Asp Gln Leu Asp Asn Leu Leu Leu Lys Glu Ser
                485                 490                 495

Leu Leu Glu Asp Phe Lys Gly Tyr Leu Gly Cys Gln Ala Leu Ser Glu
            500                 505                 510

Met Ile Gln Phe Tyr Leu Glu Glu Val Met Pro Gln Ala Glu Asn Gln
        515                 520                 525

Asp Pro Asp Ala Lys Ala His Val Asn Ser Leu Gly Glu Asn Leu Lys
    530                 535                 540

Thr Leu Arg Leu Arg Leu Arg Arg Cys His Arg Phe Leu Pro Cys Glu
545                 550                 555                 560

Asn Lys Ser Lys Ala Val Glu Gln Val Lys Asn Ala Phe Asn Lys Leu
                565                 570                 575

Gln Glu Lys Gly Ile Tyr Lys Ala Met Ser Glu Phe Asp Ile Phe Ile
            580                 585                 590

Asn Tyr Ile Glu Ala Tyr Met Thr Met Lys Ile Arg Asn
        595                 600                 605


<210> SEQ ID NO 60
<211> LENGTH: 613
<212> TYPE: PRT
<213> ORGANISM: Artificial Sequence
<220> FEATURE:
<223> OTHER INFORMATION: FceRIa-NTIG-IL-10Vm

<400> SEQUENCE: 60

Val Pro Gln Lys Pro Lys Val Ser Leu Asn Pro Pro Trp Asn Arg Ile
1               5                   10                  15

Phe Lys Gly Glu Asn Val Thr Leu Thr Cys Asn Gly Asn Asn Phe Phe
            20                  25                  30

Glu Val Ser Ser Thr Lys Trp Phe His Asn Gly Ser Leu Ser Glu Glu
        35                  40                  45

Thr Asn Ser Ser Leu Asn Ile Val Asn Ala Lys Phe Glu Asp Ser Gly
    50                  55                  60

Glu Tyr Lys Cys Gln His Gln Gln Val Asn Glu Ser Glu Pro Val Tyr
65                  70                  75                  80

Leu Glu Val Phe Ser Asp Trp Leu Leu Leu Gln Ala Ser Ala Glu Val
                85                  90                  95

Val Met Glu Gly Gln Pro Leu Phe Leu Arg Cys His Gly Trp Arg Asn
            100                 105                 110

Trp Asp Val Tyr Lys Val Ile Tyr Tyr Lys Asp Gly Glu Ala Leu Lys
        115                 120                 125
```

```
Tyr Trp Tyr Glu Asn His Asn Ile Ser Ile Thr Asn Ala Thr Val Glu
    130                 135                 140

Asp Ser Gly Thr Tyr Tyr Cys Thr Gly Lys Val Trp Gln Leu Asp Tyr
145                 150                 155                 160

Glu Ser Glu Pro Leu Asn Ile Thr Val Ile Lys Ala Pro Arg Glu Lys
                165                 170                 175

Tyr Trp Leu Gln Gly Gly Gly Gly Ser Gly Gly Gly Gly Ser Gly Gly
            180                 185                 190

Gly Gly Ser Glu Pro Lys Ser Ser Asp Lys Thr His Thr Cys Pro Pro
        195                 200                 205

Cys Pro Ser His Thr Gln Pro Leu Gly Val Phe Leu Phe Pro Pro Lys
    210                 215                 220

Pro Lys Asp Gln Leu Met Ile Ser Arg Thr Pro Glu Val Thr Cys Val
225                 230                 235                 240

Val Val Asp Val Ser Gln Glu Asp Pro Glu Val Gln Phe Asn Trp Tyr
                245                 250                 255

Val Asp Gly Val Glu Val His Asn Ala Lys Thr Lys Pro Arg Glu Glu
            260                 265                 270

Gln Phe Asn Ser Thr Tyr Arg Val Val Ser Val Leu Thr Val Leu His
        275                 280                 285

Gln Asp Trp Leu Asn Gly Lys Glu Tyr Lys Cys Lys Val Ser Asn Lys
    290                 295                 300

Gly Leu Pro Ser Ser Ile Glu Lys Thr Ile Ser Lys Ala Lys Gly Gln
305                 310                 315                 320

Pro Arg Glu Pro Gln Val Tyr Thr Leu Pro Pro Ser Gln Glu Glu Met
                325                 330                 335

Thr Lys Asn Gln Val Ser Leu Thr Cys Leu Val Lys Gly Phe Tyr Pro
            340                 345                 350

Ser Asp Ile Ala Val Glu Trp Glu Ser Asn Gly Gln Pro Glu Asn Asn
        355                 360                 365

Tyr Lys Thr Thr Pro Pro Val Leu Asp Ser Asp Gly Ser Phe Phe Leu
    370                 375                 380

Tyr Ser Arg Leu Thr Val Asp Lys Ser Arg Trp Gln Glu Gly Asn Val
385                 390                 395                 400

Phe Ser Cys Ser Val Leu His Glu Ala Leu His Asn His Tyr Thr Gln
                405                 410                 415

Lys Ser Leu Ser Leu Ser Leu Gly Ala Ala Gly Ser Gly Gly Gly Gly
            420                 425                 430

Gly Ser Gly Gly Gly Gly Ser Gly Gly Gly Gly Ser Ser Pro Gly Gln
        435                 440                 445

Gly Thr Gln Ser Glu Asn Ser Cys Thr His Phe Pro Gly Asn Leu Pro
    450                 455                 460

Asn Met Leu Arg Asp Leu Arg Asp Ala Phe Ser Arg Val Lys Thr Phe
465                 470                 475                 480

Phe Gln Met Lys Asp Gln Leu Asp Asn Leu Leu Leu Lys Glu Ser Leu
                485                 490                 495

Leu Glu Asp Phe Lys Gly Tyr Leu Gly Cys Gln Ala Leu Ser Glu Met
            500                 505                 510

Ile Gln Phe Tyr Leu Glu Glu Val Met Pro Gln Ala Glu Asn Gln Asp
        515                 520                 525

Pro Asp Ala Lys Ala His Val Asn Ser Leu Gly Glu Asn Leu Lys Thr
    530                 535                 540

Leu Arg Leu Arg Leu Arg Arg Cys His Arg Phe Leu Pro Cys Glu Asn
```

545 550 555 560

Gly Gly Ser Gly Gly Ser Gly Gly Ser Lys Ser Lys Ala Val Glu Gln
565 570 575

Val Lys Asn Ala Phe Asn Lys Leu Gln Glu Lys Gly Ile Tyr Lys Ala
580 585 590

Met Ser Glu Phe Asp Ile Phe Ile Asn Tyr Ile Glu Ala Tyr Met Thr
595 600 605

Met Lys Ile Arg Asn
610

<210> SEQ ID NO 61
<211> LENGTH: 216
<212> TYPE: PRT
<213> ORGANISM: Artificial Sequence
<220> FEATURE:
<223> OTHER INFORMATION: Chimeric anti-CD40L heavy chain VH-CH1

<400> SEQUENCE: 61

Glu Val Gln Leu Gln Gln Ser Gly Ser Glu Leu Val Lys Pro Gly Ala
1 5 10 15

Ser Val Lys Leu Ser Cys Lys Ala Ser Gly Tyr Ile Phe Thr Ser Tyr
20 25 30

Tyr Met Tyr Trp Val Lys Gln Arg Pro Gly Gln Gly Leu Glu Trp Ile
35 40 45

Gly Glu Ile Asn Pro Ser Asn Gly Asp Thr Asn Phe Asn Glu Lys Phe
50 55 60

Lys Ser Lys Ala Thr Leu Thr Val Asp Lys Ser Ser Ser Thr Ala Tyr
65 70 75 80

Met Gln Leu Ile Ser Leu Thr Ser Glu Asp Ser Ala Val Tyr Tyr Cys
85 90 95

Thr Arg Ser Asp Gly Arg Asn Asp Met Asp Ser Trp Gly Gln Gly Thr
100 105 110

Thr Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val
210 215

<210> SEQ ID NO 62
<211> LENGTH: 218
<212> TYPE: PRT
<213> ORGANISM: Artificial Sequence
<220> FEATURE:
<223> OTHER INFORMATION: chimeric anti-CD40L light chain

<400> SEQUENCE: 62

Asp Ile Gln Leu Thr Gln Ser Pro Ala Ser Leu Ala Val Ser Leu Gly
1 5 10 15

```
Gln Arg Ala Thr Ile Ser Cys Arg Ala Ser Gln Arg Val Ser Ser Ser
            20                  25                  30

Thr Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ser Ala Thr Tyr Tyr Cys Gln His Ser Trp
                85                  90                  95

Glu Ile Pro Pro Thr Phe Gly Gly Gly Thr Lys Leu Glu Ile Lys Arg
            100                 105                 110

Ala Asp Ala Ala Pro Thr Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 63
<211> LENGTH: 19
<212> TYPE: PRT
<213> ORGANISM: Artificial Sequence
<220> FEATURE:
<223> OTHER INFORMATION: IgG1 heavy chain signal sequence

<400> SEQUENCE: 63

Met Gly Trp Ser Cys Ile Ile Leu Phe Leu Val Ala Thr Ala Thr Gly
1               5                   10                  15

Val His Ser


<210> SEQ ID NO 64
<211> LENGTH: 216
<212> TYPE: PRT
<213> ORGANISM: Artificial Sequence
<220> FEATURE:
<223> OTHER INFORMATION: humanized anti-CD40L heavy chain VH-CH1

<400> SEQUENCE: 64

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr
            20                  25                  30

Tyr Met Tyr Trp Val Lys Gln Ala Pro Gly Gln Gly Leu Glu Trp Ile
        35                  40                  45

Gly Glu Ile Asn Pro Ser Asn Gly Asp Thr Asn Phe Asn Glu Lys Phe
    50                  55                  60

Lys Ser Lys Ala Thr Leu Thr Val Asp Lys Ser Ala Ser Thr Ala Tyr
65                  70                  75                  80
```

```
Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val
    210                 215


<210> SEQ ID NO 65
<211> LENGTH: 230
<212> TYPE: PRT
<213> ORGANISM: Artificial Sequence
<220> FEATURE:
<223> OTHER INFORMATION: hinge + NTIG

<400> SEQUENCE: 65

Glu Pro Lys Ser Cys Asp Lys Thr His Thr Cys Pro Pro Cys Pro Ser
1               5                   10                  15

His Thr Gln Pro Leu Gly Val Phe Leu Phe Pro Pro Lys Pro Lys Asp
            20                  25                  30

Gln Leu Met Ile Ser Arg Thr Pro Glu Val Thr Cys Val Val Val Asp
        35                  40                  45

Val Ser Gln Glu Asp Pro Glu Val Gln Phe Asn Trp Tyr Val Asp Gly
    50                  55                  60

Val Glu Val His Asn Ala Lys Thr Lys Pro Arg Glu Glu Gln Phe Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Gly Leu Pro
            100                 105                 110

Ser Ser Ile Glu Lys Thr Ile Ser Lys Ala Lys Gly Gln Pro Arg Glu
        115                 120                 125

Pro Gln Val Tyr Thr Leu Pro Pro Ser Gln Glu Glu Met Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Arg
            180                 185                 190

Leu Thr Val Asp Lys Ser Arg Trp Gln Glu Gly Asn Val Phe Ser Cys
        195                 200                 205

Ser Val Leu His Glu Ala Leu His Asn His Tyr Thr Gln Lys Ser Leu
    210                 215                 220
```

```
Ser Leu Ser Leu Gly Lys
225                 230


<210> SEQ ID NO 66
<211> LENGTH: 20
<212> TYPE: PRT
<213> ORGANISM: Artificial Sequence
<220> FEATURE:
<223> OTHER INFORMATION: IgG1 light chain signal sequence

<400> SEQUENCE: 66

Met Glu Thr Asp Thr Leu Leu Leu Trp Val Leu Leu Leu Trp Val Pro
1               5                   10                  15

Gly Ser Thr Gly
            20


<210> SEQ ID NO 67
<211> LENGTH: 218
<212> TYPE: PRT
<213> ORGANISM: Artificial Sequence
<220> FEATURE:
<223> OTHER INFORMATION: humanized anti-CD40L light chain

<400> SEQUENCE: 67

Asp Ile Val Leu Thr Gln Ser Pro Ala Thr Leu Ser Val Ser Pro Gly
1               5                   10                  15

Glu Arg Ala Thr Ile Ser Cys Arg Ala Ser Gln Arg Val Ser Ser Ser
            20                  25                  30

Thr Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Phe Ala Thr Tyr Tyr Cys Gln His Ser Trp
                85                  90                  95

Glu Ile Pro Pro Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 68
<211> LENGTH: 229
<212> TYPE: PRT
<213> ORGANISM: Artificial Sequence
<220> FEATURE:
<223> OTHER INFORMATION: hinge +  NTIG Lysine deleted
```

<400> SEQUENCE: 68

Glu Pro Lys Ser Cys Asp Lys Thr His Thr Cys Pro Pro Cys Pro Ser
1 5 10 15

His Thr Gln Pro Leu Gly Val Phe Leu Phe Pro Pro Lys Pro Lys Asp
20 25 30

Gln Leu Met Ile Ser Arg Thr Pro Glu Val Thr Cys Val Val Val Asp
35 40 45

Val Ser Gln Glu Asp Pro Glu Val Gln Phe Asn Trp Tyr Val Asp Gly
50 55 60

Val Glu Val His Asn Ala Lys Thr Lys Pro Arg Glu Glu Gln Phe Asn
65 70 75 80

Ser Thr Tyr Arg Val Val Ser Val Leu Thr Val Leu His Gln Asp Trp
85 90 95

Leu Asn Gly Lys Glu Tyr Lys Cys Lys Val Ser Asn Lys Gly Leu Pro
100 105 110

Ser Ser Ile Glu Lys Thr Ile Ser Lys Ala Lys Gly Gln Pro Arg Glu
115 120 125

Pro Gln Val Tyr Thr Leu Pro Pro Ser Gln Glu Glu Met Thr Lys Asn
130 135 140

Gln Val Ser Leu Thr Cys Leu Val Lys Gly Phe Tyr Pro Ser Asp Ile
145 150 155 160

Ala Val Glu Trp Glu Ser Asn Gly Gln Pro Glu Asn Asn Tyr Lys Thr
165 170 175

Thr Pro Pro Val Leu Asp Ser Asp Gly Ser Phe Phe Leu Tyr Ser Arg
180 185 190

Leu Thr Val Asp Lys Ser Arg Trp Gln Glu Gly Asn Val Phe Ser Cys
195 200 205

Ser Val Leu His Glu Ala Leu His Asn His Tyr Thr Gln Lys Ser Leu
210 215 220

Ser Leu Ser Leu Gly
225

<210> SEQ ID NO 69
<211> LENGTH: 119
<212> TYPE: PRT
<213> ORGANISM: Artificial Sequence
<220> FEATURE:
<223> OTHER INFORMATION: humanized anti-CD40L VL

<400> SEQUENCE: 69

Asp Ile Val Leu Thr Gln Ser Pro Ala Thr Leu Ser Val Ser Pro Gly
1 5 10 15

Glu Arg Ala Thr Ile Ser Cys Arg Ala Ser Gln Arg Val Ser Ser Ser
20 25 30

Thr Tyr Ser Tyr Met His Trp Tyr Gln Gln Lys Pro Gly Gln Pro Pro
35 40 45

Lys Leu Leu Ile Lys Tyr Ala Ser Asn Leu Glu Ser Gly Val Pro Ala
50 55 60

Arg Phe Ser Gly Ser Gly Ser Gly Thr Asp Phe Thr Leu Thr Ile Ser
65 70 75 80

Ser Val Glu Pro Glu Asp Phe Ala Thr Tyr Tyr Cys Gln His Ser Trp
85 90 95

Glu Ile Pro Pro Thr Phe Gly Gly Gly Thr Lys Leu Glu Ile Lys Arg
100 105 110

Thr Val Ala Ala Pro Ser Val

115

<210> SEQ ID NO 70
<211> LENGTH: 118
<212> TYPE: PRT
<213> ORGANISM: Artificial Sequence
<220> FEATURE:
<223> OTHER INFORMATION: humanized anti-CD40L VH

<400> SEQUENCE: 70

Gln Val Gln Leu Val Gln Ser Gly Ala Glu Val Val Lys Pro Gly Ala
1 5 10 15

Ser Val Lys Leu Ser Cys Lys Ala Ser Gly Tyr Ile Phe Thr Ser Tyr
20 25 30

Tyr Met Tyr Trp Val Lys Gln Ala Pro Gly Gln Gly Leu Glu Trp Ile
35 40 45

Gly Glu Ile Asn Pro Ser Asn Gly Asp Thr Asn Phe Asn Glu Lys Phe
50 55 60

Lys Ser Lys Ala Thr Leu Thr Val Asp Lys Ser Ala Ser Thr Ala Tyr
65 70 75 80

Met Glu Leu Ser Ser Leu Arg Ser Glu Asp Thr Ala Val Tyr Tyr Cys
85 90 95

Thr Arg Ser Asp Gly Arg Asn Asp Met Asp Ser Trp Gly Gln Gly Thr
100 105 110

Leu Val Thr Val Ser Ser
115

<210> SEQ ID NO 71
<211> LENGTH: 310
<212> TYPE: PRT
<213> ORGANISM: Artificial Sequence
<220> FEATURE:
<223> OTHER INFORMATION: GLP-1E-NTIG Knob glycan linker

<400> SEQUENCE: 71

His Gly Glu Gly Thr Phe Thr Ser Asp Val Ser Ser Tyr Leu Glu Gly
1 5 10 15

Gln Ala Ala Lys Glu Phe Ile Ala Trp Leu Val Lys Gly Gly Pro Ser
20 25 30

Ser Gly Ala Pro Pro Pro Ser Gly Gly Gly Gly Gly Ser Gly Gly Gly
35 40 45

Gly Ser Gly Gly Gly Gly Ser Ala Lys Asn Thr Thr Ala Pro Ala Thr
50 55 60

Thr Arg Asn Thr Thr Arg Gly Gly Glu Glu Lys Lys Lys Glu Lys Glu
65 70 75 80

Lys Glu Glu Gln Glu Glu Arg Thr His Thr Cys Pro Pro Cys Pro Ser
85 90 95

His Thr Gln Pro Leu Gly Val Phe Leu Phe Pro Pro Lys Pro Lys Asp
100 105 110

Gln Leu Met Ile Ser Arg Thr Pro Glu Val Thr Cys Val Val Val Asp
115 120 125

Val Ser Gln Glu Asp Pro Glu Val Gln Phe Asn Trp Tyr Val Asp Gly
130 135 140

Val Glu Val His Asn Ala Lys Thr Lys Pro Arg Glu Glu Gln Phe Asn
145 150 155 160

Ser Thr Tyr Arg Val Val Ser Val Leu Thr Val Leu His Gln Asp Trp
165 170 175

Leu Asn Gly Lys Glu Tyr Lys Cys Lys Val Ser Asn Lys Gly Leu Pro
180 185 190

Ser Ser Ile Glu Lys Thr Ile Ser Lys Ala Lys Gly Gln Pro Arg Glu
195 200 205

Pro Gln Val Tyr Thr Leu Pro Pro Cys Gln Glu Glu Met Thr Lys Asn
210 215 220

Gln Val Ser Leu Trp Cys Leu Val Lys Gly Phe Tyr Pro Ser Asp Ile
225 230 235 240

Ala Val Glu Trp Glu Ser Asn Gly Gln Pro Glu Asn Asn Tyr Lys Thr
245 250 255

Thr Pro Pro Val Leu Asp Ser Asp Gly Ser Phe Phe Leu Tyr Ser Arg
260 265 270

Leu Thr Val Asp Lys Ser Arg Trp Gln Glu Gly Asn Val Phe Ser Cys
275 280 285

Ser Val Leu His Glu Ala Leu His Asn His Tyr Thr Gln Lys Ser Leu
290 295 300

Ser Leu Ser Leu Gly Lys
305 310

<210> SEQ ID NO 72
<211> LENGTH: 281
<212> TYPE: PRT
<213> ORGANISM: Artificial Sequence
<220> FEATURE:
<223> OTHER INFORMATION: GLP-2-2G-NTIG Hole non-glycan linker

<400> SEQUENCE: 72

His Gly Asp Gly Ser Phe Ser Asp Glu Met Asn Thr Ile Leu Asp Asn
1 5 10 15

Leu Ala Ala Arg Asp Phe Ile Asn Trp Leu Ile Gln Thr Lys Ile Thr
20 25 30

Asp Gly Gly Gly Gly Ser Gly Gly Gly Gly Ser Gly Gly Gly Gly Ser
35 40 45

Glu Lys Glu Lys Glu Glu Gln Glu Glu Arg Thr His Thr Cys Pro Pro
50 55 60

Cys Pro Ser His Thr Gln Pro Leu Gly Val Phe Leu Phe Pro Pro Lys
65 70 75 80

Pro Lys Asp Gln Leu Met Ile Ser Arg Thr Pro Glu Val Thr Cys Val
85 90 95

Val Val Asp Val Ser Gln Glu Asp Pro Glu Val Gln Phe Asn Trp Tyr
100 105 110

Val Asp Gly Val Glu Val His Asn Ala Lys Thr Lys Pro Arg Glu Glu
115 120 125

Gln Phe Asn Ser Thr Tyr Arg Val Val Ser Val Leu Thr Val Leu His
130 135 140

Gln Asp Trp Leu Asn Gly Lys Glu Tyr Lys Cys Lys Val Ser Asn Lys
145 150 155 160

Gly Leu Pro Ser Ser Ile Glu Lys Thr Ile Ser Lys Ala Lys Gly Gln
165 170 175

Pro Arg Glu Pro Gln Val Cys Thr Leu Pro Pro Ser Gln Glu Glu Met
180 185 190

Thr Lys Asn Gln Val Ser Leu Ser Cys Ala Val Lys Gly Phe Tyr Pro
195 200 205

Ser Asp Ile Ala Val Glu Trp Glu Ser Asn Gly Gln Pro Glu Asn Asn
210 215 220

Tyr Lys Thr Thr Pro Pro Val Leu Asp Ser Asp Gly Ser Phe Phe Leu
225 230 235 240

Val Ser Arg Leu Thr Val Asp Lys Ser Arg Trp Gln Glu Gly Asn Val
245 250 255

Phe Ser Cys Ser Val Leu His Glu Ala Leu His Asn His Tyr Thr Gln
260 265 270

Lys Ser Leu Ser Leu Ser Leu Gly Lys
275 280

<210> SEQ ID NO 73
<211> LENGTH: 287
<212> TYPE: PRT
<213> ORGANISM: Artificial Sequence
<220> FEATURE:
<223> OTHER INFORMATION: GLP-1E-NTIG Knob non-glycan linker

<400> SEQUENCE: 73

His Gly Glu Gly Thr Phe Thr Ser Asp Val Ser Ser Tyr Leu Glu Gly
1 5 10 15

Gln Ala Ala Lys Glu Phe Ile Ala Trp Leu Val Lys Gly Gly Pro Ser
20 25 30

Ser Gly Ala Pro Pro Pro Ser Gly Gly Gly Gly Ser Gly Gly Gly Gly
35 40 45

Ser Gly Gly Gly Gly Ser Glu Lys Glu Lys Glu Glu Gln Glu Glu Arg
50 55 60

Thr His Thr Cys Pro Pro Cys Pro Ser His Thr Gln Pro Leu Gly Val
65 70 75 80

Phe Leu Phe Pro Pro Lys Pro Lys Asp Gln Leu Met Ile Ser Arg Thr
85 90 95

Pro Glu Val Thr Cys Val Val Val Asp Val Ser Gln Glu Asp Pro Glu
100 105 110

Val Gln Phe Asn Trp Tyr Val Asp Gly Val Glu Val His Asn Ala Lys
115 120 125

Thr Lys Pro Arg Glu Glu Gln Phe Asn Ser Thr Tyr Arg Val Val Ser
130 135 140

Val Leu Thr Val Leu His Gln Asp Trp Leu Asn Gly Lys Glu Tyr Lys
145 150 155 160

Cys Lys Val Ser Asn Lys Gly Leu Pro Ser Ser Ile Glu Lys Thr Ile
165 170 175

Ser Lys Ala Lys Gly Gln Pro Arg Glu Pro Gln Val Tyr Thr Leu Pro
180 185 190

Pro Cys Gln Glu Glu Met Thr Lys Asn Gln Val Ser Leu Trp Cys Leu
195 200 205

Val Lys Gly Phe Tyr Pro Ser Asp Ile Ala Val Glu Trp Glu Ser Asn
210 215 220

Gly Gln Pro Glu Asn Asn Tyr Lys Thr Thr Pro Pro Val Leu Asp Ser
225 230 235 240

Asp Gly Ser Phe Phe Leu Tyr Ser Arg Leu Thr Val Asp Lys Ser Arg
245 250 255

Trp Gln Glu Gly Asn Val Phe Ser Cys Ser Val Leu His Glu Ala Leu
260 265 270

His Asn His Tyr Thr Gln Lys Ser Leu Ser Leu Ser Leu Gly Lys
275 280 285

<210> SEQ ID NO 74
<211> LENGTH: 314

<212> TYPE: PRT
<213> ORGANISM: Artificial Sequence
<220> FEATURE:
<223> OTHER INFORMATION: IL-13Ralpah2

<400> SEQUENCE: 74

```
Asp Thr Glu Ile Lys Val Asn Pro Pro Gln Asp Phe Glu Ile Val Asp
1               5                   10                  15

Pro Gly Tyr Leu Gly Tyr Leu Tyr Leu Gln Trp Gln Pro Pro Leu Ser
            20                  25                  30

Leu Asp His Phe Lys Glu Cys Thr Val Glu Tyr Glu Leu Lys Tyr Arg
        35                  40                  45

Asn Ile Gly Ser Glu Thr Trp Lys Thr Ile Ile Thr Lys Asn Leu His
    50                  55                  60

Tyr Lys Asp Gly Phe Asp Leu Asn Lys Gly Ile Glu Ala Lys Ile His
65                  70                  75                  80

Thr Leu Leu Pro Trp Gln Cys Thr Asn Gly Ser Glu Val Gln Ser Ser
                85                  90                  95

Trp Ala Glu Thr Thr Tyr Trp Ile Ser Pro Gln Gly Ile Pro Glu Thr
            100                 105                 110

Lys Val Gln Asp Met Asp Cys Val Tyr Tyr Asn Trp Gln Tyr Leu Leu
        115                 120                 125

Cys Ser Trp Lys Pro Gly Ile Gly Val Leu Leu Asp Thr Asn Tyr Asn
    130                 135                 140

Leu Phe Tyr Trp Tyr Glu Gly Leu Asp His Ala Leu Gln Cys Val Asp
145                 150                 155                 160

Tyr Ile Lys Ala Asp Gly Gln Asn Ile Gly Cys Arg Phe Pro Tyr Leu
                165                 170                 175

Glu Ala Ser Asp Tyr Lys Asp Phe Tyr Ile Cys Val Asn Gly Ser Ser
            180                 185                 190

Glu Asn Lys Pro Ile Arg Ser Ser Tyr Phe Thr Phe Gln Leu Gln Asn
        195                 200                 205

Ile Val Lys Pro Leu Pro Pro Val Tyr Leu Thr Phe Thr Arg Glu Ser
    210                 215                 220

Ser Cys Glu Ile Lys Leu Lys Trp Ser Ile Pro Leu Gly Pro Ile Pro
225                 230                 235                 240

Ala Arg Cys Phe Asp Tyr Glu Ile Glu Ile Arg Glu Asp Asp Thr Thr
                245                 250                 255

Leu Val Thr Ala Thr Val Glu Asn Glu Thr Tyr Thr Leu Lys Thr Thr
            260                 265                 270

Asn Glu Thr Arg Gln Leu Cys Phe Val Val Arg Ser Lys Val Asn Ile
        275                 280                 285

Tyr Cys Ser Asp Asp Gly Ile Trp Ser Glu Trp Ser Asp Lys Gln Cys
    290                 295                 300

Trp Glu Gly Glu Asp Leu Ser Lys Lys Thr
305                 310
```

<210> SEQ ID NO 75
<211> LENGTH: 160
<212> TYPE: PRT
<213> ORGANISM: Artificial Sequence
<220> FEATURE:
<223> OTHER INFORMATION: IL-10wt

<400> SEQUENCE: 75

```
Ser Pro Gly Gln Gly Thr Gln Ser Glu Asn Ser Cys Thr His Phe Pro
1               5                   10                  15
```

```
Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160


<210> SEQ ID NO 76
<211> LENGTH: 33
<212> TYPE: PRT
<213> ORGANISM: Artificial Sequence
<220> FEATURE:
<223> OTHER INFORMATION: GLP-2-2(3 points mutated)

<400> SEQUENCE: 76

His Gly Asp Gly Ser Phe Ser Asp Glu Met Asn Thr Ile Leu Asp Gly
1               5                   10                  15

Gln Ala Ala Arg Asp Phe Ile Asn Trp Leu Ile Gln Thr Lys Ile Thr
            20                  25                  30

Asp


<210> SEQ ID NO 77
<211> LENGTH: 103
<212> TYPE: PRT
<213> ORGANISM: Artificial Sequence
<220> FEATURE:
<223> OTHER INFORMATION: IgG1 CH3

<400> SEQUENCE: 77

Glu Pro Gln Val Tyr Thr Leu Pro Pro Ser Arg Asp Glu Leu Thr Lys
1               5                   10                  15

Asn Gln Val Ser Leu Thr Cys Leu Val Lys Gly Phe Tyr Pro Ser Asp
            20                  25                  30

Ile Ala Val Glu Trp Glu Ser Asn Gly Gln Pro Glu Asn Asn Tyr Lys
        35                  40                  45

Thr Thr Pro Pro Val Leu Asp Ser Asp Gly Ser Phe Phe Leu Tyr Ser
    50                  55                  60

Lys Leu Thr Val Asp Lys Ser Arg Trp Gln Gln Gly Asn Val Phe Ser
65                  70                  75                  80

Cys Ser Val Met His Glu Ala Leu His Asn His Tyr Thr Gln Lys Ser
                85                  90                  95

Leu Ser Leu Ser Pro Gly Lys
            100
```

MODIFIED IMMUNOGLOBULIN Fc-FUSION PROTEIN AND USE THEREOF

CROSS-REFERENCE TO RELATED APPLICATION

This application claims priority under the Paris Convention for the Protection of Industrial Property Rights for U.S. Patent Application No. 62/847,470 filed on May 14, 2019, the contents of which are incorporated by reference in their entirety.

BACKGROUND

The present invention relates to a novel modified immunoglobulin Fc fusion protein and use thereof, and more specifically, relates to a novel modified immunoglobulin Fc fusion protein that has an increased half-life and is capable of minimizing side effects, such as ADCC and CDC, which may be caused by antibody Fc fragment; and use thereof.

An immunoglobulin (antibody) Fc domain is widely used as a carrier protein for various therapeutic and diagnostic proteins. An antibody includes two functionally independent moieties, that is, a variable domain that binds to an antigen and is known as "Fab", and a constant domain that is associated with effector functions such as complement activation and attack by a phagocyte and is known as "Fc". Fc has a long serum half-life, and Fab has a short life span (Capon et al., *Nature* 337: 525-531, 1989). When combined with a therapeutic protein or a peptide, the Fc domain can provide a longer half-life, or integrate functions such as the binding of an Fc receptor, the binding of protein A, the fixation of a complement, and the transfer of a placenta. In particular, the longer half-life of such an Fc domain is due to neonatal Fc receptor (hereinafter, referred to as "FcRn") binding affinity.

Many techniques for fusing an Fc domain and a biologically active protein have been developed so far to increase the half-life of the biologically active protein. As a representative example thereof, etanercept (trade name: Enbrel®) that is a fusion protein in which TNFα receptor 2 is linked to the Fc domain of an IgG1 antibody is mentioned (U.S. Pat. No. 5,447,851). In addition to the example, there are also some cytokines and growth hormones fused to the Fc domain of an IgG antibody.

However, unlike the fusion of a cell surface receptor to an extracellular domain, the fusion of a water-soluble protein to IgG causes the reduction in a biological activity compared to a non-fusion cytokine or growth factor. A chimeric protein exists as a dimer, and causes steric hindrance in binding to a target molecule such as a receptor due to the presence of two active proteins close to each other. Therefore, it is necessary to overcome such a problem to produce an efficient Fc fusion protein.

Another limitation of the Fc fusion technique is an unintended immune response. The Fc domain of an immunoglobulin also has effector functions such as antibody-dependent cellular cytotoxicity (ADCC) and complement-dependent cytotoxicity (CDC). In particular, four human IgG isoforms bind, with different affinity, to an activating Fcγ receptor (FcγR including FcγRI, FcγRIIa, and FcγRIIIa), an inhibitory FcγRIIb receptor, and a first factor of a complement (C1q) to cause very different effector functions (Bruhns, P. et al., *Blood* 113(16): 3716-3725, 2009). The binding of IgG to FcγR or C1q depends on residues located in a hinge region and a CH2 domain. However, the effector function of the Fc domain causes apoptosis, cytokine secretion, or inflammation in a subject when a therapeutic protein fused to the Fc domain is administered to the subject in vivo, and thus the effector function is needed to be suppressed to reduce unwanted reactions, unless absolutely necessary.

In order to overcome the above-identified problems, some modified Fc domain proteins have been developed, including those described in US2006/0074225A1, Armour, K. L. et al. (*Eur. J. Immunol.,* 29(8): 2613-2624, 1999), Shields, R. L. et al. (*J. Biol. Chem.* 276(9): 6591-6604, 2001), and Idusogie, E E. et al. (*J. Immunol.* 164(8): 4178-4184, 2000).

In addition, despite the improvement in a half-life, there is still a need to further improve the half-life of a therapeutic protein fused to an Fc domain.

SUMMARY

However, the abovementioned prior arts have the disadvantage of not achieving a satisfactory prolongation level of a half-life or having other side effects.

Therefore, the present invention is to solve the above-mentioned various problems, and an object of the present invention is to provide a novel modified Fc domain protein which does not affect the production and the activity of a bioactive protein while a therapeutic protein fused without effector functions such as ADCC and CDC exhibits a longer half-life. However, such an object is exemplary and does not limit the scope of the present invention.

In accordance with an aspect of the present invention, provided is an immunoglobulin Fc domain variant protein in which $18^{th}$ and $196^{th}$ amino acids of a modified IgG4 Fc domain protein including an amino acid sequence selected from the group consisting of SEQ ID NOs: 1 to 4 are mutated to other amino acids.

In accordance with another aspect of the present invention, provided is a fusion protein in which at least one biologically active protein (API, active pharmaceutical ingredient) is linked to an N-terminus and/or a C-terminus of the immunoglobulin Fc domain variant protein.

In accordance with still another aspect of the present invention, provided is a polynucleotide which encodes the immunoglobulin Fc domain variant protein or the fusion protein.

In accordance with still another aspect of the present invention, provided is a homo- or hetero-dimer which contains the fusion protein.

In accordance with still another aspect of the present invention, provided is a composition which contains, as an active ingredient, the fusion protein, a polynucleotide encoding the fusion protein, or the homo- or hetero-dimer.

In accordance with still another aspect of the present invention, provided is a method for prolonging the half-life in vivo of a biologically active protein, the method including a step for administering, to a subject, a fusion protein obtained by fusing the biologically active protein to the immunoglobulin Fc domain variant protein, or a homo- or hetero-dimer containing the fusion protein.

By the fusion to another biologically active protein, the immunoglobulin Fc domain variant protein according to one exemplary embodiment of the present invention can increase the half-life of the biologically active protein and inactivate antibody Fc domain-dependent effector functions, such as ADCC and CDC which are side effects caused when using an antibody-based protein therapeutic agent. However, the effects of the present invention are not limited thereto.

DETAILED DESCRIPTION OF THE INVENTION

According to an aspect of the present invention, provided is an immunoglobulin Fc domain variant protein in which $18^{th}$ and $196^{th}$ amino acids of a modified IgG4 Fc domain protein including an amino acid sequence selected from the group consisting of SEQ ID NOs: 1 to 4 are mutated to other amino acids.

As used herein, the term “modified IgG4 immunoglobulin Fc domain protein” or “modified IgG4 Fc domain protein” refers to a recombinant antibody Fc domain protein prepared by combining all or part of a hinge, CH2, and CH3, which are constituent elements of an Fc domain of an immunoglobulin, with those derived from different types of antibody molecules, that is, IgG, IgD, IgE, and IgM. As a representative modified IgG4 immunoglobulin Fc domain protein, those disclosed in Korean Patent No. 897938 are mentioned.

As used herein, the term "immunoglobulin Fc domain variant protein" or "Fc domain variant protein" refers to a mutant protein in which at least one amino acid in the modified IgG4 Fc domain protein is substituted, deleted, or added.

In the immunoglobulin Fc domain variant protein, the mutation of the $18^{th}$ amino acid may be a mutation selected from the group consisting of T18N, T18K, and T18Q, the mutation of the $196^{th}$ amino acid may be a mutation selected from the group consisting of M196A, M196F, M196I, M196L, M196V, M196P, and M196W, the mutation of the $18^{th}$ amino acid is more preferably T18Q, and the mutation of the $196^{th}$ amino acid is preferably M196L.

Lysine (K) at a C-terminus of the immunoglobulin Fc domain variant protein may or may not be removed. Whether lysine is removed can be determined according to whether another API is linked to the C-terminus. For example, when API is linked to the C-terminus of the immunoglobulin Fc domain variant protein of the present invention, lysine removal may be advantageous in terms of protein production, and when API is not linked to the C-terminus, it is not necessary to remove lysine.

The immunoglobulin Fc domain variant protein may contain an amino acid sequence selected from the group consisting of SEQ ID NOs: 5 to 9.

According to another aspect of the present invention, provided is a fusion protein in which at least one biologically active protein (API, active pharmaceutical ingredient) is linked to an N-terminus and/or the C-terminus of the immunoglobulin Fc domain variant protein (FIGS. 1 to 4).

As used herein, the term "biologically active protein" is a concept distinguished from structural proteins, which are proteins constituting tissues and organs of a human body, and refers to a protein which performs specific functions such as metabolism and intercellular or intracellular signal transmission that occur in the human body, and can be used for diagnosis and/or treatment of diseases caused by deficiency or excess of the protein.

Figure 1:
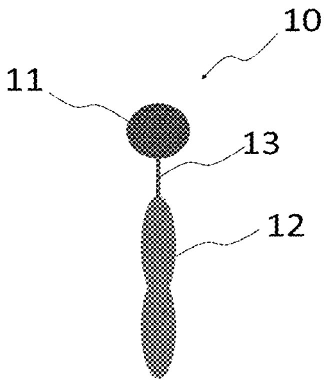
FIGS. 1 to 3 are schematic diagrams showing a structure of a monospecific fusion protein according to one exemplary embodiment of the present invention.
Figure 2:
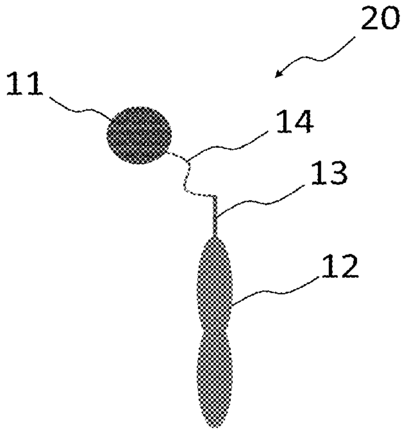
Figure 3:
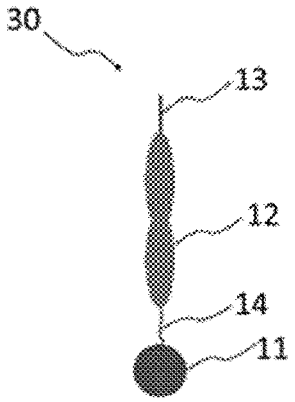

As shown in FIGS. 1 to 4, in fusion proteins (10 to 40) of the present invention, a biologically active protein or an active pharmaceutical ingredient (API, 11) can be linked to an N-terminus or a C-terminus of an immunoglobulin Fc domain variant protein (12) through a hinge region (13) of IgG1 and/or a linker peptide (14) such as a $G_4S$ linker. However, the hinge region (13) is essential for dimerization. When the biologically active protein (11) is directly linked to the hinge region (13) of IgG1, the hinge region (that is, SEQ ID NOs: 20 and 21) can be regarded as a linker as shown in FIG. 3. The hinge region provides flexibility and a dimerization moiety capable of forming an intermolecular disulfide bond through a cysteine residue.

Figure 4A:
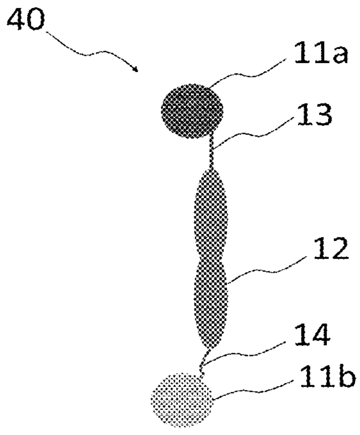
FIG. 4 is a schematic diagram showing a structure of a bispecific fusion protein according to one exemplary embodiment of the present invention.
Figure 4B:
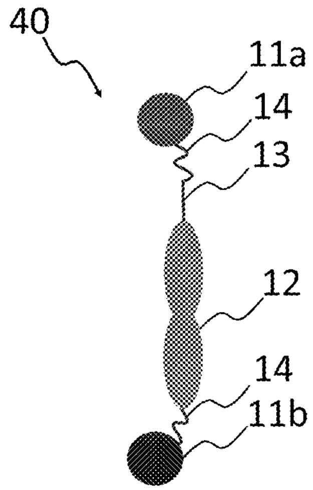

The fusion protein according to one exemplary embodiment of the present invention may contain one or two biologically active proteins. When the fusion protein contains two biologically active proteins, the fusion protein itself exhibits bispecificity (FIG. 4). As shown in FIG. 4*a*, a first biologically active protein (11*a*) is linked to the N-terminus of the immunoglobulin Fc domain variant protein (12) through the hinge region (13) of IgG1, and a second biologically active protein (11*b*) is linked to the C-terminus of the immunoglobulin Fc domain variant protein (12) through the linker peptide (14). In addition, as shown in FIG. 4*b*, the linker peptide (14) such as the $G_4S$ linker is additionally linked to an N-terminus of the hinge region (13) of IgG1, the first biologically active protein (11*a*) is linked to an N-terminus of the linker peptide (14), the second biologically active protein (11*b*) is linked to the C-terminus of the immunoglobulin Fc domain variant protein (12) through the linker peptide (14). In this case, the linker peptide (14) linked to the N-terminus and the linker peptide (14) linked to the C-terminus may have the same sequence, or the linker peptides have the same properties as that of the $G_4S$ linker but may be partially different in terms of specific sequences.

In the fusion protein, the biologically active protein may be a cytokine, an enzyme, a blood coagulation factor, an extracellular domain of a membrane receptor, a growth factor, a peptide hormone, or an antibody mimetic.

In the fusion protein, the length of the linker peptide may be 2 to 60 a.a., 4 to 55 a.a., 5 to 50 a.a., 5 to 46 a.a., 5 to 45 a.a., or 5 to 30 a.a. Among the linker peptides, a linker peptide, which links API to the N-terminus of the immunoglobulin Fc domain variant protein, may include a part or all of a hinge region of a heavy chain of an IgG1 antibody, and a case where the linker peptide includes a part of the hinge region may be a case where an artificial linker peptide is added to an N-terminus or a C-terminus of a part of the hinge region. Furthermore, the hinge region may be a hybrid-type hinge region in which parts of hinge regions of two or more heavy chains of the antibody are mixed. Specifically, the linker peptide may be a combination of one or more selected from the group consisting of GGGGSGGGGSGGGGSEKEKEEQEERTHTCPPCP (SEQ ID NO: 14), RNTGRGGEEKKGSKEKEEQEERETKTPECP (SEQ ID NO: 15), GGGGSGGGGSGGGGSEPKSCDKTHTCPPCP (SEQ ID NO: 16), GSGGGSGTLVTVSSESKYGPPCPPCP (SEQ ID NO: 17), GGGGSGGGGSGGGGSEPKSSDKTHTCPPCP (SEQ ID NO: 18), EPKSSDKTHTCPPCP (SEQ ID NO: 19), EPKSCDKTHTCPPCP (SEQ ID NO: 20), GGGGSGGGGSGGGGSAKNTTAPATTRNTTRGGEEKKKEKEKEEQEERTHTC PPCP (SEQ ID NO: 21), $A(EAAAK)_4ALEA(EAAAK)_4A$ (SEQ ID NO: 22), $(G_4S)_n$ (unit sequence: SEQ ID NO: 23, n is an integer of 1 to 10), $(GSSGGS)_n$ (unit: SEQ ID NO: 24, n is an integer of 1 to 10), SGGGSGGGGSGGGGSGGEEQEEGGS (SEQ ID NO: 25), AAGSGGGGGSGGGGSGGGGS (SEQ ID NO: 26), KESGSVSSEQLAQFRSLD (SEQ ID NO: 27), EGKSSGSGSESKST (SEQ ID NO: 28), GSAGSAAGSGEF (SEQ ID NO: 29), $(EAAAK)_n$ (unit: SEQ ID NO: 30, n is an integer of 1 to 10), CRRRRRREAEAC (SEQ ID NO: 31), GGGGGGGG (SEQ ID NO: 32), GGGGGG (SEQ ID NO: 33), PAPAP (SEQ ID NO: 34), $(Ala\text{-}Pro)_n$ (n is an integer of 1 to 10), VSQTSKLTRAETVFPDV (SEQ ID NO: 35), PLGLWA (SEQ ID NO: 36), TRHRQPRGWE (SEQ ID NO: 37), AGNRVRRSVG (SEQ ID NO: 38), RRRRRRRR (SEQ ID NO: 39), GSSGGSGSSGGSGGGDEADGSRGSQKAGVDE (SEQ ID NO: 40), GGGGSGGGGSGGGGS (SEQ ID NO: 41), AEAAAKEAAAAKA (SEQ ID NO: 42), GFLG (SEQ ID NO: 43), AKATTAPATTRNTGRGGEEKKKEKEKEEQEERETKTPECP (SEQ ID NO: 44), GGSGG (SEQ ID NO: 45), GGSGGSGGS (SEQ ID NO: 46), GGGSGG (SEQ ID NO: 47), and GSTSGSGKPGSGEGS (SEQ ID NO: 48).

In this case, the cytokine may be a chemokine, an interferon, an interleukin, a colony-stimulating factor, or a tumor necrosis factor, the chemokine may be CCL1, CCL2, CCL3, CCL4, CCL5, CCL6, CCL7, CCL8, CCL9, CCL10, CCL11, CCL12, CCL13, CCL14, CCL15, CCL16, CCL17, CCL19, CCL20, CCL21, CCL22, CCL23, CCL24, CCL25, CCL26, CCL27, CCL28, CXCL1, CXCL2, CXCL3, CXCL5, CXCL6, CXCL7, CXCL8, CXCL9, CXCL10, CXCL11, CXCL12, CXCL13, CXCL16, XCL1, XCL2, or CX3CL1, the interferon may be interferon-alpha, interferon-beta, interferon-epsilon, interferon-kappa, interferon-delta, interferon-gamma, interferon-tau, interferon-omega, interferon-nu, or interferon-zeta, the interleukin may be IL-2, IL-4, IL-7, IL-10, IL-12α, IL-12β, IL-13, IL-15 or IL-21, the colony-stimulating factor may be a macrophage colony-stimulating factor (M-CSF), a granulocyte macrophage colony-stimulating factor (GM-CSF), a granulocyte colony-stimulating factor (G-CSF), or promegapoietin, and the tumor necrosis factor may be TNFα, TNFβ, a CD40 ligand (CD40L) a Fas ligand (FasL), a TNF-related apoptosis inducing ligand (TRAIL), or LIGHT (tumor necrosis factor tumor necrosis factor superfamily member 14, TNFSF14).

In the fusion protein, the enzyme may be a tissue-type plasminogen activator (tPA), urokinase, alteplase, reteplase, tenecteplase, streptokinase, anlsteplase, taaphylokinase, nattokinase, limbrokinase, collagenase, glutenase, alglucerase, velaglucerase, imiglucerase, taliglucerase-α, β-glucocerebrosidase, α-galactosiase A, α-glucosiase, α-L-iduroniase, arylsulphatase B, agalsidase, adenosine deaminase, phenylalanine ammonia lyase, dornase, rasburicase, pegloticase, glucarpidase, or ocriplasmin, but is not limited thereto.

In the fusion protein, the blood coagulation factor may be a factor VIII or factor IX.

In the fusion protein, the membrane receptor may be a receptor tyrosine kinase (RTK) superfamily, a T cell receptor, an Fc receptor, a chemokine receptor, a Toll-like receptor family, a guanylyl cyclase-coupled receptor (GCCR), or a receptor serine/threonine kinase, the receptor tyrosine kinase may be an EGFR family, an insulin receptor family, a platelet-derived growth factor receptor (PDGFR) family, a vascular endothelial growth factor receptor (VEGFR) family, a fibroblast growth factor receptor (FGFR) family, a colon cancer kinase (CCK) family, a nerve growth factor receptor (NGFR) family, a hepatocyte growth factor receptor (HGFR) family, an erythropoietin-producing human hepatocyte receptor (EphR) family, a tyrosine-protein kinase receptor (AXL) family, an angiopoietin receptor (TIER) family, a receptor tyrosine kinase-related receptor (RYKR) family, a discoidin domain receptor (DDR) family, a rearranged during transfection (RET) family, a leukocyte receptor tyrosine kinase (LTK) family, a receptor tyrosine kinase-like orphan receptors (ROR) family, a muscle-specific kinase (MuSK) family, CD80 (B7.1), or CD83, the Fc receptor may be an Fc gamma receptor, an Fc alpha receptor, or an Fc epsilon receptor, the cytokine receptor may be a type 1 cytokine receptor, a type 2 cytokine receptor, a tumor necrosis factor receptor family, a chemokine receptor, or a TGF-beta receptor family, the Toll-like receptor family may be TLR1, TLR2, TLR3, TLR4, TLR5, TLR6, TLR7, TLR8, TLR9, TLR10, TLR11, TLR12, or TLR13, the guanylyl cyclase-coupled receptor may be natriuretic factor receptor 1 (NPR1), NPR2, or NPR3, and the receptor serine/threonine kinase may be a TGF-β superfamily receptor, a bone morphogenetic protein (BMP) receptor, or an activin receptor-like kinase (ALK).

In the fusion protein, the growth factor may be adrenomedullin, angiopoietin, a bone morphogenetic protein, a ciliary neurotrophic factor, a leukemia inhibitory factor, an epidermal growth factor (EGF), ephrin, erythropoietin (EPO), fibroblast growth factor (FGF), a glial cell line-derived neurotrophic factor (GDNF) family, growth differentiation factor-9 (GDF9), a hepatocyte growth factor (HGF), a hepatoma-derived growth factor (HDGF), insulin, an insulin-like growth factor (IGF), a keratinocyte growth factor (KGF), a migration-stimulating factor (MSF), a macrophage-stimulating factor, neuregulin, neurotrophin, a placental growth factor (PGF), a platelet-derived growth factor (PDGF), a T-cell growth factor (TCGF), thrombopoietin (TPO), a transforming growth factor (TGF) family, or a vascular endothelial growth factor (VEGF).

In the fusion protein, the peptide hormone may be a human growth hormone (hGH), a GLP-1 analog, a GLP-2 analog, insulin, an adrenocorticotropic hormone, amylin, angiotensin, neuropeptide Y, enkephalin, neurotensin, an atrial natriuretic peptide, calcitonin, choloecystokinin, gastrin, ghelin, glucagon, a follicle-stimulating hormone, leptin, a melanocyte-stimulating hormone (MSH), oxytocin, a parathyroid hormone, prolactin, renin, somatostatin, a thyroid-stimulating hormone (TSH), a thyrotropin-releasing hormone (TRH), vasopressin, or a vasoactive intestinal peptide.

In the fusion protein, the antibody mimetic may be scFv, $V_{NAR}$, $V_{H}$H, affibody, affilin, affimer, affitin, alphabody, anticalin, avimer, DARPin, Fynomer, a Kunitz domain peptide, a monobody, a repebody, VLR, or nanoCLAMP.

In the fusion protein, the IL-10 protein may be an IL 10 variant protein in which isoleucine, which is the $87^{th}$ amino acid, is substituted with alanine, or a monomeric IL-10 variant protein in which a linker peptide having a length of 6 to 10 a.a. is inserted between asparagine, which is the $134^{th}$ amino acid, and lysine, which is the $135^{th}$ amino acid, and may include the amino acid sequence set forth in SEQ ID NO: 54 or 56.

As used herein, the term "fusion protein" refers to a recombinant protein in which two or more proteins or domains responsible for specific functions in a protein are linked such that each protein or domain is responsible for an original function thereof. A linker peptide having a flexible structure can be generally inserted between the two or more proteins or domains. As the linker peptide, GGGGSGGGGSGGGGSEKEKEEQEERTHTCPPCP (SEQ ID NO: 14), RNTGRGGEEKKGSKEKEEQEERETKTPECP (SEQ ID NO: 15), GGGGSGGGGSGGGGSEPKSCDKTHTCPPCP (SEQ ID NO: 16), GSGGGSGTLVTVSSESKYGPPCPPCP (SEQ ID NO: 17), GGGGSGGGGSGGGGSEPKSSDKTHTCPPCP (SEQ ID NO: 18), EPKSSDKTHTCPPCP (SEQ ID NO: 19), EPKSCDKTHTCPPCP (SEQ ID NO: 20), GGGGSGGGGSGGGGSAKNTTAPATTRNTTRGGEEKKKEKEKEEQEERTHTC PPCP (SEQ ID NO: 21), $A(EAAAK)_4ALEA(EAAAK)_4A$ (SEQ ID NO: 22), $(G_4S)_n$ (unit sequence: SEQ ID NO: 23, n is an integer of 1 to 10), $(GSSGGS)_n$ (unit: SEQ ID NO: 24, n is an integer of 1 to 10), SGGGSGGGGSGGGGSGGEEQEEGGS (SEQ ID NO: 25), AAGSGGGGGSGGGGSGGGGS (SEQ ID NO: 26), KESGSVSSEQLAQFRSLD (SEQ ID NO: 27), EGKSSGSGSESKST (SEQ ID NO: 28), GSAGSAAGSGEF (SEQ ID NO: 29), $(EAAAK)_n$ (unit: SEQ ID NO: 30, n is an integer of 1 to 10), CRRRRRREAEAC (SEQ ID NO: 31), GGGGGGGG (SEQ ID NO: 32), GGGGGG (SEQ ID NO: 33), PAPAP (SEQ ID NO: 34), $(Ala-Pro)_n$ (n is an integer of 1 to 10), VSQTSKLTRAETVFPDV (SEQ ID NO: 35), PLGLWA (SEQ ID NO: 36), TRHRQPRGWE (SEQ ID NO: 37), AGNRVRRSVG (SEQ ID NO: 38), RRRRRRRR (SEQ ID NO: 39), GSSGGSGSSGGSGGGDEADGSRGSQKAGVDE (SEQ ID NO: 40), GGGGSGGGGSGGGGS (SEQ ID NO: 41), AEAAAKEAAAAKA (SEQ ID NO: 42), GFLG (SEQ ID NO: 43), AKATTAPATTRNTGRGGEEKKKEKEKEEQEERETKTPECP (SEQ ID NO: 44), GGSGG (SEQ ID NO: 45), GGSGGSGGS (SEQ ID NO: 46), GGGSGG (SEQ ID NO: 47), and GSTSGSGKPGSGEGS (SEQ ID NO: 48) may be memtioned.

As used herein, the term "antibody" refers to an immunoglobulin molecule which is a heterotetrameric protein produced by binding two identical heavy chains and two identical light chains, and performs antigen-specific binding through an antigen-binding site composed of a variable region ($V_L$) of the light chain and a variable region ($V_H$) of the heavy chain, thereby causing an antigen-specific humoral immune response. As the antibody, depending on the origin thereof, IgA, IgG, IgD, IgE, IgM, IgY, or the like is mentioned.

As used herein, the term "antigen-binding fragment of an antibody" refers to a fragment which has antigen-binding ability derived from an antibody and includes both a fragment produced by cleaving an antibody with a protein cleaving enzyme as well as a single-chain fragment produced in a recombinant manner, and examples thereof include Fab, $F(ab')_2$, scFv, diabody, triabody, sdAb, or $V_H$H.

As used herein, the term "Fab" refers to an antigen-binding antibody fragment (fragment antigen-binding) which is produced by cleaving an antibody molecule with papain, which is a proteinase and is a dimer of two peptides of $V_H$-CH1 and $V_L$-$C_L$, and the other fragment produced by the papain is referred to as Fc (fragment crystallizable).

As used herein, the term "$F(ab')_2$" refers to a fragment that includes an antigen-binding site among fragments produced by cleaving an antibody with pepsin, which is a proteinase, and is in a form of a tetramer in which the two Fab's are linked by a disulfide bond. The other fragment produced by the pepsin is referred to as pFc'.

As used herein, the term "Fab" refers to a molecule having a similar structure to that of Fab produced by separating the abovementioned $F(ab')_2$ under weak reducing conditions.

As used herein, the term "scFv" is an abbreviation for a "single chain variable fragment", and refers to a fragment which is not a fragment of an actual antibody, but is a kind of fusion protein prepared by linking the heavy-chain variable region ($V_H$) to the light-chain variable region ($V_L$) of the antibody through a linker peptide having a size of about 25 a.a., and is known to have antigen-binding ability even though the fragment is not a unique antibody fragment (Glockshuber et al., *Biochem.* 29(6): 1362-1367, 1990).

As used herein, the terms "diabody" and "triabody" refer to antibody fragments in a form of two and three scFv's linked by a linker, respectively.

As used herein, the term "single domain antibody (sdAb)" refers to an antibody fragment which is also referred to as a nanobody and consists of a single variable region fragment of an antibody. The sdAb derived from the heavy chain is mainly used, but a single variable region fragment derived from the light chain is also reported to specifically bind to an antigen. $V_{NAR}$ composed of variable region fragments of a shark antibody and $V_H$H composed of variable region fragments of a camelid antibody, which consist only of dimers of single chains unlike conventional antibodies composed of a heavy chain and a light chain, are also included in sdAb.

As used herein, the term "antibody mimetic" is a concept including a protein having similar functions to those of antibodies prepared from non-antibody-derived protein scaffolds such as a monobody and a variable lymphocyte receptor (VLR), that is, having antigen-binding ability, unlike a normal full-length antibody in which two heavy chains and two light chains form a quaternary structure of a heterotetramer to exhibit functions. Examples of such an antibody mimetic include Affibody derived from a Z domain of protein A (Nygren, P. A., *FEBS J.* 275(11): 2668 to 2676, 2008), Affilin derived from Gamma-B crystallin or Ubiquitin (Ebersbach et al., *J. Mol. Biol.* 372(1): 172-185, 2007), Affimer derived from Cystatin (Johnson et al., *Anal. Chem.* 84(15): 6553-6560, 2012), Affitin derived from Sac7d (Krehenbrink et al., *J. Mol. Biol.* 383 (5): 1058-1068, 2008), Alphabody derived from a triple helix coiled coil protein (Desmet et al., *Nat. Commun.* 5: 5237, 2014), Anticalin derived from lipocalin (Skerra et al., *FEBS J.* 275(11): 2677-2683, 2008), Avimer derived from domains of various membrane receptors (Silverman et al., *Nat. Biotechnol.* 23(12): 1556-1561, 2005), DARPin derived from Ankyrin repeat motif (Stumpp et al., *Drug Discov. Today.* 13(15-16): 695-701, 2008), Fynomer derived from a SH3 domain of a Fyn protein (Grabulovski et al., *J. Biol. Chem.* 282(5): 3196-3204, 2007), Kunitz domain peptides derived from Kunitz domains of various protein inhibitors (Nixon and Wood, *Curr. Opin. Drug Discov. Dev.* 9(2): 261-268, 2006), a monobody derived from the 10th type 3 domain of fibronectin (Koide and Koide, *Methods Mol. Biol.* 352: 95-109, 2007), nanoCLAMP derived from carbohydrate-binding module 32-2 (Suderman et al., *Protein Exp. Purif* 134: 114-124, 2017), a variable lymphocyte receptor (VLR) derived from a hagfish (Boehm et al., *Ann. Rev. Immunol.* 30: 203-220, 2012), and a repebody engineered to enhance antigen affinity based on the VLR (Lee et al., *Proc. Natl. Acad. Sci. USA,* 109: 3299-3304, 2012).

According to still another aspect of the present invention, provided is a polynucleotide which encodes the immunoglobulin Fc domain variant protein or the fusion protein.

The polynucleotide may be any polynucleotide as long as the polynucleotide is a polynucleotide encoding a protein containing an amino acid sequence selected from the group consisting of SEQ ID NOs: 5 to 9, and may have a codon optimized for the type of host cell used to produce the protein. Such a technique for optimizing a codon according to a host cell is well known in the art (Fuglsang et al., *Protein Expr. Purif* 31(2): 247-249, 2003). The polynucleotide more preferably contains a nucleic acid sequence selected from the group consisting of SEQ ID NOs: 10 to 13.

According to still another aspect of the present invention, provided is a recombinant vector containing the polynucleotide.

In the recombinant vector, the polynucleotide may be contained in a form of a gene construct operably linked to a regulatory sequence.

As used herein, the term "operably linked to" means that a target nucleic acid sequence (for example, in vitro transcription/translation system or in a host cell) is linked to the regulatory sequence in such a way that the target nucleic acid sequence can be expressed.

As used herein, the term "regulatory sequence" is meant to include a promoter, an enhancer, and other regulatory elements (for example, polyadenylation signal). Examples of the regulatory sequence include a sequence which directs such that a target nucleic acid is constantly expressed in many host cells, a sequence (for example, a tissue-specific regulatory sequence) which directs such that a target nucleic acid is expressed only in a specific tissue cell, and a sequence (for example, an inducible regulatory sequence) which directs such that expression is induced by a specific signal. Those skilled in the art could understand that the design of an expression vector may vary depending on factors such as the selection of a host cell to be transformed and the desired level of protein expression. The expression vector of the present invention can be introduced into a host cell to express the fusion protein. Regulatory sequences which enable expression in the eukaryotic cell and the prokaryotic cell are well known to those skilled in the art. As described above, these regulatory sequences generally include regulatory sequences responsible for transcription initiation, and optionally, a poly-A signal responsible for transcription termination and stabilization of a transcript. Additional regulatory sequences may include a translation enhancing factor and/or a naturally-combined or heterologous promoter region, in addition to the transcription regulatory factor. For example, possible regulatory sequences which enable expression in a mammalian host cell include a CMV-HSV thymidine kinase promoter, SV40, an RSV-promoter (Rous sarcoma virus), a human kidney urea 1α-promoter, a glucocorticoid-inducing MMTV-promoter (Moloney mouse tumor virus), a metallothionein- or tetracycline-inducible promoter, or an amplifying agent such as a CMV amplifying agent and an SV40 amplifying agent. It is considered that for expression in a nerve cell, a neurofilament-promoter, a PGDF-promoter, an NSE-promoter, a PrP-promoter, or a thy-1-promoter can be used. The above-mentioned promoters are known in the art, and are described in the literature (Charron, *J. Biol. Chem.* 270: 25739 to 25745, 1995). For the expression in the prokaryotic cell, a number of promoters, including a lac-promoter, a tac-promoter, or a trp promoter, have been disclosed. In addition to the factors capable of initiating transcription, the regulatory sequences may include a transcription termination signal, such as an SV40-poly-A site and a TK-poly-A site, on the downstream of the polynucleotide according to one exemplary embodiment of the present invention. In the present specification, suitable expression vectors are known in the art, and examples thereof include Okayama-Berg cDNA expression vector pcDV1 (Parmacia), pRc/CMV, pcDNA1, pcDNA3 (Invitrogene), pSPORT1 (GIBCO BRL), pGX-27 (Korean Patent No. 1442254), pX (Pagano et al., *Science* 255: 1144-1147, 1992), a yeast two-hybrid vector such as pEG202 and dpJG4-5 (Gyuris et al., *Cell* 75: 791-803, 1995), and a prokaryotic expression vector such as lambda gt11 and pGEX (Amersham Pharmacia). The vector may further include a polynucleotide encoding a secretion signal, in addition to the nucleic acid molecules of the present invention. The secretion signals are well known to those skilled in the art. Moreover, depending on the used expression system, a leader sequence which can lead the fusion protein according to one exemplary embodiment of the present invention to a cellular compartment is combined with a coding sequence of the polynucleotide according to one exemplary embodiment of the present invention, and is preferably a leader sequence capable of directly secreting a decoded protein or the protein thereof into a pericytoplasmic or extracellular medium.

In addition, the vector of the present invention can be prepared, for example, by a standard recombinant DNA technique, and examples of the standard recombinant DNA technique include ligation of a smooth terminus and an adhesion terminus, a restriction enzyme treatment to provide a proper terminus, removal of a phosphate group by an alkaline phosphatase treatment to prevent inappropriate binding, and enzymatic linkage by T4 DNA ligase. The vector of the present invention can be prepared by recombining DNA encoding a signal peptide obtained by chemical synthesis or a genetic recombination technique, the immunoglobulin Fc domain variant protein according to one exemplary embodiment of the present invention, or DNA encoding a fusion protein containing the same with a vector containing an appropriate regulatory sequence. The vector containing a regulatory sequence can be commercially purchased or prepared, and in one exemplary embodiment of the present invention, a pBispecific backbone vector (Genexine, Inc., Korea), a pAD15 vector, pGP30 (Genexine, Inc. Korea), or a pN293F vector (Y-Biologics, Inc., Korea) was used as a skeleton vector.

The expression vector may further include a polynucleotide encoding a secretion signal sequence, and the secretion signal sequence induces the extracellular secretion of the recombinant protein expressed in the cell, and may be a tissue plasminogen activator (tPA) signal sequence, a herpes simplex virus glycoprotein Ds (HSV gDs) signal sequence, or a growth hormone signal sequence.

The expression vector according to one exemplary embodiment of the present invention may be an expression vector capable of expressing the protein in a host cell, and the expression vector may be in any form such as a plasmid vector, a viral vector, a cosmid vector, a phagemid vector, or an artificial human chromosome.

According to still another aspect of the present invention, provided is a homo- or hetero-dimer which contains the fusion protein.

Figure 5:
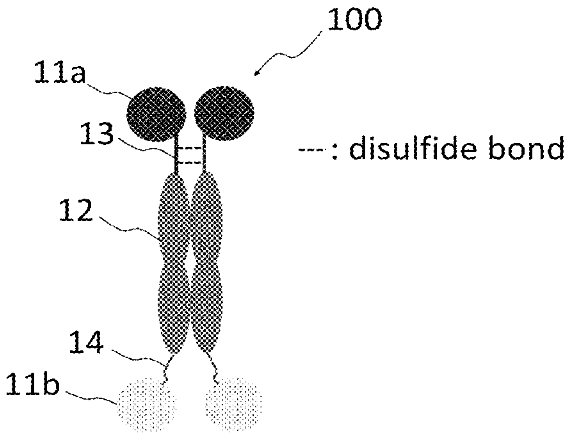
FIG. 5 is a schematic diagram showing a structure of a homodimer composed of the bispecific fusion proteins according to one exemplary embodiment of the present invention.
Figure 6:
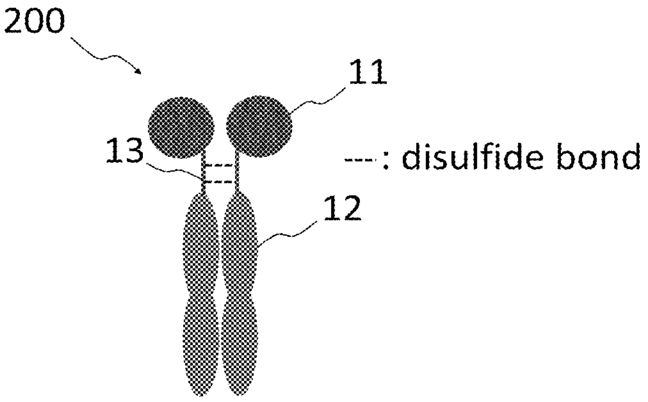
FIG. 6 is a schematic diagram showing a structure of a homodimer of the monospecific fusion proteins according to one exemplary embodiment of the present invention.
Figure 7:
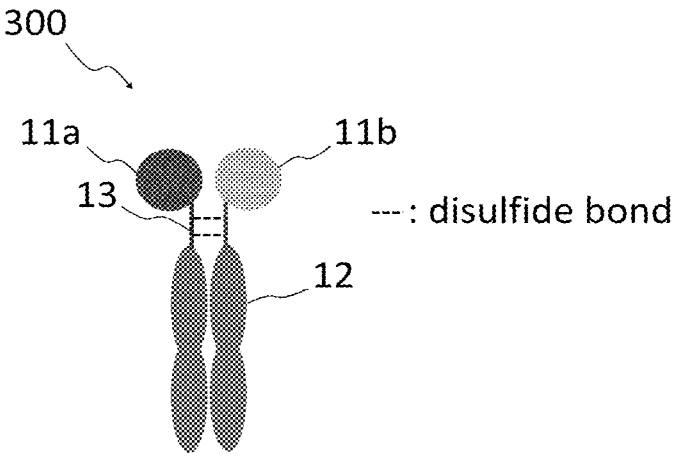
FIG. 7 is a schematic diagram showing a structure of a heterodimer of two different monospecific fusion proteins according to one exemplary embodiment of the present invention.
Figure 8:
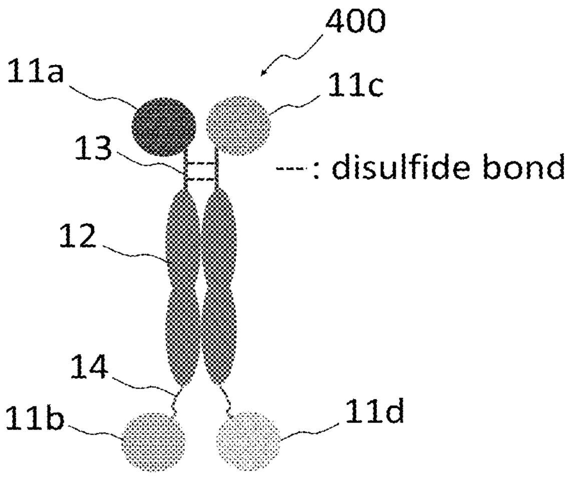
FIG. 8 is a schematic diagram showing a structure of a heterodimer composed of two different bispecific fusion proteins according to one exemplary embodiment of the present invention.
Figure 9:
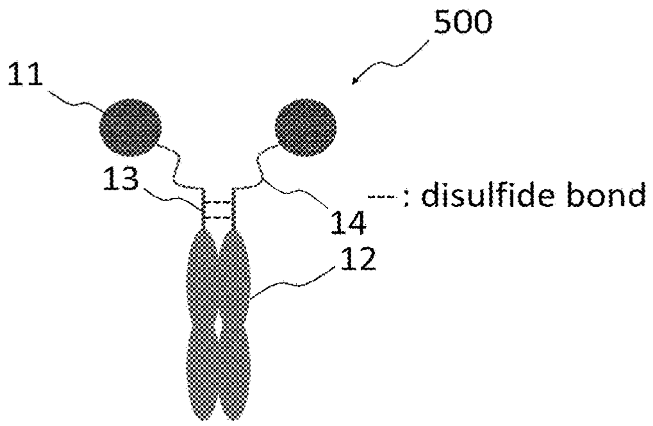
FIG. 9 is a schematic diagram showing a structure of a homodimer of monospecific fusion proteins, which have a hinge region of IgG1 and a linker peptide, according to one exemplary embodiment of the present invention.
Figure 10:
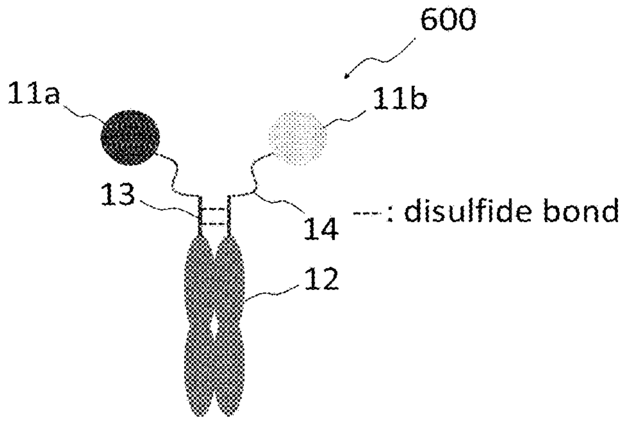
FIG. 10 is a schematic diagram showing a structure of a heterodimer composed of two different monospecific fusion proteins according to one exemplary embodiment of the present invention.
Figure 11:
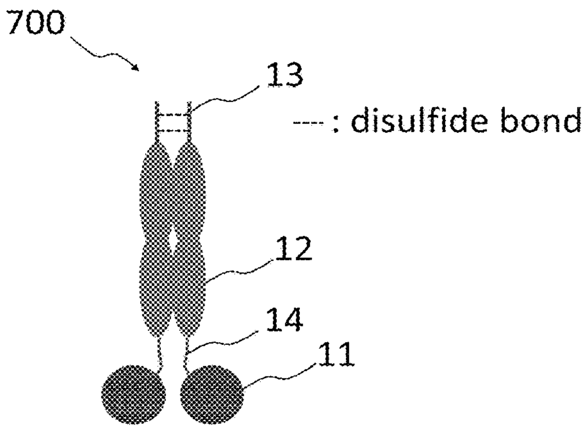
FIG. 11 is a schematic diagram showing a structure of a homodimer of monospecific fusion proteins, which have a biologically active protein at a C-terminus, according to one exemplary embodiment of the present invention.
Figure 12:
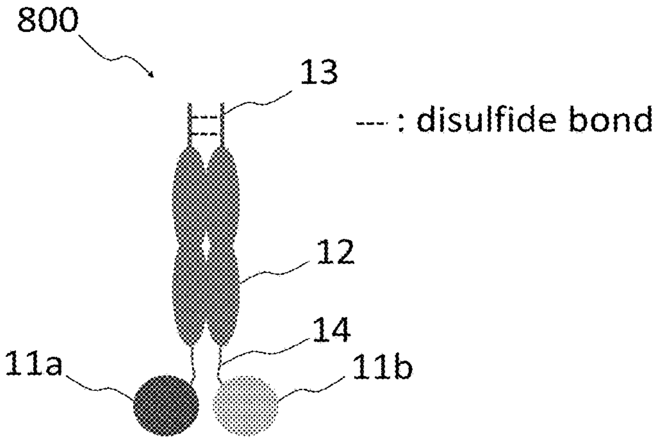
FIG. 12 is a schematic diagram showing a structure of a heterodimer composed of two different bispecific fusion proteins, which have a biologically active protein at a C-terminus, according to one exemplary embodiment of the present invention.

In the homodimer, as shown in FIG. 5, when the different biologically active proteins (11*a* and 11*b*) are respectively linked to the N-terminus and the C-terminus of the immunoglobulin Fc domain variant protein (12), a prepared homodimer (100) exhibits bispecificity. However, as shown in FIG. 6, when only one monospecific fusion protein containing the biologically active protein (11) is dimerized, a produced homodimer (200) still exhibits monospecificity (FIG. 6). In a case of the heterodimer, as shown in FIG. 7, when two different monospecific fusion proteins respectively containing the biologically active proteins (11*a* and 11*b*) are dimerized, a prepared heterodimer (300) exhibits bispecificity. As shown in FIG. 8, when two different bispecific fusion proteins each containing two different biologically active proteins (11*a*, 11*b*, 11*c*, and 11*d*) are dimerized, a produced heterodimer (400) exhibits tetraspecificity.

Optionally, the homo- or hetero-dimers (500, 600, 700, and 800) according to one exemplary embodiment of the present invention may contain one or more linker peptides (14) between the biologically active proteins (11, 11*a*, 11*b*, 11*c*, and 11*d*) and the hinge region (13) or between the region of the immunoglobulin Fc domain variant protein (12) and the biologically active proteins. These fusion partners may be linked to the N-terminus or the C-terminus of the immunoglobulin Fc domain variant protein through the linker peptides (14) (FIGS. 9 to 12).

In particular, the biologically active protein (11*a*) linked to the N-terminus of the fusion protein may be a ligand which acts as a target moiety, and the other biologically active protein (11*b*) linked to the C-terminus of the same fusion protein may be a functional protein having a desired biological activity (FIGS. 5 and 8). Conversely, the functional protein may be linked to the N-terminus, and the ligand may be linked to the C-terminus. These bispecific fusion proteins can form a homodimer by an intermolecular disulfide bond through a cysteine residue present in the hinge region (13), and a selective hydrophobic interaction between immunoglobulin Fc domain variant proteins can promote dimerization. Two different bispecific fusion proteins can form a heterodimer. In this way, the homo- or hetero-dimer proteins according to one exemplary embodiment of the present invention may contain one to four biologically active proteins, and more types of proteins may be added by adding a linker peptide to the bioactive protein present at each terminus.

When the heterodimer according to one exemplary embodiment of the present invention is intended to be prepared, in order to minimize the formation of the homodimer, a knobs-into-holes (KIH) technique, which is well known in the art, can be used.

As used herein, the term "knobs-into-holes (KIH)" refers to one design strategy in antibody engineering used for heterodimerization of heavy chains in the production of the bispecific IgG antibody. In the KIH technique, when two fusion proteins forming a heterodimer are divided into a first fusion protein and a second fusion protein, in the modified IgG4 Fc region of the first fusion protein, serine, which is the $10^{th}$ amino acid of a CH3 domain, may be substituted with cysteine (C), and threonine (T), which is the $22^{nd}$ amino acid, may be substituted with tryptophan (W) (knobs structure), and in the Fc region of the second fusion protein, tyrosine (Y), which is the $5^{th}$ amino acid of a CH3 domain, may be substituted with cysteine (C), threonine (T), which is the $22^{nd}$ amino acid, may be substituted with serine (S), leucine (L), which is the $24^{th}$ amino acid, may be substituted with alanine (A), and tyrosine (Y), which is the $63^{rd}$ amino acid, may be substituted with valine (V) (holes structure). Conversely, in the Fc region of the first fusion protein, tyrosine (Y), which is the $5^{th}$ amino acid of the CH3 domain, may be substituted with cysteine (C), threonine (T), which is the $22^{nd}$ amino acid, may be substituted with serine (S), leucine (L), which is the $24^{th}$ amino acid, may be substituted with alanine (A), and tyrosine (Y), which is the $63^{rd}$ amino acid, may be substituted with valine (V) (holes structure), and in the modified IgG4 Fc region of the second fusion protein, serine (S), which is the $10^{th}$ amino acid of the CH3 domain, may be substituted with cysteine (C), and threonine (T), which is the $22^{nd}$ amino acid, may be substituted with tryptophan (W) (knobs structure).

In this case, the position of the amino acid where the mutation occurred is based on a reference sequence (amino acid sequence of the human IgG1 CH3 domain of SEQ ID NO: 77). Even when additional mutations such as addition, deletion, or substitution of amino acids occur at a site independent of the knobs-into-holes structure on the CH domain, a fusion protein in which an amino acid corresponding to the position of the site is mutated based on the reference sequence may be used. Optionally, the knobs-into-holes structure can be introduced through other amino acid mutations well known in the art. Such a mutation is specifically described in the prior literature (Wei et al., *Oncotarget* 8(31): 51037-51049, 2017; Ridgway et al., *Protein Eng.* 9(7): 617-621, 1996; Carter, P., *J. Immunol. Methods* 48(1-2): 7-15, 2001; Merchant et al., *Nat. Biotechnol.* 16(7): 677-681, 1998). A bispecific dimer fusion protein can be produced through such a selective mutation, for example, a combination of a knob structure in which threonine, which is the $22^{nd}$ amino acid of the CH3 domain of the first fusion protein, is substituted with tyrosine and a hole structure in which tyrosine, which is the $63^{rd}$ amino acid of the CH3 domain of the second fusion protein, is substituted with threonine. Conversely, the knobs-into-holes structure may be formed by introducing a hole structure to the first fusion protein and introducing a knob structure to the second fusion protein.

According to still another aspect of the present invention, provided is a composition which contains, as an active ingredient, the fusion protein, a polynucleotide encoding the fusion protein, or the homo- or hetero-dimer.

According to still another aspect of the present invention, provided is a method for prolonging the half-life in vivo of a biologically active protein, the method including a step for administering, to a subject, a fusion protein obtained by fusing the biologically active protein to the immunoglobulin Fc domain variant protein, or a homo- or hetero-dimer containing the fusion protein.

According to still another aspect of the present invention, provided is a composition which contains, as an active ingredient, a fusion protein obtained by fusing the biologically active protein to the immunoglobulin Fc domain variant protein, or a homo- or hetero-dimer containing the fusion protein.

The composition may contain a pharmaceutically acceptable carrier, and may further include a pharmaceutically acceptable adjuvant, excipient, or diluent in addition to the carrier.

As used herein, the term "pharmaceutically acceptable" refers to a composition which is physiologically acceptable and generally does not cause an allergic reaction, such as a gastrointestinal disorder and dizziness, or a similar reaction when administered to a human. Examples of the carrier, the excipient, and the diluent include lactose, dextrose, sucrose, sorbitol, mannitol, xylitol, erythritol, maltitol, starch, acacia rubber, alginate, gelatin, calcium phosphate, calcium silicate, cellulose, methyl cellulose, polyvinylpyrrolidone, water, methylhydroxybenzoate, propylhydroxybenzoate, talc, magnesium stearate, and mineral oil. Moreover, a filler, an anti-aggregation agent, a lubricant, a wetting agent, a fragrance, an emulsifier, and an antiseptic agent may be further contained.

Furthermore, when the pharmaceutical composition according to one exemplary embodiment of the present invention is administered to a mammal, the pharmaceutical composition can be formulated using methods known in the art to allow rapid, sustained, or delayed release of the active ingredient. Examples of the formulation include powder, a granule, a tablet, an emulsion, a syrup, an aerosol, a soft or hard gelatin capsule, a sterile injectable solution, and a sterile powder form.

The composition according to one exemplary embodiment of the present invention can be administered by various routes such as oral administration and parenteral administration, for example, suppository, transdermal, intravenous, intraperitoneal, intramuscular, intralesional, nasal, or intravertebral administration, and can be administered using an implantation device for sustained release or continuous or repeated release. The administration can be performed once or several times a day within a desired range, and can be performed at an interval such as once a week, twice a week, and once a month, and the duration of administration is also not particularly limited.

The composition according to one exemplary embodiment of the present invention can be formulated in a suitable form with a pharmaceutically acceptable carrier that is commonly used. Examples of the pharmaceutically acceptable carrier include carriers for parenteral administration such as water, suitable oil, a saline solution, aqueous glucose, and glycol, and a stabilizer and a preservative may be further contained. Examples of the suitable stabilizer include antioxidants such as sodium hydrogen sulfite, sodium sulfite, or ascorbic acid. Examples of the suitable preservative include benzalkonium chloride, methyl- or propyl-paraben, and chlorobutanol. Moreover, the composition according to the present invention may suitably contain a suspending agent, a solubilizer, a stabilizer, an isotonic agent, a preservative, an adsorption inhibitor, a surfactant, a diluent, an excipient, a pH adjuster, a painless agent, a buffer agent, an antioxidant, or the like if necessary, depending on the administration method or the formulation. The pharmaceutically acceptable carriers and formulations suitable for the present invention, including those exemplified above, are described in detail in the literature [Remington's Pharmaceutical Sciences, latest edition].

The dosage of the composition to a patient depends on many factors including a height of the patient, a body surface area, an age, a specific compound administered, a gender, a time and a route of administration, general health, and other drugs administered simultaneously. The pharmaceutically active protein can be administered in an amount of 100 ng/body weight (kg) to 10 mg/body weight (kg), more preferably 1 to 500 μg/kg (body weight), and most preferably 5 to 50 μg/kg (body weight), but the dosage can be adjusted in consideration of the abovementioned factors.

According to still another aspect of the present invention, provided is a method for treating a disease of a subject, the method including a step for administering, to the subject in a therapeutically effective amount, a fusion protein obtained by fusing a biologically active protein to the immunoglobulin Fc domain variant protein, or a homo- or a hetero-dimer which contains the fusion protein.

As used herein, the term "therapeutically effective amount" refers to an amount sufficient to treat the disease at a reasonable benefit/risk ratio applicable to medical treatment, and an effective dose level can be determined according to factors including the type of subject, severity, an age, a gender, a drug activity, drug sensitivity, an administration time, an administration route, a rate of excretion, a treatment duration, drugs used simultaneously, and other factors well known in the medical field. The therapeutically effective amount of the composition according to the present invention is 0.1 mg/kg to 1 g/kg and more preferably 1 mg/kg to 500 mg/kg, but the effective dosage can be appropriately adjusted according to the age, the gender, and the condition of the patient.

The abovementioned disease is a disease requiring administration of the biologically active protein, for example, when the biologically active protein is a GLP-1 analog, the disease to be treated may be diabetes or metabolic syndrome, when the biologically active protein is a GLP-2 analog, the disease to be treated may be short bowel syndrome or an inflammatory bowel disease, when the biologically active protein is IL-2, the disease to be treated may be a malignant tumor, when the biologically active protein is FcεRIa, the disease to be treated may be IgE-mediated allergic diseases such as asthma and atopic dermatitis, and when the biologically active protein is an anti-CD40L antibody mimetic, the disease to be treated may be an autoimmune disease or an organ transplant rejection reaction.

Hereinafter, the present invention will be described in more detail through Examples and Experimental Examples. However, the present invention is not limited to Examples and Experimental Examples described below, and may be implemented in various other forms, and Examples and Experimental Examples described below are provided to enable the disclosure of the present invention to be complete and to fully convey the scope of the invention to those skilled in the art to which the present invention belongs.

Example 1: Design of Immunoglobulin Fc Domain Variant Protein

Figure 13:
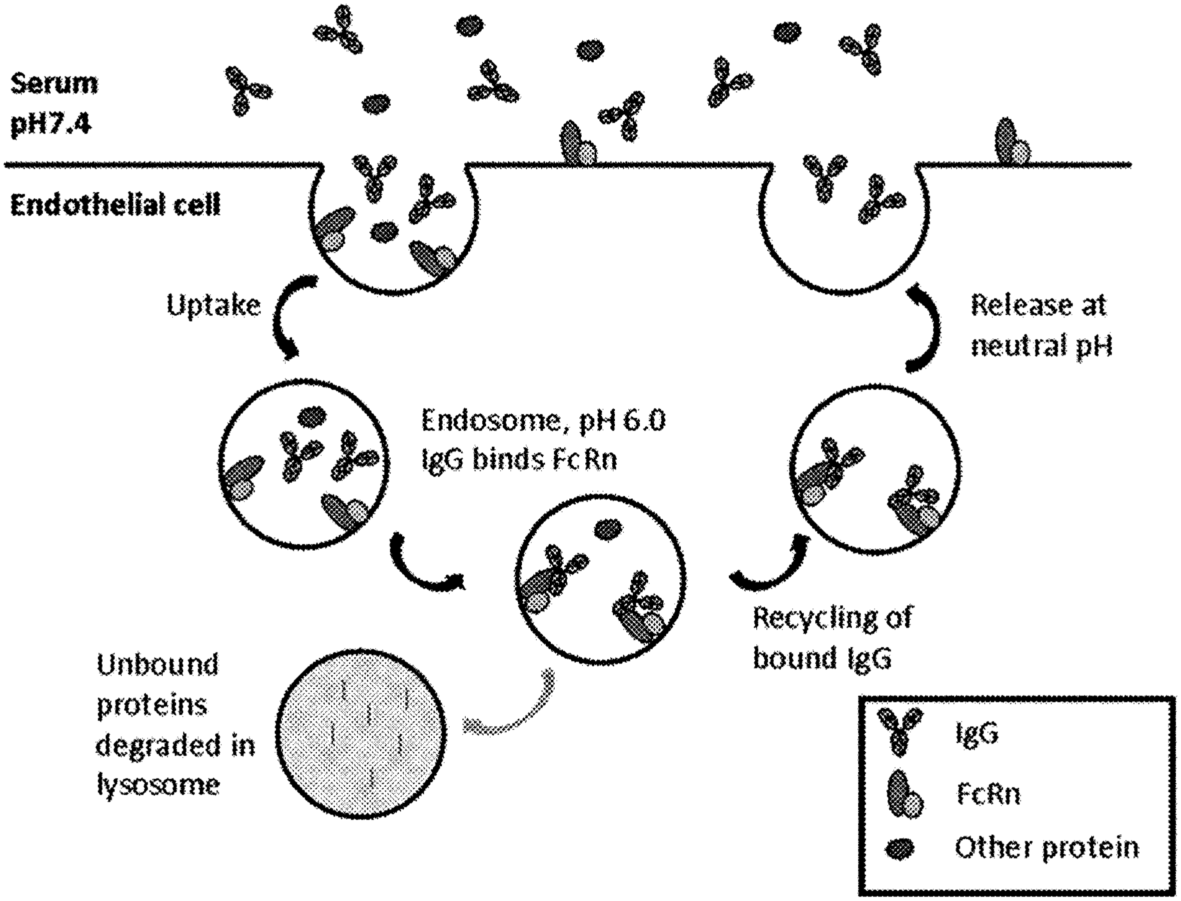
FIG. 13 is a schematic diagram schematically showing a process for recycling an antibody by FcRn.

A technique for linking an Fc domain of an antibody to a biologically active protein or an active pharmaceutical ingredient (API) to increase a half-life of API is a widely used technique. However, when in the Fc domain moiety of the antibody, an N-linked sugar chain is added to asparagine, which is the 297$^{th}$ amino acid, a sugar chain pattern is different from that of the human antibody or is not uniform and is produced in a heterogenous form depending on the characteristics of the host cell for antibody production. Therefore, the activity of a fusion protein to which API is linked may be not constant or an effect unnecessary in some cases, such as antibody-dependent cellular cytotoxicity (ADCC) and complement-dependent cytotoxicity (CDC), is exhibited to cause side effects. Moreover, it is known that the reason for the increase in half-life after administration of the antibody in vivo is that the antibody is absorbed due to endocytosis by vascular endothelial cells in vivo, then binds to a neonatal Fc receptor (hereinafter, referred to as "FcRn") due to a low pH in the endosomal state to avoid degradation by lysosomes, and is separated from FcRn under extracellular physiological pH conditions in a process in which an endosome is recycled to a cell membrane (FIG. 13). The reuse of the antibody by FcRn is known to exhibit an effect of prolonging the half-life of the antibody up to approximately 21 days (Raghavan, M. et al., *Biochem,* 34(45): 14649-14657, 1995).

However, since existing antibody Fc domains have different affinity with FcRn depending on the type of IgG, there is a limit to improving the half-life of API.

Accordingly, the present inventors designed an Fc domain protein variant which does not have activities of ADCC and CDC while increasing affinity of the existing Fc domain protein with FcRn.

Therefore, the present inventors designed a variant (SEQ ID NOs: 6 to 9) in which threonine (T), which is the 18$^{th}$ amino acid of the modified IgG4 Fc protein having the amino acid sequences set forth in SEQ ID NOs: 1 to 4, was substituted with glutamine (Q), and methionine (M), which is the 196$^{th}$ amino acid, was substituted with leucine (L), and the variant was named "NTIG (SEQ ID NO: 5)".

Example 2: Preparation of Monospecific Fusion Protein Construct

Subsequently, the present inventors prepared various fusion proteins in which various biologically active proteins were linked to the N-terminus and/or the C-terminus of the immunoglobulin Fc domain variant protein (NTIG) prepared in Example 1.

2-1: Design and Production of GLP-1E-NTIG

The present inventors designed a fusion protein (GLP-1E-NTIG, SEQ ID NO: 50) in which the NTIG protein (SEQ ID NO: 7) prepared in Example 1 was linked to the C-terminus of the GLP-1/Exendin-4 hybrid peptide (SEQ ID NO: 49), which is a hybrid peptide of GLP-1 and Exendin-4, through a linker peptide (($G_4S)_3$-IgD/IgG1 hybrid hinge, SEQ ID NO: 14) containing a hinge region in a hybrid form, and the fusion protein was named "PG-11". GLP-1E-NTIG was designed to add a tPA signal sequence (SEQ ID NO: 51) for secretion from a host cell. Meanwhile, a polynucleotide encoding PG-11 was synthesized using oligonucleotide synthesis, PCR amplification, and a site-directed mutagenesis technique, and then inserted into a pGP30 expression vector (Genexine, Inc., Korea). The prepared vector was transiently expressed using an ExpiCHO kit manufactured by Thermo Fisher Scientific Solutions LLC. Specifically, the vector prepared as above and an ExpiFectamine reagent contained in the kit were mixed in an ExpiCHO-S cell, the resultant was cultured for 1 day in an incubator with conditions of 8% $CO_2$ and 37° C., then the temperature was lowered to 32° C., and the culture was performed until the 7$^{th}$ day.

Figure 14A:
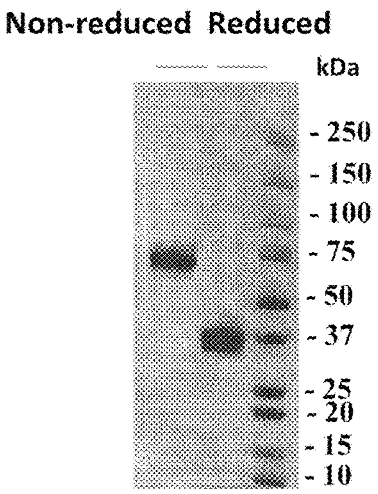
FIG. 14*a* is a photograph showing the results of SDS-PAGE analysis showing the sample production result of a fusion protein (PG-11) according to one exemplary embodiment of the present invention.
Figure 14B:
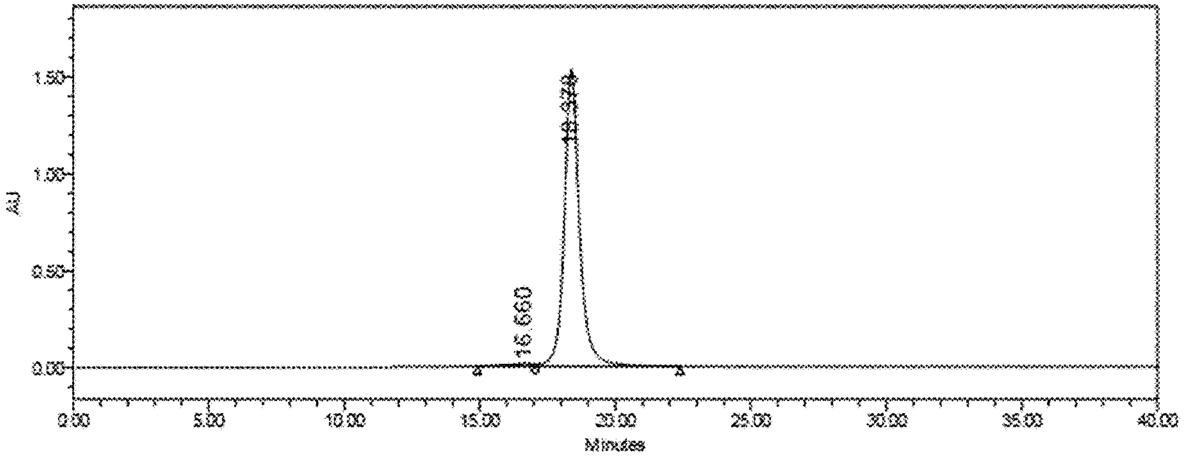
FIG. 14*b* is a chromatogram showing the results of analyzing the produced PG-11 by size-exclusion high-performance liquid chromatography (SEC-HPLC)

Thereafter, capturing and purification of protein A were performed, it was checked whether a candidate material was purified through SDS-PAGE analysis under non-reducing and reducing conditions, and formulation was performed with a formulation buffer solution according to the pI value of the candidate material. The formulated material was quantified using Nano drop, and the final purity was checked using SEC-HPLC (FIGS. 14*a* and 14*b*).

2-2: Design and Production of GLP-2-2G-NTIG

Figure 15A:
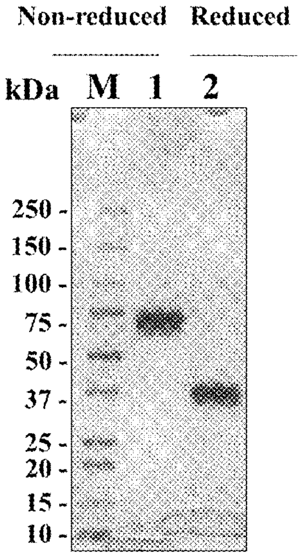
FIG. 15*a* is a photograph showing the results of SDS-PAGE analysis showing the sample production result of a fusion protein (PG-22) according to one exemplary embodiment of the present invention.
Figure 15B:
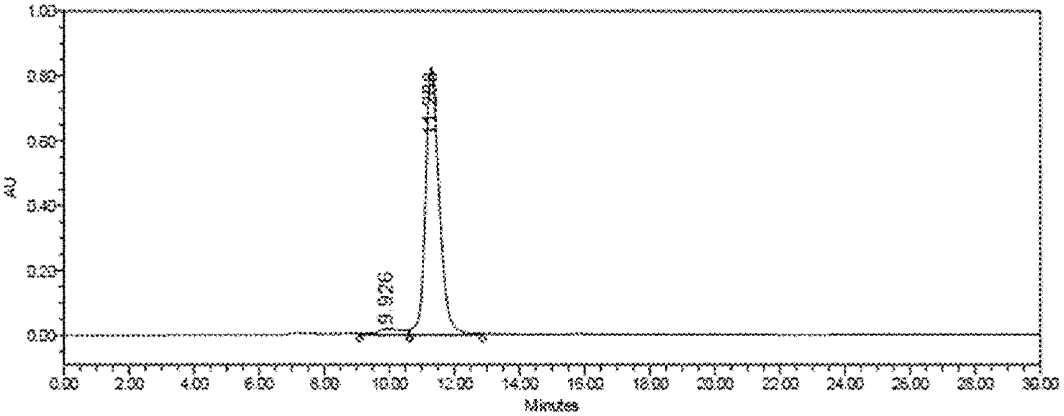
FIG. 15*b* is a chromatogram showing the results of analyzing the produced PG-22 by the size-exclusion high-performance liquid chromatography (SEC-HPLC)

The present inventors designed a fusion protein (GLP-2-2G-NTIG, SEQ ID NO: 53) in which NTIG (SEQ ID NO: 7) was linked, through the linker peptide (SEQ ID NO: 14), to the C-terminus of a GLP-2 analog (GLP-2-2G, SEQ ID NO: 52) that is a mutant in which alanine (A), which is the $2^{nd}$ amino acid of a human GLP-2 peptide, is substituted with glycine (G), and the fusion protein was named "PG-22". Similarly, the PG-22 was also designed to add the tPA signal sequence (SEQ ID NO: 51) for secretion. Similar to Example 2-1, a polynucleotide encoding PG-22 was prepared and inserted into the pGP30 expression vector (Genexine, Inc., Korea) to produce a protein using the ExpiCHO system, and then the final purity was checked (FIGS. 15*a* and 15*b*).

2-3: Design and Production of NTIG-IL-10V

Figure 16A:
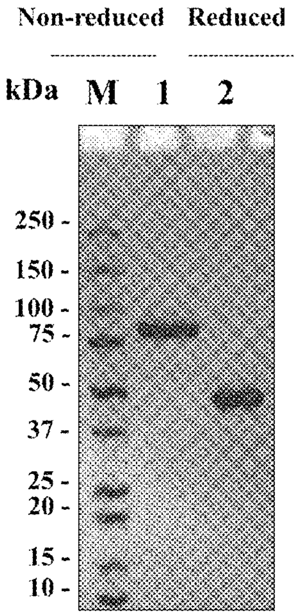
FIG. 16*a* is a photograph showing the results of SDS-PAGE analysis showing the sample production result of a fusion protein (PG-088) according to one exemplary embodiment of the present invention.
Figure 16B:
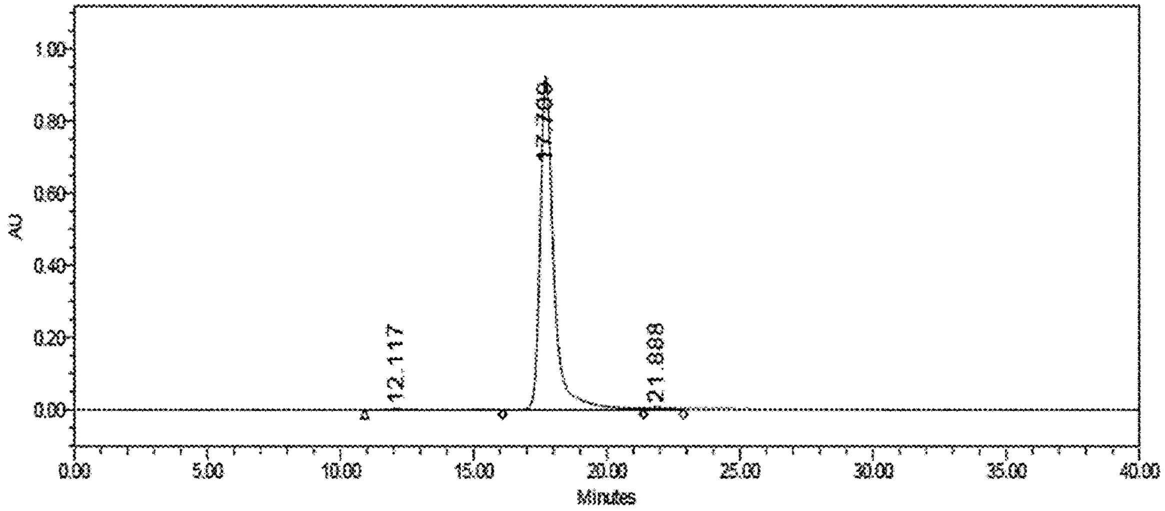
FIG. 16*b* is a chromatogram showing the results of analyzing the produced PG-088 by the size-exclusion high-performance liquid chromatography (SEC-HPLC)

The present inventors designed a fusion protein (NTIG-IL-10V, SEQ ID NO: 55) in which an IL-10 variant (SEQ ID NO: 54) was linked to the C-terminus of NTIG through a linker peptide (SEQ ID NO: 26), and the fusion protein was named "PG-088". Similar to Example 2-1, a polynucleotide encoding PG-088 was prepared and inserted into a pBispec expression vector (Genexine, Inc., Korea) to produce a protein using the ExpiCHO system, and then the final purity was checked (FIGS. 16*a* and 16*b*).

2-4: Design and Production of NTIG-IL-10V Monomer

Figure 17A:
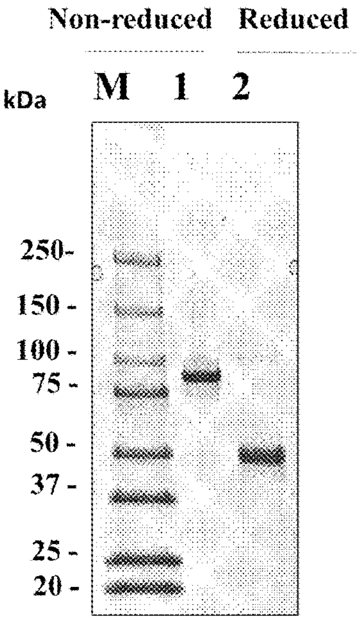
FIG. 17*a* is a photograph showing the results of SDS-PAGE analysis showing the sample production result of a fusion protein (PG-088m) according to one exemplary embodiment of the present invention.
Figure 17B:
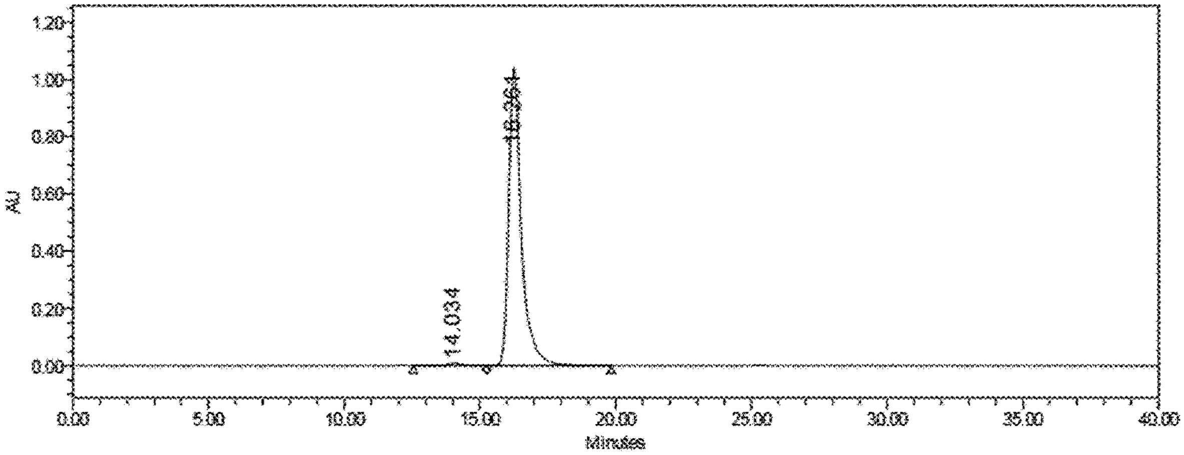
FIG. 17*b* is a chromatogram showing the results of analyzing the produced PG-088m by the size-exclusion high-performance liquid chromatography (SEC-HPLC)

The present inventors designed a fusion protein (NTIG-IL-10Vm, SEQ ID NO: 57) in which an IL-10 monomeric variant (SEQ ID NO: 56) was linked to the C-terminus of NTIG through the linker peptide (SEQ ID NO: 26), and the fusion protein was named "PG-088m". Similar to Example 2-1, a polynucleotide encoding PG-088m was prepared and inserted into the pBispec expression vector to produce a protein using the ExpiCHO system, and then the final purity was checked (FIGS. 17*a* and 17*b*). The IL-10 monomeric variant (IL-10Vm) is obtained by introducing a mutation for selectively inhibiting an immune-stimulating activity of the IL-10 protein, which has both different activities of an immune-stimulating activity and the immunosuppressive activity, and is a monomeric variant protein produced in a monomeric form by inserting a linker of GGSGGSGGS (SEQ ID NO: 46) in the middle of a process of protein production to solve the problem of aggregates generated due to the formation of self-dimerization in the process.

Example 3: Preparation of Bispecific Fusion Protein Gene Construct 3-1: Preparation of Anti-PD-L1-NTIG-IL-2

A polynucleotide encoding each of a fusion protein (anti-PD-L1-NTIG-IL-2) in which scFv targeting PD-L1 was linked to the N-terminus of NTIG (SEQ ID NO: 7) and IL-2 was linked to the C-terminus, and a fusion protein (anti-PD-L1-modified IgG4 Fc-IL-2) using a modified IgG4 Fc domain protein of SEQ ID NO: 2 instead of NTIG was inserted into the pBispec expression vector, and each protein was produced using the ExpiCHO system.

3-2: Design and Production of FcεRIα-NTIG-IL-10V

Figure 18A:
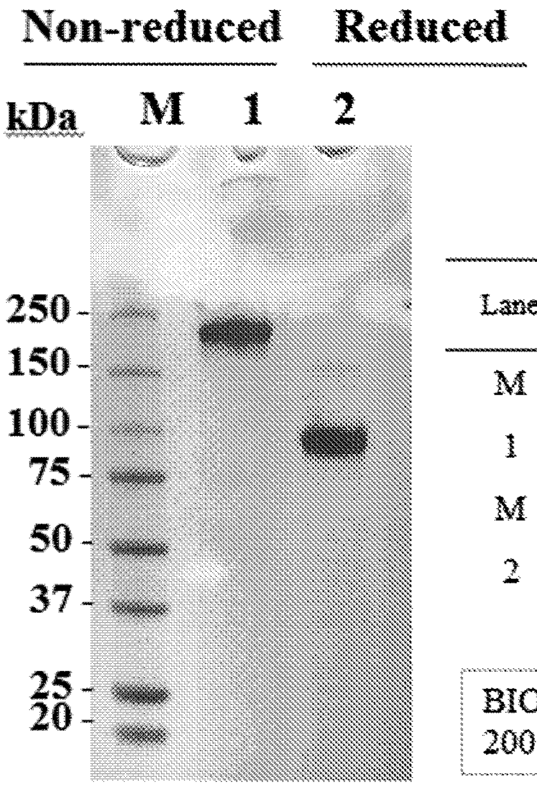
FIG. 18*a* is a photograph showing the results of SDS-PAGE analysis showing the sample production result of a fusion protein (PG-075) according to one exemplary embodiment of the present invention.
Figure 18B:
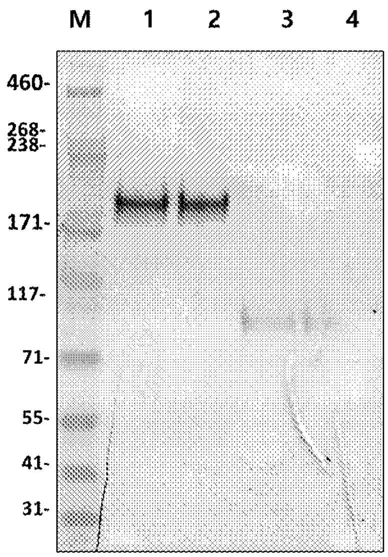
FIG. 18*b* is a photograph showing the results of western blot analysis of the produced PG-075 using an anti-IgG antibody.

The present inventors designed a bispecific fusion protein (FcεRIα-NTIG-IL-10V, SEQ ID NO: 59) in which an extracellular domain (SEQ ID NO: 58) of FcεRIα, which is a receptor specifically binding to IgE, was linked to the N-terminus of NTIG-IL-10V designed in Example 2-3 through a linker peptide (SEQ ID NO: 18), the bispecific fusion protein was named "PG-075", and a polynucleotide encoding the fusion protein was prepared and inserted into the pBispec expression vector. The PG-075 construct was also designed so that the tPA signal sequence (SEQ ID NO: 51) was positioned at the N-terminus for secretion, was produced using the ExpiCHO system, and subjected to SDS-PAGE and western blotting (FIGS. 18*a* and 18*b*).

3-3: Design and Production of FcεRIα-NTIG-IL-10Vm

Figure 19A:
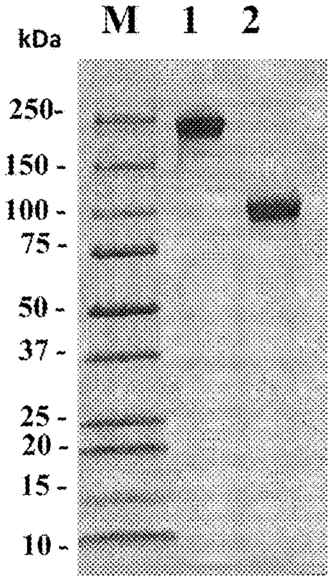
FIG. 19*a* is a photograph showing the results of SDS-PAGE analysis showing the sample production result of a fusion protein (PG-110) according to one exemplary embodiment of the present invention.
Figure 19B:
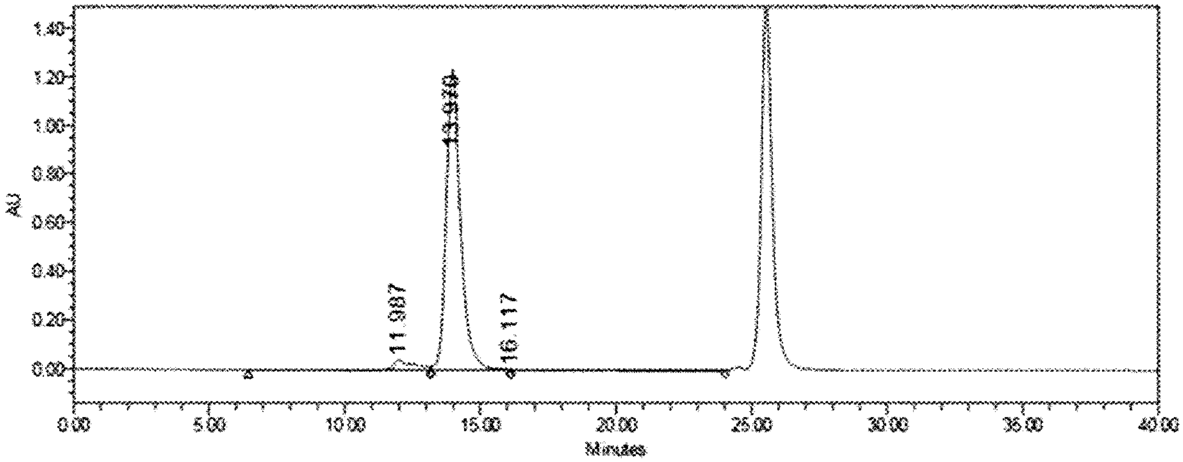
FIG. 19*b* is a chromatogram showing the results of analyzing the produced PG-110 by the size-exclusion high-performance liquid chromatography (SEC-HPLC)

The present inventors designed a bispecific fusion protein (FcεRIα-NTIG-IL-10Vm, SEQ ID NO: 60) in which the extracellular domain (SEQ ID NO: 58) of FcεRIα, which is a receptor specifically binding to IgE, was linked to the N-terminus of NTIG-IL-10Vm designed in Example 2-4 through the linker peptide (SEQ ID NO: 18), the bispecific fusion protein was named "PG-110", and a polynucleotide encoding the fusion protein was prepared and inserted into a pAD15 expression vector. The PG-110 construct was also designed so that the tPA signal sequence (SEQ ID NO: 51) was positioned at the N-terminus for secretion. A gene inserted into the pAD15 expression vector was transfected into a CHO DG44 cell, then subjected to methotrexate (MTX) amplification, and subjected to a single clone sorting operation to prepare a high-efficiency expressing cell line, and then a PG-110 protein was produced and purified from the high-efficiency expressing cell line (FIGS. 19*a* and 19*b*).

Example 4: Preparation of Anti-CD40L Hybrid Antibody 4-1: Preparation of Chimeric Anti-CD40L Antibody The present inventors prepared an anti-CD40L antibody obtained by introducing an FcγRIIα binding inhibitory variant into heavy-chain CH2 and CH3 domains of an antibody (C10) in which an Fc region of the mouse-derived anti-CD40L (anti-CD154) antibody described in WO2016/182335A1 was substituted with a human IgG1 Fc region, and the anti-CD40L antibody was named "C10M".

4-2: Preparation of Chimeric Anti-CD40L-NTIG Hybrid Antibody

The present inventors designed a hybrid heavy chain protein in which a heavy chain moiety in a Fab moiety of the C10M antibody is linked to the N-terminus, does not bind to FcγR, of the NTIG protein prepared in Example 1, and the hybrid heavy chain protein was named "PG-129".

A polynucleotide encoding a hybrid heavy chain of the hybrid heavy chain protein in which the heavy chain moiety ($V_H$-CH1, SEQ ID NO: 61) in Fab of the C10M antibody is linked to NTIG (SEQ ID NO: 7) was prepared and inserted into a pAD15 expression vector (WO2015/009052A). Moreover, a polynucleotide encoding a light heavy moiety ($V_L$—$C_L$, SEQ ID NO: 62) in Fab of the C10M antibody was inserted into the pAD15 expression vector so that the polynucleotide can be regulated under a dual promoter. Thereafter, the vector was co-transfected into a CHO DG44 (from Dr. Chasin, Columbia University, USA) cell using a Neon-transfection system.

The expression vector completed as above was also transiently expressed using the ExpiCHO kit manufactured by Thermo Fisher Scientific Solutions LLC. Specifically, the vector construct prepared as above and the ExpiFectamine reagent contained in the kit were mixed in the ExpiCHO-S cell, the resultant was cultured for 1 day in an incubator with conditions of 8% $CO_2$ and 37° C., then the temperature was lowered to 32° C., and the culture was performed until the $7^{th}$ day.

Thereafter, capturing and purification of protein A were performed, it was checked whether a candidate material was purified through PAGE analysis and western blot analysis under non-reducing and reducing conditions, and formulation was performed with a formulation buffer solution according to the pI value of the candidate material. The formulated material was quantified using Nano drop, and the final purity was checked using SEC-HPLC.

Figure 20A:
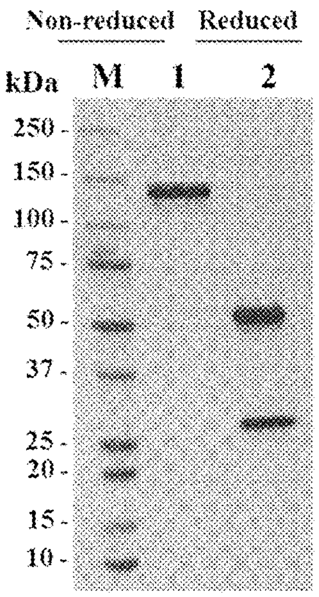
FIG. 20*a* is a photograph showing the results of SDS-PAGE analysis showing the sample production result of a fusion protein (PG-129) according to one exemplary embodiment of the present invention.
Figure 20B:
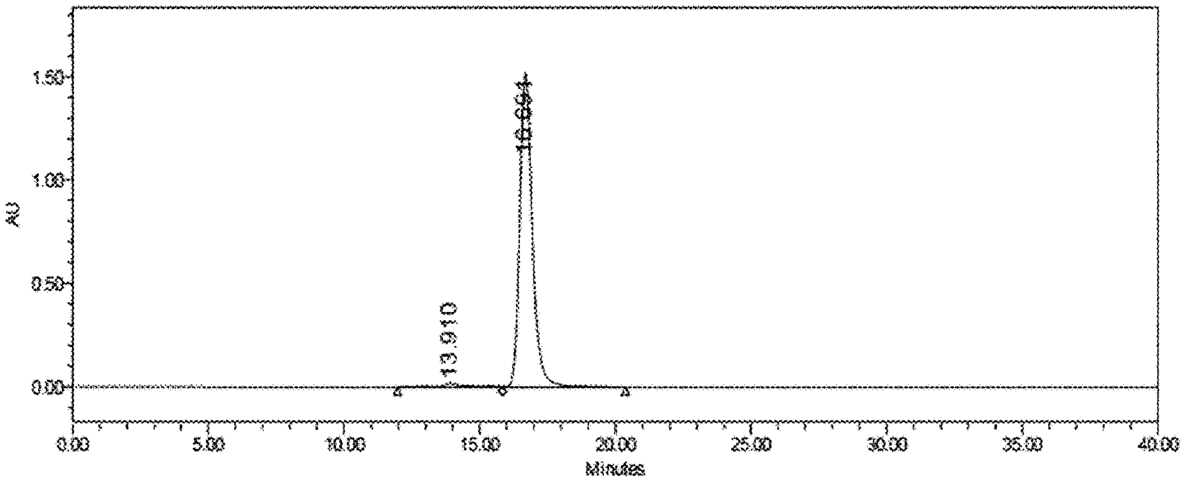
FIG. 20*b* is a chromatogram showing the results of analyzing the produced PG-129 by the size-exclusion high-performance liquid chromatography (SEC-HPLC)
Figure 21A:
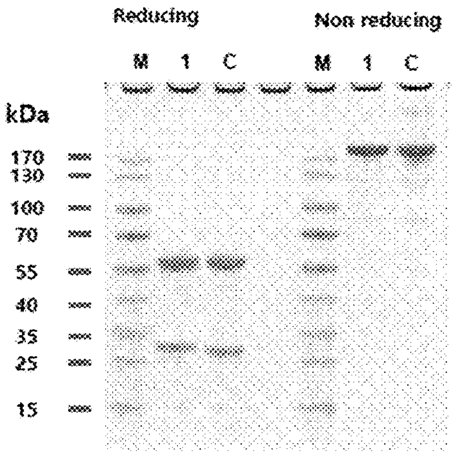
FIG. 21*a* is a photograph showing the results of SDS-PAGE analysis showing the sample production result of a fusion protein (PG-400) according to one exemplary embodiment of the present invention.
Figure 21B:
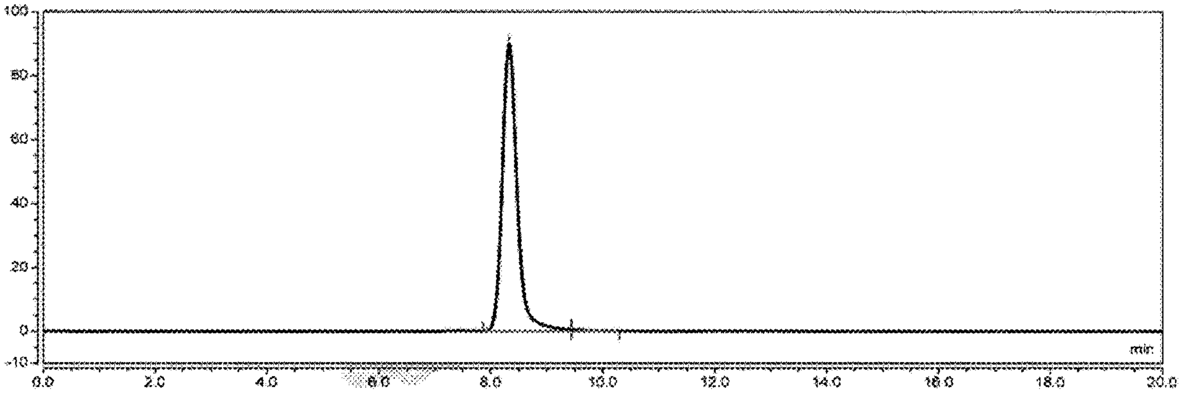
FIG. 21*b* is a chromatogram showing the results of analyzing the produced PG-400 by the size-exclusion high-performance liquid chromatography (SEC-HPLC)
Figure 22A:
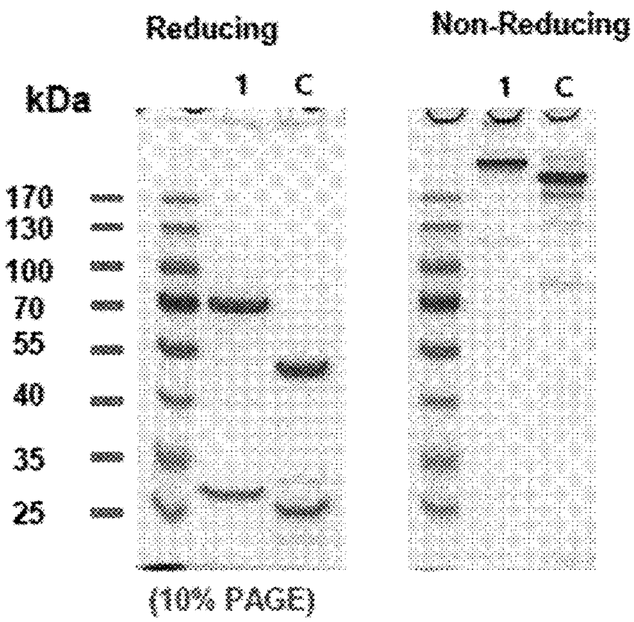
FIG. 22*a* is a photograph showing the results of SDS-PAGE analysis showing the sample production result of a fusion protein (PG-410) according to one exemplary embodiment of the present invention.
Figure 22B:
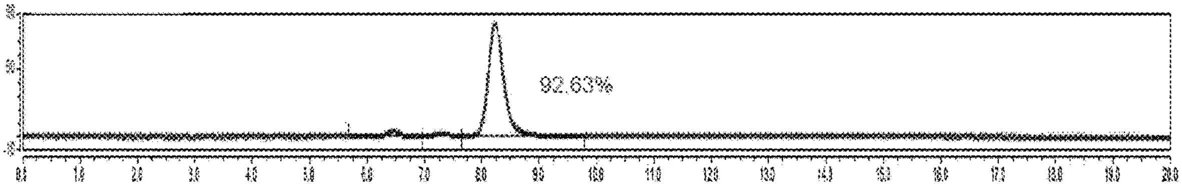
FIG. 22*b* is a chromatogram showing the results of analyzing the produced PG-410 by the size-exclusion high-performance liquid chromatography (SEC-HPLC)

As a result, as shown in FIGS. 20*a* and 20*b*, the light chain and the heavy chain were normally expressed, a single band appeared under the non-reducing conditions, and thus it could be found that a normal heterotetramer was formed. Moreover, as a result of SEC-HPLC analysis, the purity was 97.9%, which is very high.

4-3: Preparation of Humanized Anti-CD40L-NTIG Hybrid Antibody

The chimeric antibodies have sufficiently improved disadvantages of the conventional human antibodies by introducing the NTIG technique (immunoglobulin Fc domain variant protein) of the present invention, but the present inventors have determined that the antigen-binding site was still a mouse-derived antibody and thus unnecessary immune responses in the human body may occur, and, in order to prepare a safer hybrid antibody, designed a humanized antibody (anti-CD40L Fab-NTIG) in which the framework part except for an antigenic determinant of Fab, which is the antigen-binding fragment of the antibody that is the base of the present invention, was substituted with the sequence of the human antibody (Tables 1 and 2), and the humanized antibody was named "PG-400".

Furthermore, the present inventors designed to prepare a bispecific hybrid antibody (anti-CD40L Fab-NTIG-IL-10Vm) in which the IL-10 monomeric variant protein (SEQ ID NO: 56), which is a cytokine having an immunosuppressive activity, was linked to the heavy chain C-terminus of the hybrid antibody (Table 3), and the bispecific hybrid antibody was named "PG-410". The structure of the light chain of the bispecific hybrid antibody is the same as shown in Table 2.

TABLE 1

Configuration of heavy chain of humanized anti-CD40L-NTIG hybrid antibody

| Constituent element | Amino acid sequence | SEQ ID NO: |
|---|---|---|
| Anti-CD40L heavy chain Vh-CH1 | QVQLVQSGAEVVKPGASVKLSCKASGYIFTSYYMY WVKQAPGQGLEWIGEINPSNGDTNFNEKFKSKATL TVDKSASTAYMELSSLRSEDTAVYYCTRSDGRNDM DSWGQGTLVTVSSASTKGPSVFPLAPSSKSTSGGT AALGCLVKDYFPEPVTVSWNSGALTSGVHTFPAVL QSSGLYSLSSVVTVPSSSLGTQTYICNVNHKPSNT KVDKKV | 64 |
| hinge + NTIG | EPKSCDKTHT CPPCPSHTQP LGVFLFPPKP KDQLMISRTP EVTCVVVDVS QEDPEVQFNW YVDGVEVHNA KTKPREEQFN STYRVVSVLT VLHQDWLNGK EYKCKVSNKG LPSSIEKTIS KAKGQPREPQ VYTLPPSQEE MTKNQVSLTC LVKGFYPSDI AVEWESNGQP ENNYKTTPPV LDSDGSFFLY SRLTVDKSRW QEGNVFSCSV LHEALHNHYT QKSLSLSLG | 68 |

TABLE 2

Configuration of light chain of humanized anti-CD40L-NTIG hybrid antibody

| Constituent element | Amino acid sequence | SEQ ID NO: |
|---|---|---|
| Light chain of anti-CD40L antibody | DIVLTQSPATLSVSPGERATISCRASQRVSSSTY SYMHWYQQKPGQPPKLLIKYASNLESGVPARFSG SGSGTDFTLTISSVEPEDFATYYCQHSWEIPPTF GGGTKLEIKRTVAAPSVFIFPPSDEQLKSGTASV VCLLNNFYPREAKVQWKVDNALQSGNSQESVTEQ DSKDSTYSLSSTLTLSKADYEKHKVYACEVTHQG LSSPVTKSFNRGEC | 67 |

TABLE 3

Configuration of heavy chain of bispecific anti-CD40L-NTIG hybrid antibody

| Constituent element | Amino acid sequence | SEQ ID NO: |
|---|---|---|
| Anti-CD40L heavy chain $V_H$-CH1 | QVQLVQSGAEVVKPGASVKLSCKASGYIFTSYYMYW VKQAPGQGLEWIGEINPSNGDTNFNEKFKSKATLTV DKSASTAYMELSSLRSEDTAVYYCTRSDGRNDMDSW GQGTLVTVSSASTKGPSVFPLAPSSKSTSGGTAALG | 64 |

TABLE 3-continued

Configuration of heavy chain of bispecific anti-CD40L-NTIG hybrid antibody

| Constituent element | Amino acid sequence | SEQ ID NO: |
|---|---|---|
| | CLVKDYFPEPVTVSWNSGALTSGVHTFPAVLQSSGL YSLSSVVTVPSSSLGTQTYICNVNHKPSNTKVDKKV | |
| hinge + NTIG | EPKSCDKTHT CPPCPSHTQP LGVFLFPPKP KDQLMISRTP EVTCVVVDVS QEDPEVQFNW YVDGVEVHNA KTKPREEQFN STYRVVSVLT VLHQDWLNGK EYKCKVSNKG LPSSIEKTIS KAKGQPREPQ VYTLPPSQEE MTKNQVSLTC LVKGFYPSDI AVEWESNGQP ENNYKTTPPV LDSDGSFFLY SRLTVDKSRW QEGNVFSCSV LHEALHNHYT QKSLSLSLG | 68 |
| Linker peptide | AAGSGGGGGS GGGGSGGGGS | 26 |
| IL-10Vm | SPGQGTQSENSCTHFPGNLPNMLRDLRDAFSRVKTF FQMKDQLDNLLLKESLLEDFKGYLGCQALSEMIQFY LEEVMPQAENQDPDAKAHVNSLGENLKTLRLRLRRC HRFLPCENGGSGGSGGSKSKAVEQVKNAFNKLQEKG IYKAMSEFDIFINYIEAYMTMKIRN | 56 |

In order to produce humanized anti-CD40L hybrid antibodies (PG-400 and PG-410), a polynucleotide encoding each of the heavy chain and the light chain of the antibody was prepared, and then for temporary expression in an animal cell, plasmid DNA was transfected into a HEK293F cell using the N293F vector system (Y-BIOLOGICS). In order to prepare a nucleic acid, 25 μg of plasmid DNA was added to and mixed with 3 ml of the medium, and then 25 μl of 2 mg/ml Polyethylenimine (PEI, PolyPlus, USA) was added thereto, followed by mixing. The reaction solution was allowed to stand at room temperature for 15 minutes, and then put into 40 ml of a culture solution cultured at $1\times10^6$ cells/ml, and the resultant was cultured for 24 hours under conditions of 120 rpm, 37° C., and 8% $CO_2$. 24 hours after DNA transfection, a nutritional supplement medium component (Soytone, BD, USA) was added so that the final concentration was 10 g/L. After culturing for 7 days, the cell culture solution was centrifuged at 5000 rpm for 10 minutes to collect a supernatant.

Subsequently, a protein A resin filled a column and was washed with 1×DPBS, the collected supernatant was combined with the resin at 4° C. at a rate of 0.5 ml/min, and a protein was eluted with 0.1 M glycine. In order to replace a buffer solution, the eluted solution was put into a dialysis tube (GeBAflex tube, Geba, Israel) and dialyzed at 4° C. with 1×DPBS. The obtained substance was subjected to gel filtration using a Superdex 200 resin, and then formulated with a PBS (pH of 7.4) buffer solution.

For the purified hybrid antibody, the yield and the purity of the hybrid antibody were assayed through SDS-PAGE analysis, size-exclusion FPLC, and size-exclusion HPLC analysis.

As a result, as shown in FIGS. 21*a*, 21*b*, 22*a*, and 22*b*, it could be found that PG-400 and PG-410 to which the humanized anti-CD40L hybrid antibodies of the present invention were applied were produced with high purity.

4-4: Design of Anti-CD40L scFv-NTIG-IL-10 Fusion Protein

The present inventors sorted out a variable region moiety in the Fab of the humanized anti-CD40L antibody, designed scFv using the sorted-out variable region moiety, designed a single chain-based antibody binding-fragment fusion protein by inserting scFv instead of the $V_H$-CH1 moiety of the heavy chain construct of the anti-CD40L antibody used in Example 4-3, and designed a bispecific fusion protein in which the IL-10 monomeric variant (SEQ ID NO: 56) used in Example 4-3 was linked to the C-terminus of the anti-CD40L scFv-NTIG through the linker peptide (SEQ ID NO: 26) (Table 4). In the present Example, the anti-CD40L scFv is composed of the light-chain variable region ($V_L$), the linker, the heavy-chain variable region ($V_H$) in this order, but conversely, an anti-CD40L scFv, which is composed of $V_H$, the linker, and $V_L$ in this order, may be used because the CD40L-binding ability is maintained even in a case of using the latter anti-CD40L scFv, and also regarding the type of linker, various types can be used.

TABLE 4

Configuration of anti-CD40L scFv-NTIG-IL-10 fusion protein

| Constituent element | | Amino acid sequence | SEQ ID NO: |
|---|---|---|---|
| Signal sequence | | MGWSCIILFLVATATGVHS | 62 |
| Anti-CD40L scFv | $V_L$ | DIVLTQSPATLSVSPGERATISCRASQRVSSSTYSYMH WYQQKPGQPPKLLIKYASNLESGVPARFSGSGSGTDFT LTISSVEPEDFATYYCQHSWEIPPTFGGGTKLEIKRTV AAPSV | 69 |

TABLE 4-continued

Configuration of anti-CD40L scFv-NTIG-IL-10 fusion protein

| Constituent element | Amino acid sequence | SEQ ID NO: |
|---|---|---|
| Linker 1 | GSTSGSGKPGSGEGS | 48 |
| $V_H$ | QVQLVQSGAEVVKPGASVKLSCKASGYIFTSYYMYWVK<br>QAPGQGLEWIGEINPSNGDTNFNEKFKSKATLTVDKSA<br>STAYMELSSLRSEDTAVYYCTRSDGRNDMDSWGQGTLV<br>TVSS | 70 |
| hinge + NTIG | EPKSCDKTHT CPPCPSHTQP LGVFLFPPKP<br>KDQLMISRTP EVTCVVVDVS QEDPEVQFNW<br>YVDGVEVHNA KTKPREEQFN STYRVVSVLT<br>VLHQDWLNGK EYKCKVSNKG LPSSIEKTIS<br>KAKGQPREPQ VYTLPPSQEE MTKNQVSLTC<br>LVKGFYPSDI AVEWESNGQP ENNYKTTPPV<br>LDSDGSFFLY SRLTVDKSRW QEGNVFSCSV<br>LHEALHNHYT QKSLSLSLG | 68 |
| Linker 2 | AAGSGGGGGS GGGGSGGGGS | 26 |
| IL-10Vm | SPGQGTQSENSCTHFPGNLPNMLRDLRDAFSRVKTFFQ<br>MKDQLDNLLLKESLLEDFKGYLGCQALSEMIQFYLEEV<br>MPQAENQDPDAKAHVNSLGENLKTLRLRLRRCHRFLPC<br>ENGGSGGSGGSKSKAVEQVKNAFNKLQEKGIYKAMSEF<br>DIFINYIEAYMTMKIRN | 56 |

Example 5: Preparation of Heterodimer

The present inventors designed bispecific fusion proteins containing both the GLP-1 analog and the GLP-2 analog as shown in Table 5. In these bispecific fusion proteins, the knobs-into-holes (KIH) structure is introduced so as to form a heterodimer by an intermolecular disulfide bond and a hydrophobic interaction between the first fusion protein and the second fusion protein.

A difference between Examples 5-1 and 5-2 is whether an N-linked sugar chain attachment site is included so that an N-glycan sugar chain can be linked to the linker linking the GLP-1 analog of the first fusion protein to NTIG. This is because GLP-1 as well as Exendin 4 (Ex4), oxyntomodulin (OXM), GLP-2 all bind to GLP-1R which is a GLP-1 receptor, whereas only GLP-2 binds to GLP-2R, and GLP-1R is expressed in various organs such as a brain, a heart, a liver, muscle, and pancreas in addition to gastrointestinal tract (GI tract), and thus it is necessary to lower the affinity with GLP-1R somewhat in order to allow GLP-1 to function specifically in the gastrointestinal tract. For the reason, in order to lower the binding force of the GLP-1 analog to GLP-1R somewhat, the present inventors used a protein to which a glycan attachment domain was added so that glycan can be attached to the linker moiety (including the IgD/IgG1 hybrid hinge) of the GLP-1 analog (Example 5-1).

TABLE 5

Design of fusion protein for formation of GLP-1/GLP-2 heterodimer according to one exemplary embodiment of present invention

| Example | Name | GLP-1/2 analog (SEQ ID NO:) | Linker (SEQ ID NO:) | Fc region | Overall configuration (SEQ ID NO:) |
|---|---|---|---|---|---|
| 5-1 | MG12-4 | 1. GLP-1/ Exendin 4 hybrid (49) | Glycan linker (21) | knob | First fusion protein (71) |
| | | 2. GLP-2-2G (52) | Non-glycan linker (14) | hole | Second fusion protein (72) |
| 5-2 | MG12-5 | 1. GLP-1/ Exendin 4 hybrid (49) | Non-glycan linker (14) | knob | First fusion protein (73) |
| | | 2. GLP-2-2G (52) | Non-glycan linker (14) | hole | Second fusion protein (72) |

The vector constructs prepared as above were transiently expressed using the ExpiCHO kit manufactured by Thermo Fisher Scientific Solutions LLC. Specifically, the vector constructs prepared as above and the ExpiFectamine reagent contained in the kit were mixed in the ExpiCHO-S cell, the resultant was cultured for 1 day in an incubator with conditions of 8% $CO_2$ and 37° C., then the temperature was lowered to 32° C., and the culture was performed until the 7th day.

Figure 23:
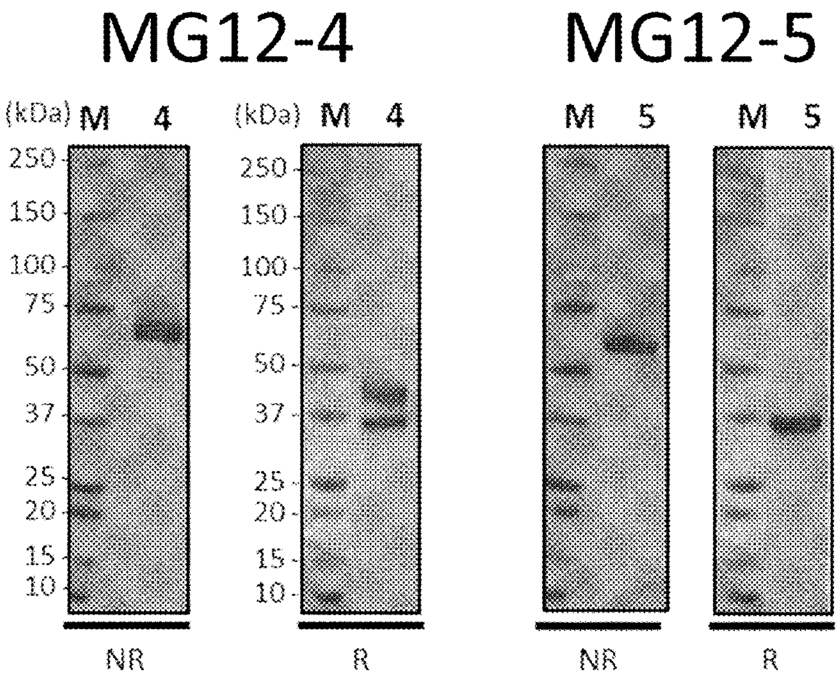
FIG. 23 is a photograph showing the results of SDS-PAGE analysis showing the sample production results of heterodimer proteins MG12-4 (left side) and MG12-5 (right side) according to one exemplary embodiment of the present invention.

The supernatant obtained through the culturing and the heterodimer proteins (were named 'MG12-4' and 'MG12-5', respectively) of Examples 5-1 and 5-2 purified through a protein A column and a secondary column were appropriately diluted with a 4×LDS sample buffer solution and water for injection to prepare a sample so that the final concentration was 3 to 10 μg/20 μL. In a case of a sample under the reducing conditions, each substance to be analyzed, the 4×LDS sample buffer solution, a 10× reducing agent, and the water for injection were appropriately diluted to prepare a sample so that the final concentration was 3 to 10 μg/20 μL, and the sample was heated in a 70° C. heating block for 10 minutes. The prepared sample was loaded in an amount of 20 μL in each well of a gel fixed in an electrophoresis apparatus which was installed in advance. For a size marker, the sample was loaded at 3 to 5 μL/well. After a power supply device was set to 120 V and 90 minutes, electrophoresis was performed. The gel subjected to the electrophoresis was separated, and then stained using a staining solution and a destaining solution, and the results were analyzed. As a result, as shown in FIG. 23, it could be confirmed that the heterodimer according to one exemplary embodiment of the present invention was normally produced.

Example 6: Analysis of Effect of Hinge in Fusion Protein Production

The present inventors investigated how the production efficiency of the protein varies depending on the type of hinge when API is linked to the N-terminus of the NTIG protein, while linking various types of API to the N-terminus and/or the C-terminus of the NTIG protein of the present invention.

6-1: Preparation of FcεRIα-NTIG-IL-13a2

The present inventors designed a bispecific fusion protein (FcεRIα-NTIG-IL-13Rα2) in which FcεRIα (SEQ ID NO: 58) was linked to the N-terminus of NTIG (SEQ ID NO: 7) and IL-13Rα2 (SEQ ID NO: 74) was linked to the C-terminus, and the bispecific fusion protein was named "PG-50". While producing PG-50, a hinge region linking FcεRIα to NTIG was investigated for protein productivity when using an IgD hinge (SEQ ID NO: 15) or a combination of a $(G_4S)_3$ linker and an IgG1 hinge (SEQ ID NO: 16). In this way, a fusion protein using the IgD hinge was named "PG-50-1", and a fusion protein using the $(G_4S)_3$ linker/IgG1 hinge was named "PG-50-2". In a case of the IgD hinge, one intermolecular disulfide bond was formed, and in a case of the $(G_4S)_3$ linker/IgG1 hinge, two intermolecular disulfide bonds were formed.

Figure 24A:
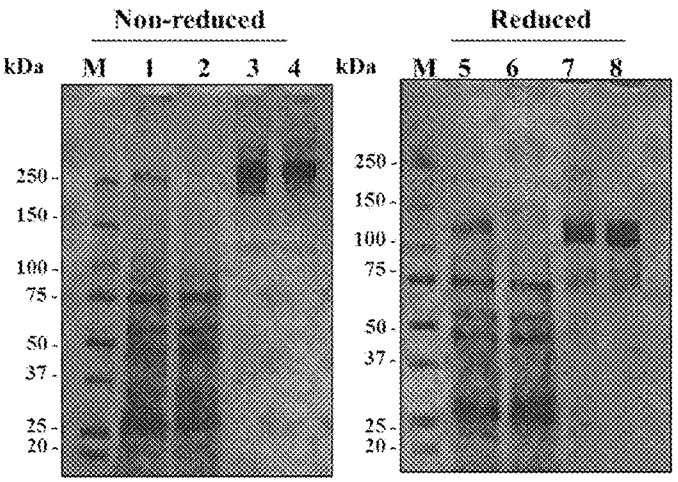
FIG. 24*a* is a photograph showing the results of SDS-PAGE analysis showing the sample production result of a fusion protein (PG-50-1) according to one exemplary embodiment of the present invention.
Figure 24A:
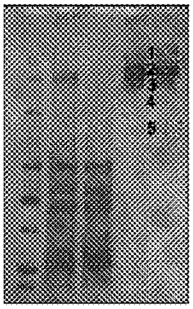
Figure 24B:
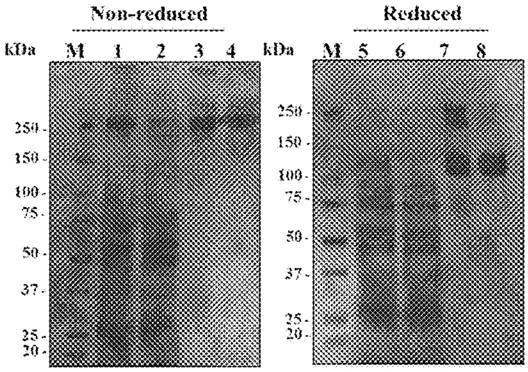
FIG. 24*b* is a photograph showing the results of SDS-PAGE analysis showing the sample production result of a fusion protein (PG-50-2) according to one exemplary embodiment of the present invention.
Figure 24B:
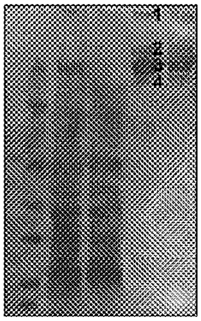

As a result, as shown in FIGS. 24*a* and 24*b*, it was found that the production yield for the target material of the fusion protein (PG-50-2) containing the IgG1 hinge was increased by about 15% compared to the PG-50-1 containing the IgD hinge.

6-2: Preparation of GLP-2-2G-NTIG-IL-10 wt

The present inventors analyzed the effects of various types of hinges on a protein production yield using different types of API. For the analysis, specifically, a construct was prepared in which GLP-2-2G (SEQ ID NO: 52) was linked to the N-terminus of NTIG (SEQ ID NO: 7) and IL-10 wt (SEQ ID NO: 75) was linked to the C-terminus of NTIG. Here, a bispecific fusion protein (GLP-2-2G-NTIG-IL-10 wt) was designed by linking GLP-2-2G to NTIG using a $(G_4S)_3$ linker+IgD/IgG1 hybrid hinge (SEQ ID NO: 14), and linking IL-10 wt to the C-terminus of NTIG using a linker peptide consists of the amino acid sequence set forth in SEQ ID NO: 26, and was named "PG-073". A polynucleotide encoding the fusion protein designed as above was prepared and then inserted into the pBispec expression vector, a fusion protein was expressed using the ExpiCHO system according to the method used in Example 2-1, and then the protein expression level in the culture supernatant was checked by SDS-PAGE. The IgD/IgG1 hybrid hinge forms two intermolecular disulfide bonds.

Figure 24C:
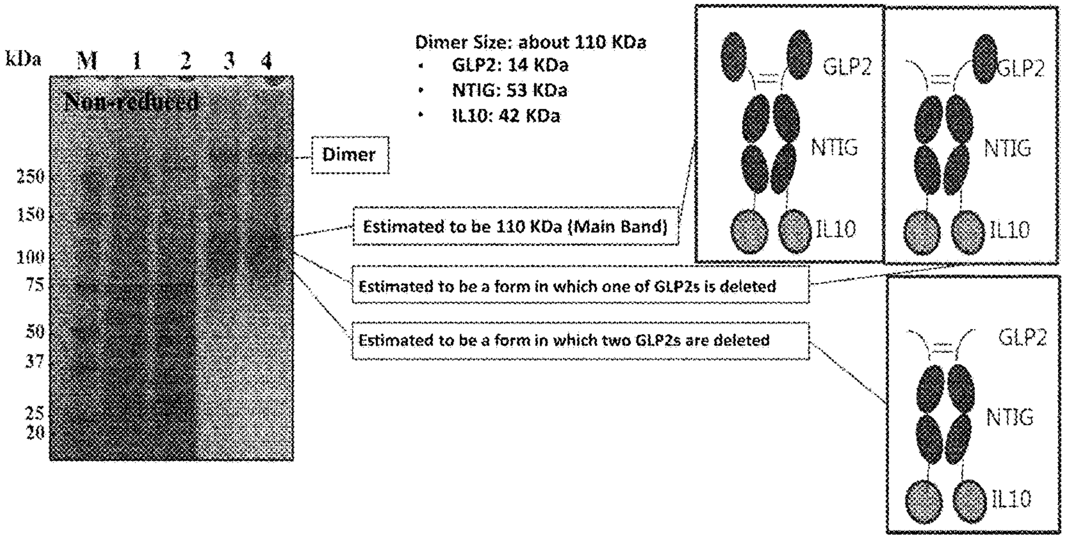
FIG. 24*c* is a photograph (left side) showing the results of SDS-PAGE analysis showing the sample production result of a fusion protein (PG-073) according to one exemplary embodiment of the present invention and a schematic diagram (right side) showing structures of various cleavage forms of the fusion protein estimated based on the SDS-PAGE analysis results.

As a result, as shown in FIG. 24*c*, in a case of PG-073, the size of a main band was 110 kDa under the non-reducing conditions, and it was confirmed that a bispecific fusion protein to which both GLP-2-2G and IL-10 were linked was formed. However, a band in which one or both of the GLP-2 were cleaved was found below the main band. Therefore, the $(G_4S)_3$ linker+IgD/IgG1 hybrid hinge linker used between GLP-2 and NTIG was found to be somewhat unstable. Moreover, the amount of the fusion protein produced based on 100 ml of the culture solution was only 0.5 mg (PG-073) and thus protein productivity was decreased, and the purity was also about 66%, which is low.

6-3 and 6-4: Preparation of GLP-2-2G (3 Point)-NTIG-IL-10Vm

Accordingly, the present inventors designed fusion proteins (GLP-2V (3 point)-NTIG-IL-10Vm) in which in the GLP-2-2G-NTIG-IL-10wt fusion protein, GLP-2-2G was changed to a mutant (SEQ ID NO: 76) containing a 3 point mutation, the hinge portion was replaced with a different type of linker or hinge (each SEQ ID NO: 17 or 18), and IL-10 wt was replaced with IL-10Vm prepared in Example 2-4, and the fusion proteins were named "PG210-5 (Example 6-3)" and "PG210-6 (Example 6-4), respectively.

After a polynucleotide encoding each of the fusion proteins was inserted into the pBispec expression vector, a fusion protein was expressed using the ExpiCHO system according to the method used in Example 2-1, and then the protein expression level in the culture supernatant was checked by SDS-PAGE.

Figure 24D:
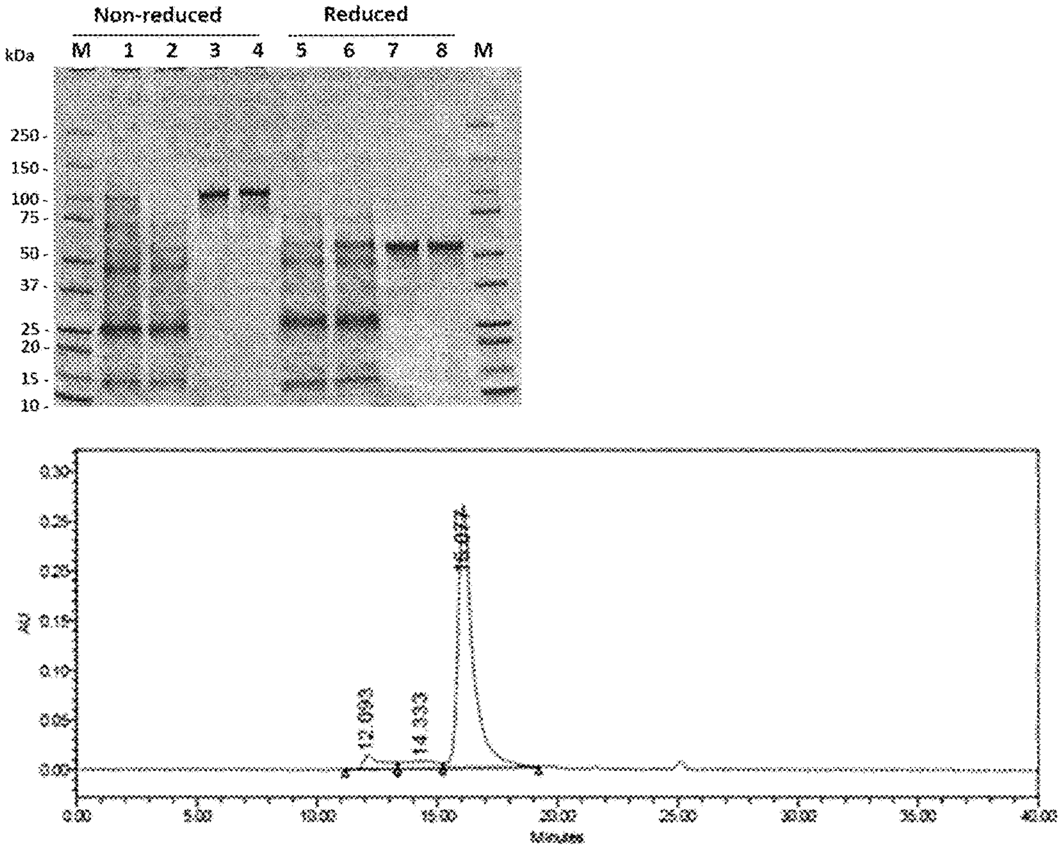
FIG. 24*d* is a photograph (upper part) showing the results of SDS-PAGE analysis showing the sample production result of a fusion protein (PG-210-5) according to one exemplary embodiment of the present invention and a chromatogram (lower part) showing the results of analyzing the produced PG-210-5 by the size-exclusion high-performance liquid chromatography (SEC-HPLC)
Figure 24E:
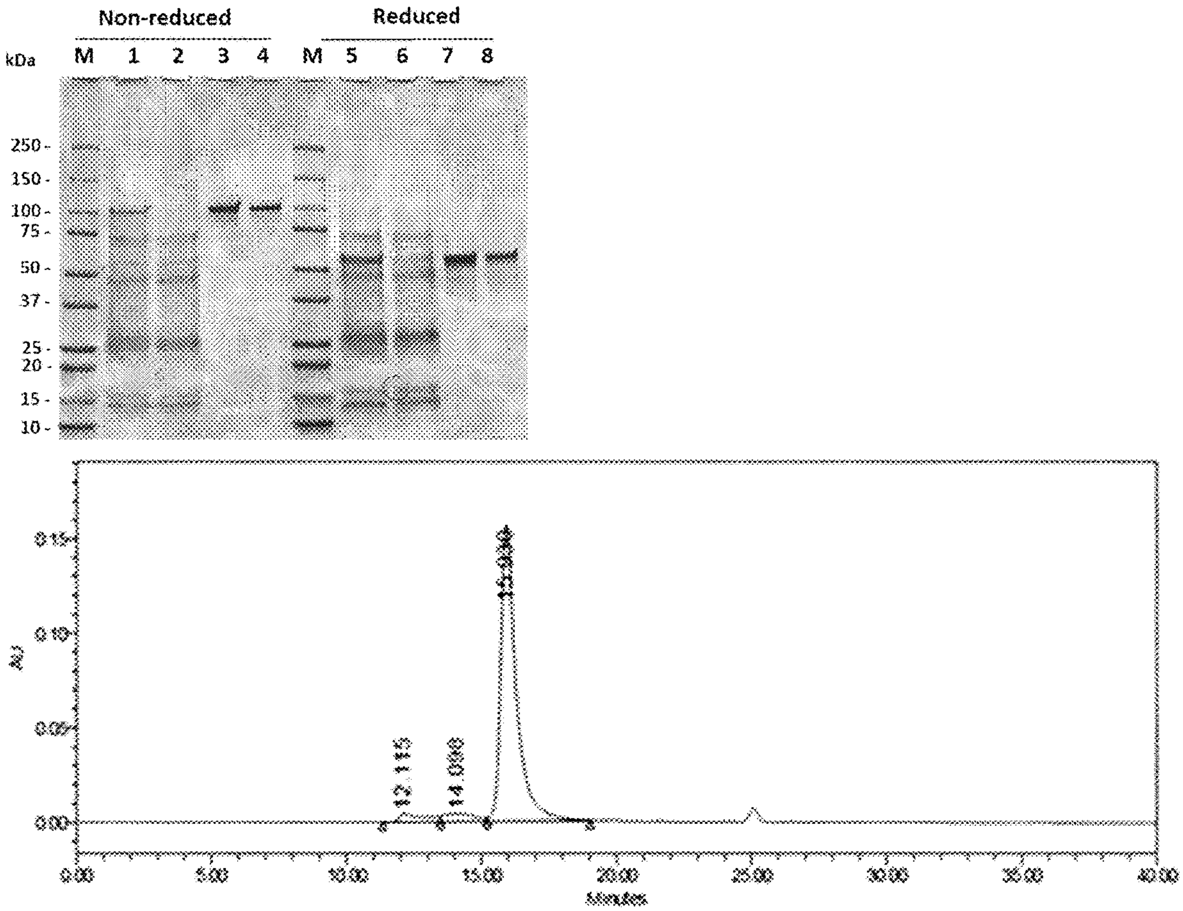
FIG. 24*e* is a photograph (upper part) showing the results of SDS-PAGE analysis showing the sample production result of a fusion protein (PG-210-6) according to one exemplary embodiment of the present invention and a chromatogram (lower part) showing the results of analyzing the produced PG-210-6 by the size-exclusion high-performance liquid chromatography (SEC-HPLC)

As a result, as shown in FIGS. 24*d* and 24*e*, in a case of PG-210-5, 3.48 mg of protein was found based on 200 ml of the culture solution and the purity was found to be about 88.3%, and in a case of PG-210-6, 5 mg of protein was found and the purity was found to be 90.7%.

Experimental Example 1: Analysis of FcRn-Binding Affinity

The present inventors compared the binding affinity of the NTIG protein of the present invention with FcRn to IgG4 Fc and IgG1 antibodies.

For the comparison, specifically, the recombinant FcRn (rhFcRn, R&D systems, USA), which is a ligand, was dissolved in an acetate buffer at a concentration of 5 μg/ml, and then fixed to a biosensor chip (Series S CM5 sensor chip, GE Healthcare, USA) using amine coupling.

Subsequently, in order to compare the FcRn-binding affinity of NTIG of the present invention and the FcRn-binding affinity of IgG4 Fc, the present inventors analyzed, through surface plasmon resonance (SPR), the binding affinity of, with FcRn, PG-11 prepared in Example 2-1 and dulaglutide (trade name Trulicity) which is a fusion protein in which commercial GLP-1 is linked to IgG4 Fc. As the analyzer, Biocore 8K (GE Healthcare, USA) was used, and all reagents used in the analysis were purchased from GE Healthcare. PG-11 and Trulicity were dissolved in a running buffer solution (PBST, pH of 6.0), then dilution was sequentially performed from 1,000 nM by ½, and multi-cycle kinetic analysis was performed. The experiment was performed at a flow rate of 30 μl/min at 25° C., an association of an analyte was performed for 60 seconds, and then dissociation was performed for 60 seconds. Based on the results of the experiment, the optimal antibody concentration was selected (Trulicity: 8,000 nM and PG-11: 2,000 nM), multi-cycle kinetic analysis was performed, and the equilibrium dissociation constant ($K_D$) was measured using the Biacore Insight program (GE Healthcare, USA). At this time, the buffer solution was replaced with a PBS buffer solution having a pH of 7.4 during regeneration.

Figure 25:
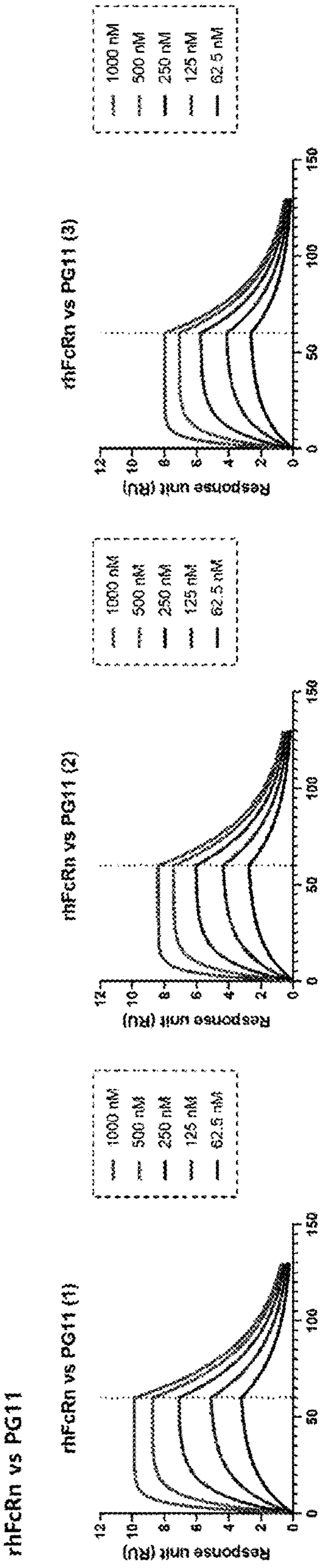
FIG. 25 is a series of graphs showing the results of analyzing binding affinity of the fusion protein (PG-11) prepared according to one exemplary embodiment of the present invention with a recombinant human neonatal Fc receptor (rhFcRn) by using surface plasmon resonance (SPR) analysis, and each of the three graphs shows the result of an independent test.
Figure 26:
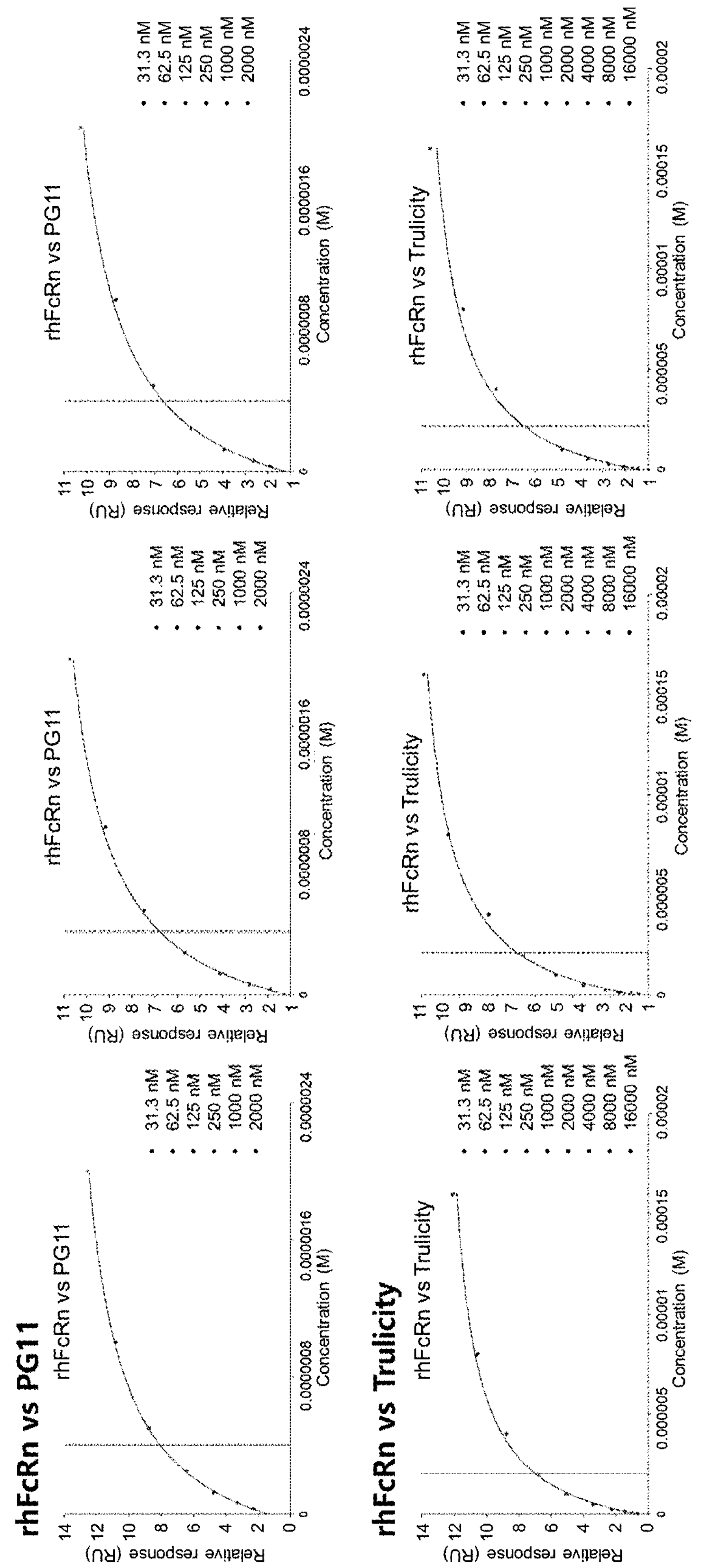
FIG. 26 is a series of graphs showing the results of analyzing the binding affinity of the fusion protein (PG-11, upper part) prepared according to one exemplary embodiment of the present invention with the recombinant human neonatal Fc receptor (rhFcRn) by using the surface plasmon resonance (SPR) analysis, compared to a case of Trulicity (lower part) using an IgG4 Fc domain, and graphs on the left, middle, and right sides show the results of three independent tests, respectively.

As shown in Table 6 and FIGS. 25 and 26, as a result of the comparative analysis of steady state affinity $K_D$, the $K_D$ value of Trulicity was 2,090 nM and the $K_D$ value of PG-II was 199 nM, and the result indicates that the affinity of PG-11 according to one exemplary embodiment of the present invention with FcRn is about 5.3 times higher than that of Trulicity. The binding affinity with FcRn is known to be related to the pharmacokinetics of the Fc fusion protein, and accordingly, the half-life in vivo of PG-11 is expected to be longer compared to Trulicity (Mackness et al., *MAbs*. 11(7): 1276-1288, 2019).

TABLE 6

Analysis results of affinity of PG-11 and Trulicity with FcRn

| Analyte | PG-11 | Trulicity |
|---|---|---|
| Steady state affinity ($K_D$) | 397 ± 19.3 nM | 2,090 ± 75.5 nM |
| CV % (Steady state affinity, $K_D$) | 4.86 | 3.61 |

In addition, in order to compare the FcRn-binding affinity of NTIG of the present invention and the FcRn-binding affinity of IgG4 Fc, the present inventors analyzed, through surface plasmon resonance (SPR), the binding affinity of, with FcRn, PG-11 and Rituximab which is a commercial recombinant chimeric anti-CD20 antibody of an IgG1 family. PG-11 and Rituximab were dissolved in a running PBST buffer solution (pH of 6.0) at various concentrations (2,000 nM to 1.96 nM for PG-11, and 4,000 nM to 3.9 nM for Rituximab), and then similar to the comparative analysis of PG-11 and Trulicity, association, dissociation, and regeneration were performed under the conditions of 60 seconds for the association, 60 seconds for the dissociation, and 30 seconds for the regeneration. During the regeneration, a PBS buffer solution having a pH of 7.4 was used.

Figure 27:
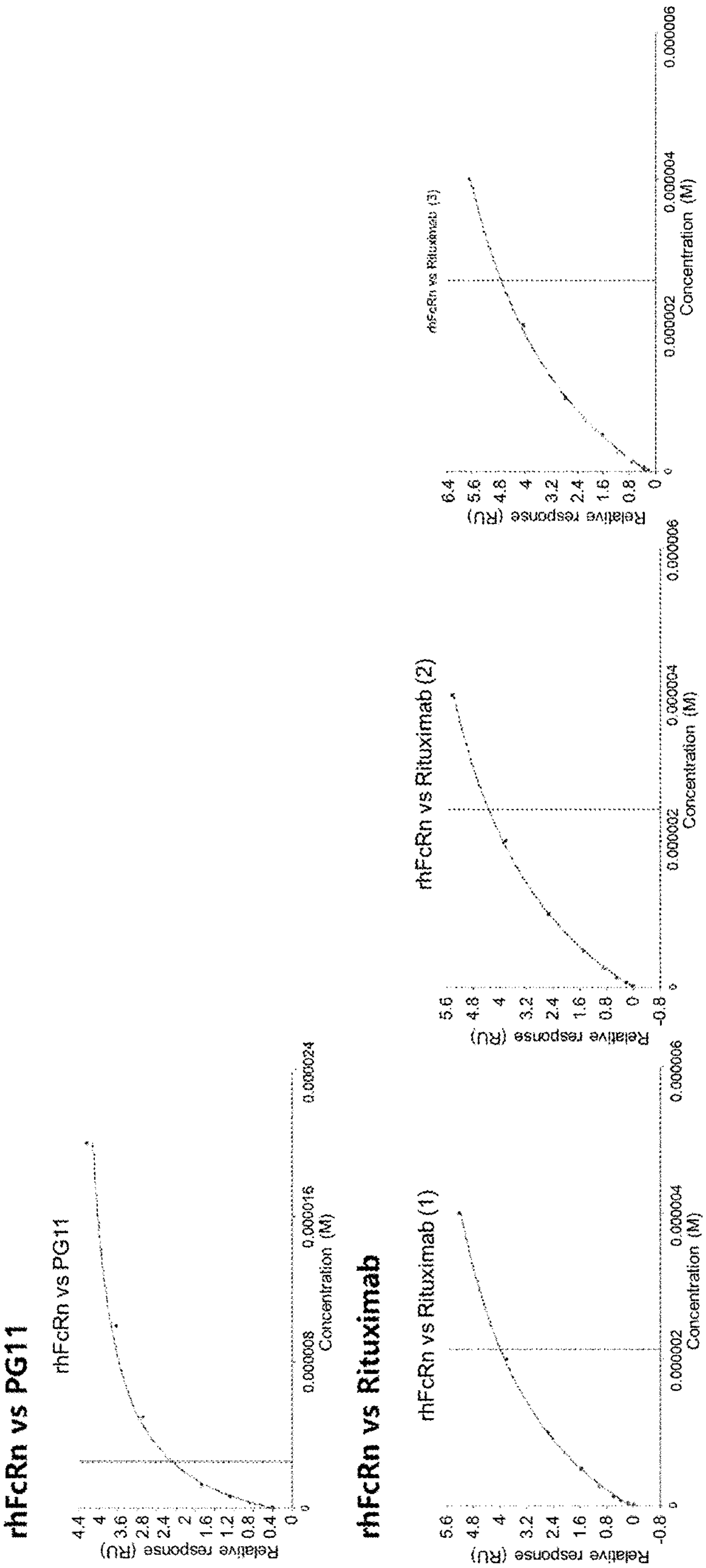
FIG. 27 is a series of graphs showing the results of analyzing the binding affinity of the fusion protein (PG-11, upper part) prepared according to one exemplary embodiment of the present invention with the recombinant human neonatal Fc receptor (rhFcRn) by using the surface plasmon resonance (SPR) analysis, compared to a case of Rituximab (lower part) which is a recombinant humanized antibody containing an IgG1 Fc domain, and graphs on the left, middle, and right sides at the lower part show the results of three independent tests, respectively.

As shown in Table 7 and FIG. 27, as a result of the comparative analysis of steady state affinity $K_D$, the $K_D$ value of Rituximab was 2,390 nM and the $K_D$ value of PG-11 was 256 nM, and the result indicates that the affinity of PG-11 according to one exemplary embodiment of the present invention with FcRn is about 9.3 times higher than that of Rituximab.

TABLE 7

Analysis results of affinity of PG-11 and Rituximab with FcRn

| Analyte | PG-11 | Rituximab |
|---|---|---|
| Steady state affinity ($K_D$) | 256 nM | 2,390 ± 242 nM |
| CV % Steady state affinity ($K_D$) | — | 10.15 |

As described above, NTIG according to one exemplary embodiment of the present invention has high affinity with FcRn compared to the Fc region of conventional IgG1 or IgG4, and thus when NTIG is administered in vivo, the half-life is expected to be significantly improved.

Subsequently, the present inventors intended to compare the affinity of the modified IgG4 Fc domain protein of SEQ ID NO: 2 with FcRn, on the basis of NTIG (SEQ ID NO: 7) according to one exemplary embodiment of the present invention.

For the comparison, instead of calculating a simple $K_D$ value, the present inventors calculated a steady state affinity ($K_D$) by associating the proteins at a pH of 6.0 and performing dissociation at a pH of 7.3 (Piche-Nicholas et al., *MAbs*. 10(1): 81-94, 2018). Specifically, for the binding affinity of anti-PD-L1-NTIG-IL-2 and anti-PD-L1-modified IgG4 Fc-IL-2 prepared in Example 3-1 with rhFcRn, SPR analysis was performed by changing the pH conditions during the association and the dissociation as described above.

Figure 28:
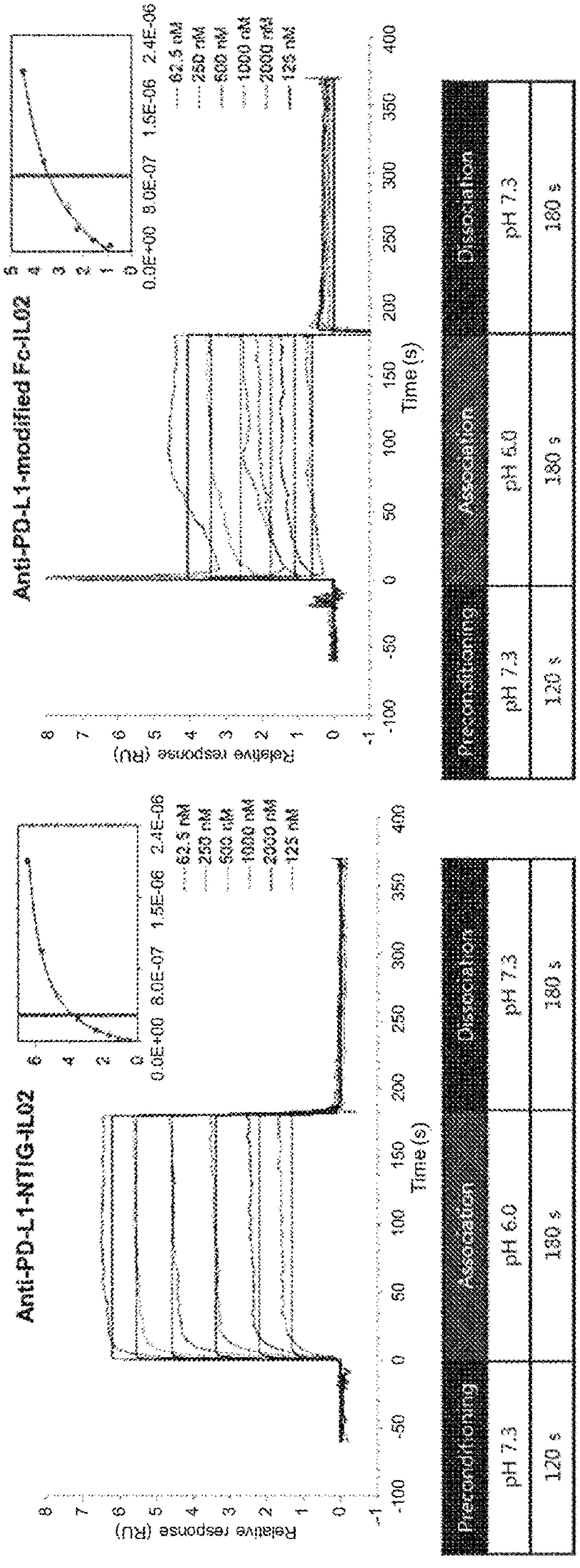
FIG. 28 is a series of graphs showing the results of comparative analysis of binding affinity of rhFcRn with each of a bispecific fusion protein (left side) in which anti-PD-L1 scFv and an IL-2 protein are respectively linked to an N-terminus and a C-terminus of an NTIG protein according to one exemplary embodiment of the present invention and a bispecific fusion protein (right side), as a control group, in which anti-PD-L1 scFv and the IL-2 protein are respectively linked to an N-terminus and a C-terminus of the modified IgG4 Fc protein of SEQ ID NO: 2, through the SPR analysis using rhFcRn as a ligand and the two substances as samples.

As a result, as shown in Table 8 and FIG. 28, it could be found that the affinity, with the FcRn, of anti-PD-L1-NTIG-IL-2 to which NTIG was applied tended to be higher than that of anti-PD-L1-modified IgG4 Fc-IL-2 using the modified IgG4 Fc. However, in the exchange process of the binding buffer solution, a large amount of protein aggregates were generated in the anti-PD-L1-modified IgG4 Fc-IL-2 protein sample, and thus there was a problem that the reliability of the results was poor. Accordingly, the same experiment was performed again by changing a test material to a ligand and FcRn to a sample.

These results suggest that the application of NTIG exhibits an effect of enhancing the half-life in vivo through enhancement of the FcRn-binding force of the produced protein as well as a superior effect on the physical properties the and stability of the protein, compared to the previously known application of the modified IgG4 Fc of SEQ ID NO: 2.

TABLE 8

Analysis results of affinity of NTIG and modified IgG4 Fc with FcRn

| Ligand | Analyte | Binding ratio | $k_a$ (1/ms) | $k_d$ (1/s) | $K_D$ (M) | Steady state affinity $K_D$ (M) | Chi$^2$ | $R_{max}$ | % bound |
|---|---|---|---|---|---|---|---|---|---|
| FcRn | Anti-PD-L1-NTIG-IL-2 | 1:1 | 1.99E+06 | 5.43E−01 | 2.73E−07 | 2.95E−07 | 6.57E−02 | 7.1 | 2.04 |
| FcRn | Anti-PD-L1-modified IgG4 Fc-IL-2 | 1:1 | 4.37E+06 | 1.98E+00 | 4.53−07 | 8.41−07 | 1.16E−01 | 5 | 12.12 |

As the buffer solution used for the analysis, the running buffer solution (1×PBST, pH of 7.3), the sample dilution buffer solution (1×PBST, pH of 6.0), the dissociation buffer solution (1×PBST, pH of 7.3), and the regeneration buffer solution (1×PBS, pH of 8.0) were used.

Figure 29:
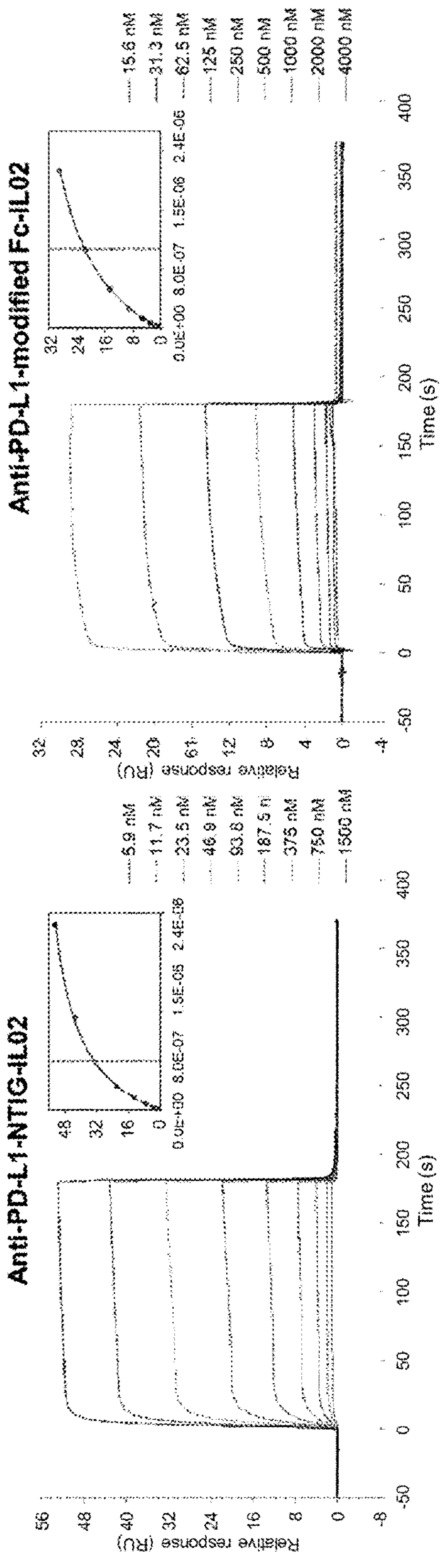
FIG. 29 is a series of graphs showing the results of comparative analysis of the binding affinity of rhFcRn with each of the bispecific fusion protein (left side) in which anti-PD-L1 scFv and the IL-2 protein are respectively linked to the N-terminus and the C-terminus of the NTIG protein according to one exemplary embodiment of the present invention and the bispecific fusion protein (right side), as a control group, in which anti-PD-L1 scFv and the IL-2 protein are respectively linked to the N-terminus and the C-terminus of the modified IgG4 Fc protein of SEQ ID NO: 2, through the SPR analysis using the two substances as ligands and rhFcRn as a sample in an opposite manner to FIG. 28.

As a result of analysis, as shown in Table 9 and FIG. 29, it was found that both proteins exhibited fast binding and rapid dissociation patterns, both proteins tended to dissociate well from the binding to FcRn under neutral conditions (pH of 7.3), but under the condition of a pH of 6.0, the affinity of the anti-PD-L1-NTIG-IL-2 protein was 5.06 times higher than that of the anti-PD-L1-modified IgG4 Fc-IL-2 protein. Consequently, the anti-PD-L1-NTIG-IL-2 protein showed a tendency to rapidly bind even to a lower concentration of FcRn under the condition of a pH of 6.0, compared to the anti-PD-L1-modified IgG4 Fc-IL-2 protein. Considering that the Fc-containing protein absorbed into the cell by the endocytosis binds to FcRn under the low pH condition of the endosome, the results strongly suggest that the fusion protein containing NTIG would be more efficiently recycled by FcRn.

TABLE 9

Analysis results of affinity of NTIG and modified IgG4 Fc with FcRn (switching between ligand and analyte)

| Ligand | Analyte | Binding ratio | Steady state affinity $K_D$ (M) | Fixation level (RU) | Relative affinity |
|---|---|---|---|---|---|
| Anti-PD-L1-NTIG-IL-2 | FcRn | 1:1 | 3.91E−07 (397 nM) | 242.1 | 5.06 |
| Anti-PD-L1-modified IgG4 Fc-IL-2 | FcRn | 1:1 | 1.98E−06 (1,980 nM) | 236.5 | — |

Experimental Example 2: Analysis of Binding Affinity with Various Fcγ Receptors The Fc region of IgG1 is known to have binding affinity with FcγRI and FcγRIIIa. These Fc receptors are associated with effector functions such as ADCC and CDC, are helpful in anticancer treatment when using antibodies or Fc fusion proteins for the anticancer treatment, but have disadvantages in which side effects are caused when using API for the purpose of treating other diseases other than anti-cancer treatment.

Accordingly, the present inventors analyzed the degree of the affinity of the NTIG fusion protein according to one exemplary embodiment of the present invention with FcγRI and FcγRIIIa compared to the IgG1 antibody through bio-layer interferometry analysis (BLI).

Figure 30:
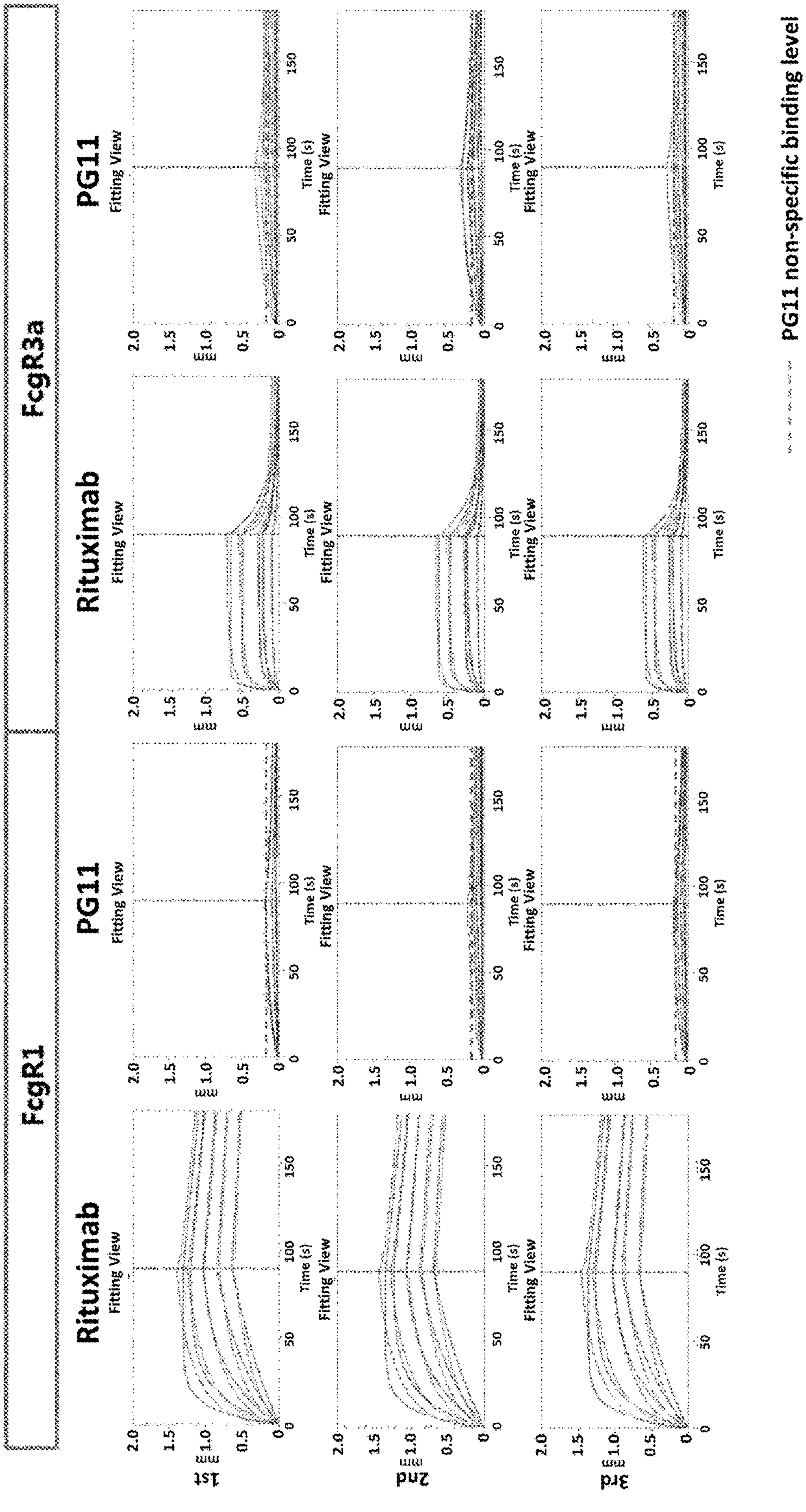
FIG. 30 is a series of graphs showing the results of analyzing, through BLI analysis, binding affinity of the fusion protein (PG-11) according to one exemplary embodiment of the present invention with Fc gamma receptor I (FcγR1, left side) or Fc gamma receptor IIIa (FcγR3a, right side), compared to a case of Rituximab which is an IgG1-based humanized antibody, and graphs at the upper, middle, and lower parts show the results of three independent tests, respectively.

As a result, as shown in FIG. 30, it was found that Rituximab, which is an IgG1-based antibody, specifically bound to FcγRI and FcγRIIIa, whereas PG-11, which is the NTIG-containing fusion protein according to one exemplary embodiment of the present invention, did not specifically bind to these antibody receptors.

Furthermore, the present inventors performed comparative analysis of the binding affinity of Rituximab and PG-11 according to one exemplary embodiment of the present invention with FcγRIIa, FcγRIIb, and FcγRIIIb.

Figure 31:
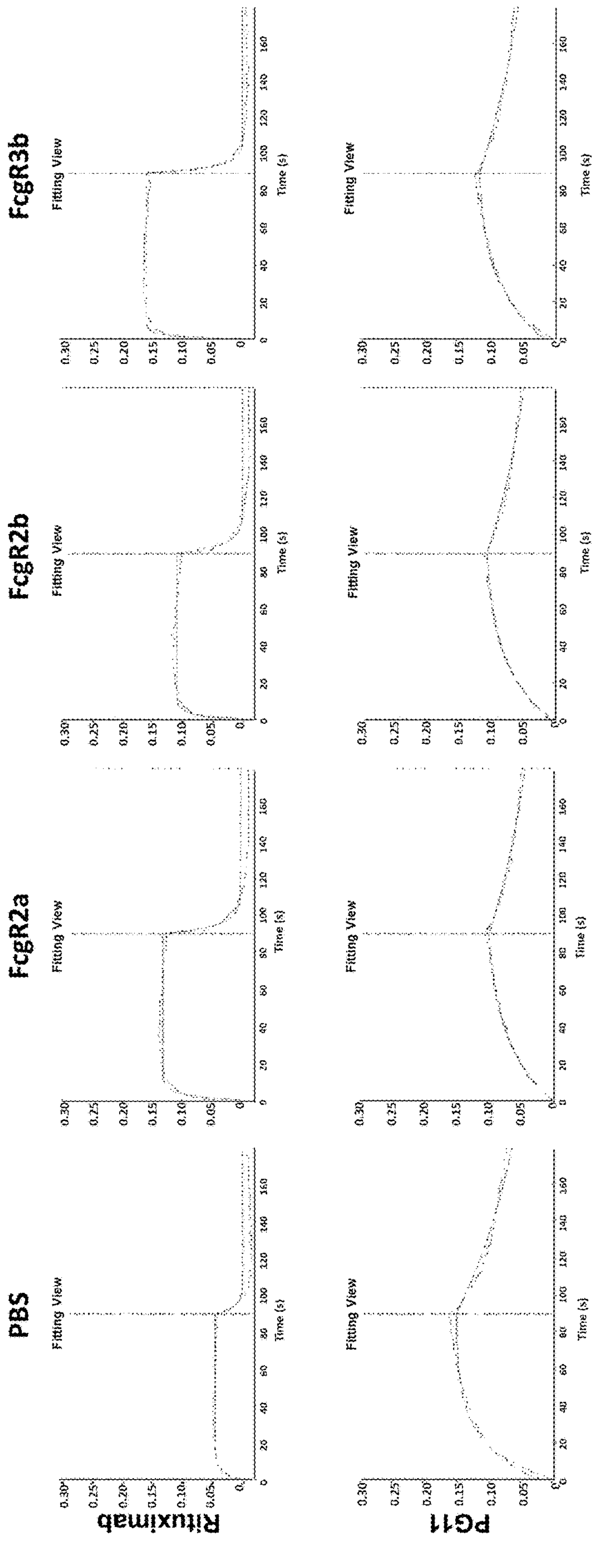
FIG. 31 is a series of graphs showing the results of analyzing, through the BLI analysis, binding affinity of the fusion protein (PG-11) according to one exemplary embodiment of the present invention with other various Fc gamma receptors (FcγRIIa, FcγRIIb, and FcγRIIIb), compared to a case of Rituximab which is an IgG1-based humanized antibody, and PBS was used as a control group.

As a result, as shown in FIG. 31, it was found that Rituximab specifically bound to the three Fc receptors. Meanwhile, PG-11 according to one exemplary embodiment of the present invention showed weak binding, but considering the shape of the sensogram, the binding is considered to be non-specific binding.

Experimental Example 3: Analysis of Binding to Complement C1a

The antibody Fc region may induce complement-dependent cytotoxicity (CDC) by binding to the complement C1q, and thus may cause a serious problem in the clinical application of the Fc fusion protein for treating general diseases other than cancer treatment. Therefore, the degree of the binding affinity of the NTIG-containing fusion protein according to one exemplary embodiment of the present invention with the complement C1q was analyzed compared to Rituximab, which is an IgG1-based antibody.

For the comparison, specifically, PG-11 and Rituximab were each diluted with a coating buffer solution (0.1 M $Na_2HPO_4$, pH of 9.6) so that each concentration was 2 μg/ml. Subsequently, 100 μl of each diluted sample was loaded into each well and reacted overnight at 4° C. Next, washing was performed three times by adding 300 μl of a washing buffer solution to the plate each time, 200 μl of a blocking buffer solution (2% BSA/PBS) was added to each well and reacted at room temperature for 2 hours. 300 μl of the washing buffer solution was added to the plate, then washing was repeatedly performed three times, an anti-C1q antibody was diluted with an assay buffer solution to 10, 3, 1, 0.3, and 0.1 μg/ml by ⅓, and mixed (duplication) in an amount of 50 μl in each well, and then the resultant was reacted at room temperature for 2 hours. Then, the washing buffer solution was mixed in the plate by 300 μl each time and washing was repeatedly performed eight times. A C1q-HRP conjugate was diluted 400-fold, and 50 μl of the resultant was added to each well and reacted at room temperature for 1 hour. The washing buffer solution was added to the plate by 300 μl each time, washing was repeatedly performed eight times, 50 μl of TMB as a substrate was mixed, and the resultant was reacted at room temperature. When the color development reaction appeared in blue, 50 μl of a stop solution was added to each well to stop the reaction, and then optical density was measured using a microplate reader set at 450 nm.

Figure 32:
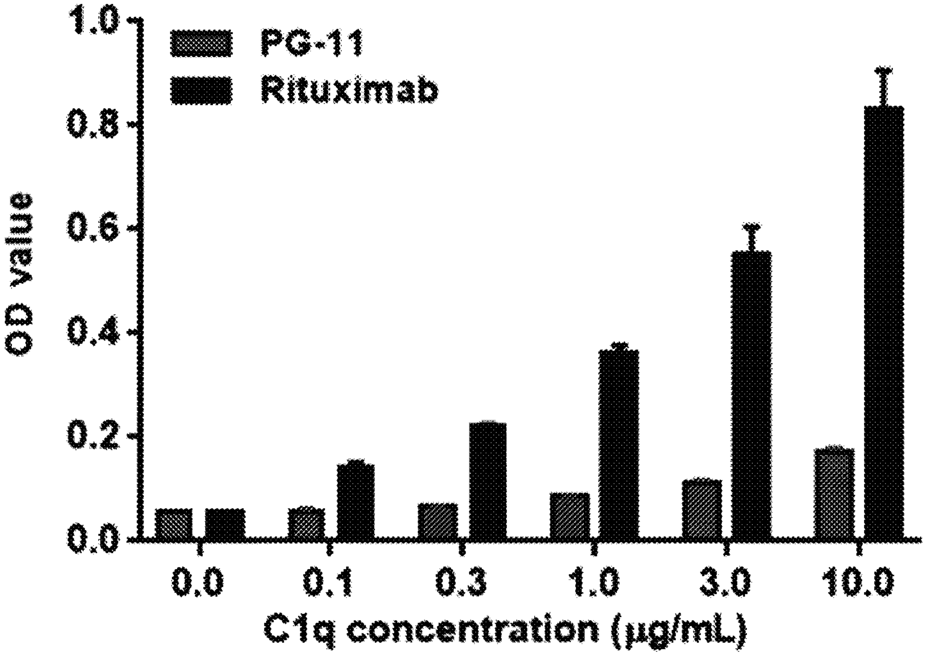
FIG. 32 is a graph showing the results of analyzing binding affinity of the fusion protein (PG-11) according to one exemplary embodiment of the present invention with a complement C1q compared to a case of Rituximab.

As a result of the analysis, as shown in FIG. 32, it was found that Rituximab bound to C1q in a concentration-dependent manner, whereas PG-11 according to one exemplary embodiment of the present invention did not bind to C1q.

Therefore, it was confirmed that NTIG according to one exemplary embodiment of the present invention is a safe protein carrier capable of minimizing side effects due to the Fc region such as ADCC or CDC while improving the half-life of API.

Experimental Example 4: Analysis of GLP-2 Activity

Whether the GLP-2 activity was properly exhibited with respect to a number of fusion proteins containing GLP-2 among Examples described above was investigated by cAMP Hunter™ eXpress GPCR analysis (Table 10).

TABLE 10

Constructs used for GLP-2 activity analysis

| Example | Code | Construct structure |
|---|---|---|
| 2-2 | PG-22 | GLP-2G-NTIG |
| 5-1 | MG12-4 | GLP-1E/GLP-2G-NTIG (GLP-1 w/glycan linker) |
| 5-2 | MG12-5 | GLP-1E/GLP-2G-NTIG (GLP-1 w/non-glycan linker) |
| 6-3 | PG-210-5 | GLP-2V(3 point)-NTIG-IL-10Vm (Patent linker) |
| 6-4 | PG-210-6 | GLP-2V(3 point)-NTIG-IL-10Vm (GS + IgG1 hinge linker) |

Figure 33:
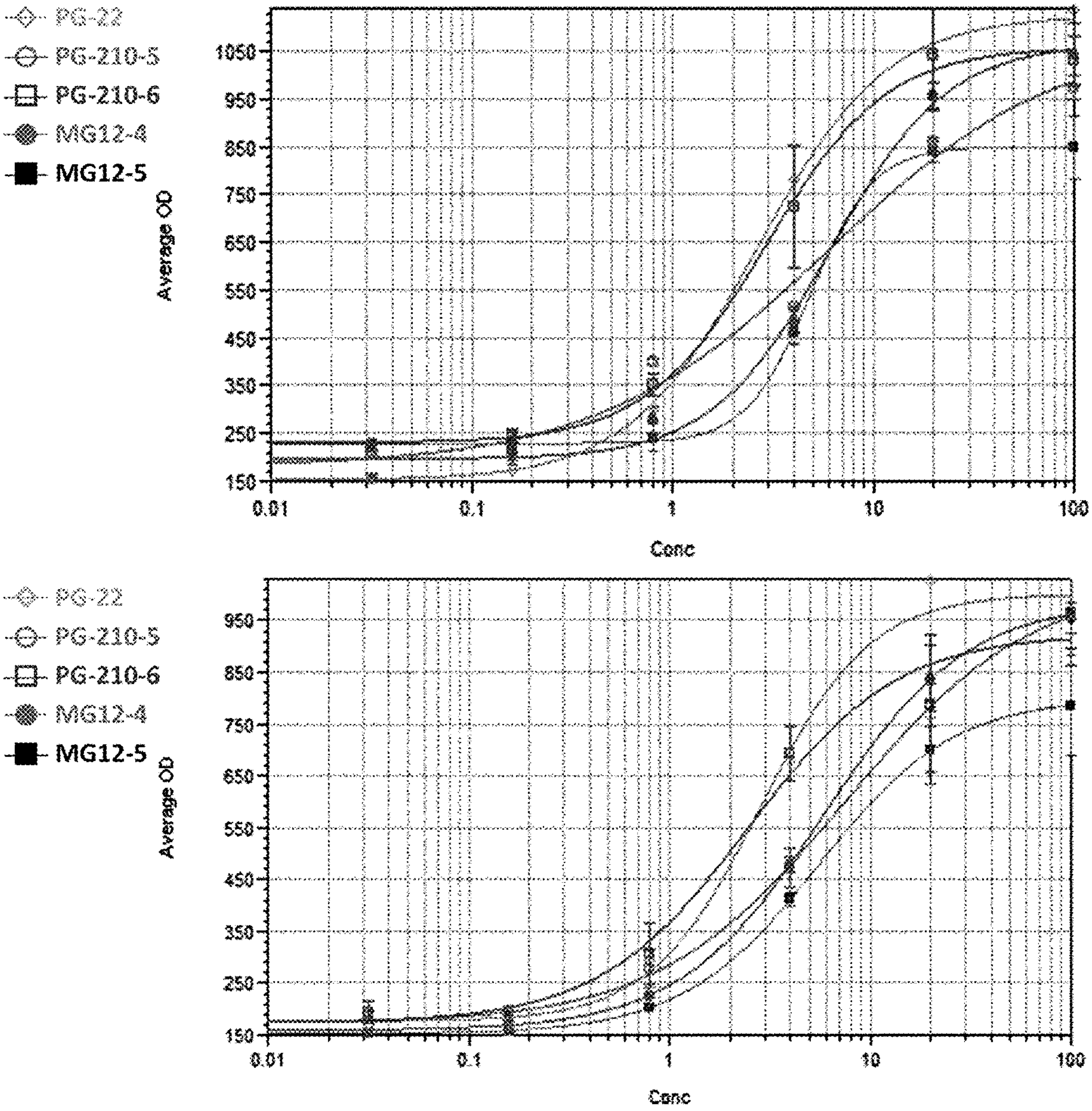
FIG. 33 is a series of graphs showing the results of comparative analysis of GLP-2 activities of fusion proteins (PG-22, PG-201-5, PG-201-6, MG12-4, and MG12-5), which contain a GLP-2 analog, according to various exemplary embodiments of the present invention, and the two graphs at the upper and lower parts show the results of two independent tests, respectively.

As a result of analysis, as shown in FIG. 33 and Table 11, it was found that PG-210-6 among the fusion proteins prepared according to one Example of the present invention exhibited a GLP-2 activity almost similar to those of PG-22 as Comparative Example, and PG-210-5 of another Example of the present invention exhibited an activity which was about half an activity of PG-210-6. MG12-4 and MG12-5, which are heterodimers, were also found to exhibit a GLP-2 activity which was only about half the GLP-2 activity of PG-22, but since MG12-4 and MG12-5 each contain one GLP-2 molecule, in case of MG12-4 and MG12-5, a 50% decrease in activity compared to PG-22 in which two GLP-2 molecules bound could be predicted. PG-210-5 was a protein to which the linker peptide used in the prior patent literature (U.S. Pat. No. 7,812,121B2) was applied, and it was found that the activity of PG-210-6 using the mixed linker peptide of $(G_4S)_3$+IgG1 hinge used in the present invention was excellent.

TABLE 11

Results of GLP-2 activity analysis

| Example | 2-2 | 5-1 | 5-2 | 6-3 | 6-4 |
|---|---|---|---|---|---|
| First $EC_{50}$ (nM) | 2.84 | 5.81 | 5.49 | 7.44 | 2.46 |
| First relative activity (%) | 100% | 48.8% | 51.7% | 38.1% | 115% |
| Second $EC_{50}$ (nM) | 2.65 | 6.08 | 4.85 | 5.95 | 2.93 |
| Second relative activity (%) | 100% | 43.5% | 54.6% | 44.5% | 90% |
| Average activity (%) | 100% | 46.15% | 53.15% | 41% | 102.5% |

Experimental Example 5: Analysis of Immunosuppressive Activity of IL-10Vm Fusion Protein 5-1: Analysis of Affinity with IL-10 Receptor The present inventors analyzed the affinity of the fusion proteins of Examples 2-3 and 2-4 with the IL-10 receptor 1 (IL-10R1) through the bio-layer interferometry analysis (BLI).

For the analysis, the present inventors attached an IL-10R His-tag protein to a 96-well plate using a Dip and Read™ Amine Reactive 2nd Generation (AR2G) Reagent Kit (forteBio, Cat No. 18-5092). Specifically, 200 µl of D. W. was dispensed into a 96-well plate, and an amine biosensor included in the kit was inserted to perform hydration for 10 minutes. Subsequently, after 200 µl of D. W. was additionally dispensed into a new 96-well plate, EDC and NHS were mixed at 1:1 in an amount of 1/20 of the required sample amount and then diluted with D. W., and 200 µl of the resultant was dispensed into the 96-well plates. Next, the IL-10R His-tag protein was diluted to 10 µg/ml in a 10 mM acetate solution having a pH of 5.0, and then 200 µl of the resultant was added to the 96-well plates. After 200 µl of 1 M ethanolamine was added to the 96-well plates, the biosensor plate and the sample plate were placed in an Octet®-K2 instrument and measured. After the measurement was completed, 200 µl of a 1× kinetics buffer solution was added to the sample plate, and then a baseline was determined. Thereafter, the prepare NTIG-IL-10 fusion protein was diluted with the 1× kinetics buffer solution to various concentrations (0, 62.5, 125, 250, 500, and 1,000 nM), 200 µl of the resultant was dispensed to the sample plate, and then bio-layer interferometry (BLI) was measured using the Octet®-K2 instrument.

TABLE 12

| Parameter | Example 2-3 | Example 2-4 |
|---|---|---|
| $K_D$ (nM) | 11.1 ± 0.9 | 29.2 ± 8.85 |
| $K_{on}$ (1/Ms) | 71100 ± 6670 | 20550 ± 2312 |
| $K_{dis}$ (1/s) | 0.0008 | 0.0006 |
| $R^2$ | 0.97 | 0.97 |

Figure 34:
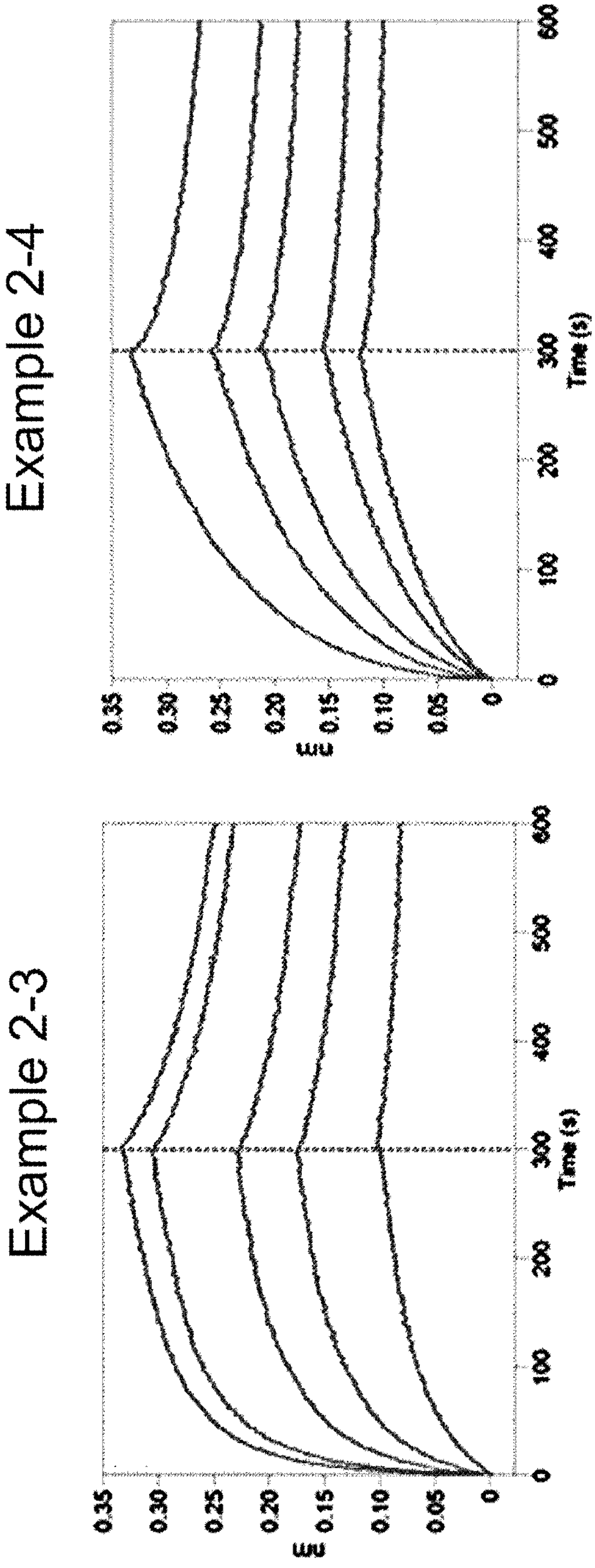
FIG. 34 is a series of graphs showing the results of checking, by the BLI analysis, the affinity with IL-10R1 according to the treatment concentrations of a dimeric IL-10 variant fusion protein (left side) of Example 2-3 and a monomeric IL-10 variant fusion protein (right side) of Example 2-4 according to the present invention.

As a result, as shown in FIG. 34 and Table 12, the $K_D$ value of the fusion protein (NTIG-IL-10Vm) according to Example 2-4 of the present invention was 29.2 nM, which was about three times the $K_D$ value (11.1 nM) of the dimeric IL-10 fusion protein of Example 2-3. The result may be interpreted that the monomeric IL-10 variant fusion protein has a lower affinity with the receptor than the dimeric IL-10 protein, but it could be predicted that the affinity could be reduced due to the monomer formation.

5-2: Analysis of Immunosuppressive Activity of IL-10Vm Fusion Protein

The present inventors analyzed immunosuppressive activities in vitro of various fusion proteins (PG-088m, PG-110, PG-410, and PG-210-6) containing the monomeric IL-10 variant protein (IL-10Vm) according to one exemplary embodiment of the present invention.

For the analysis, specifically, after a supernatant was removed from a T75 flask including a macrophage Raw264.7 in culture, washing was performed once with PBS, then 3 ml of TrypLE™ Select Enzyme was added, and the resultant was reacted at 37° C. for 3 to 5 minutes. Thereafter, 10 ml of a fresh medium was added to the T75 flask, and a cell suspension from the bottom of the flask was transferred to a 50 ml conical tube and then centrifuged at 1,500 rpm for 5 minutes. Next, the supernatant was removed and the tube was gently tapped to release cells. Then, 5 ml of a fresh medium were mixed and the cells were counted. The cell concentration was adjusted to be $1\times10^5$ cells/ml, and 100 µl of the resultant was dispensed into a 96-well flat-bottom plate.

Thereafter, PG-088m prepared in Example 2-4, PG-110 prepared in Example 3-3, PG-410 prepared in Example 4-3, and PG-210-6 prepared in Example 6-4 were sequentially diluted to various concentrations (0 to 1,000 nM for PG-210-6 and PG-410, and 0 to 1,507 nM for PG-110 and PG-088m), and then 50 µl of each protein was dispensed into the 96-well plate into which the macrophage Raw264.7 was dispensed. After 20 minutes, a lipopolysaccharide (LPS) was treated in an increment of 50 µl so that the final concentration was 400 ng/ml, and the resultant was cultured at 36° C. for 16 hours. The next day, the supernatant was collected, and then TNF-α ELISA (Biolegend, USA) analysis was performed according to the protocol of the manufacturer.

Figure 35A:
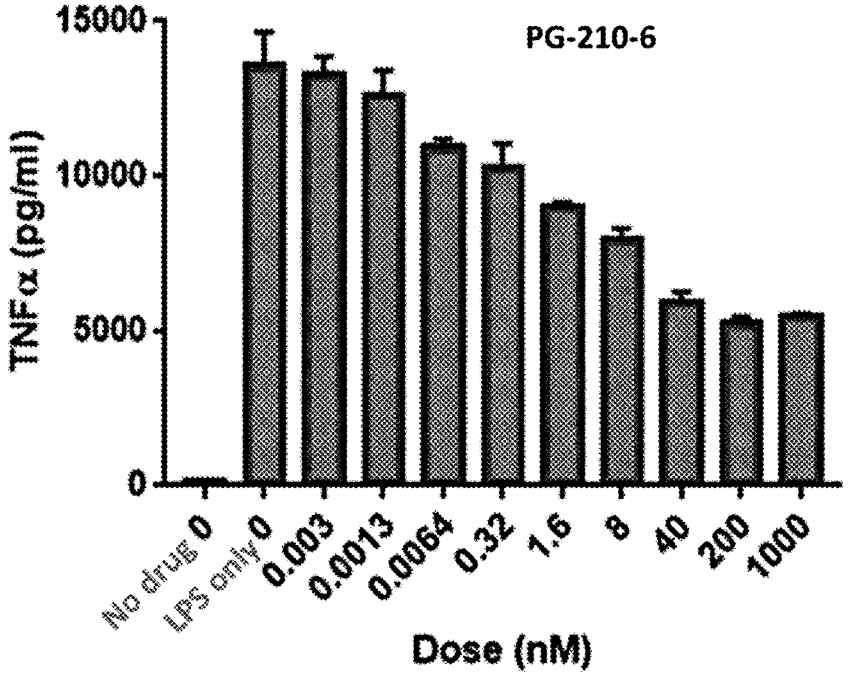
FIG. 35*a* is a graph showing the results of quantitatively analyzing, by ELISA analysis, the release level of TNF-α in a macrophage according to the concentration of the fusion protein PG-210-6 according to one exemplary embodiment of the present invention.
Figure 35B:
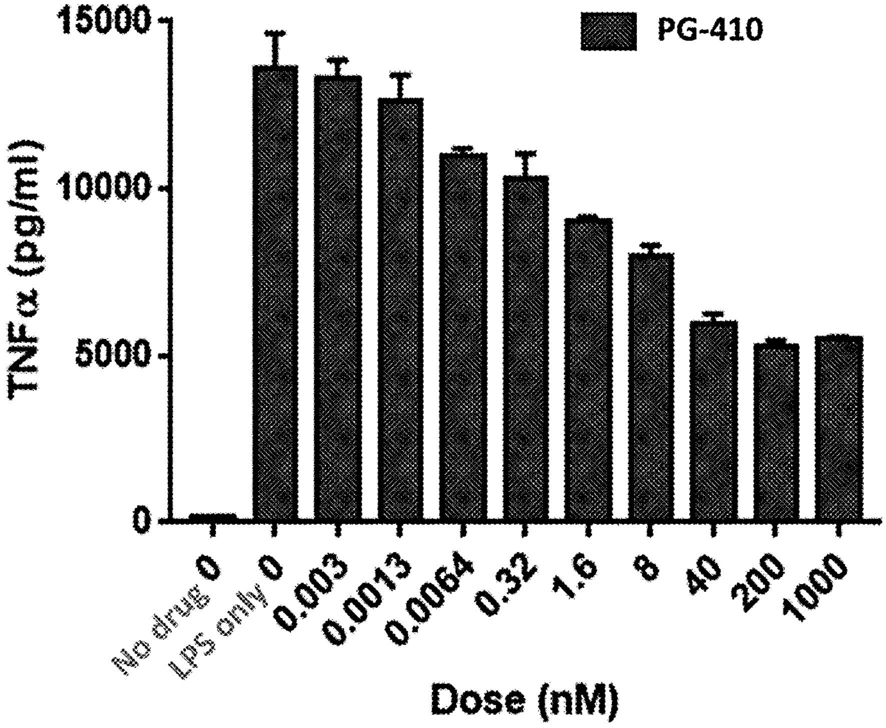
FIG. 35*b* is a graph showing the results of quantitatively analyzing, by the ELISA analysis, the release level of TNF-α in the macrophage according to the treatment concentration of the fusion protein PG-410 according to one exemplary embodiment of the present invention.
Figure 35C:
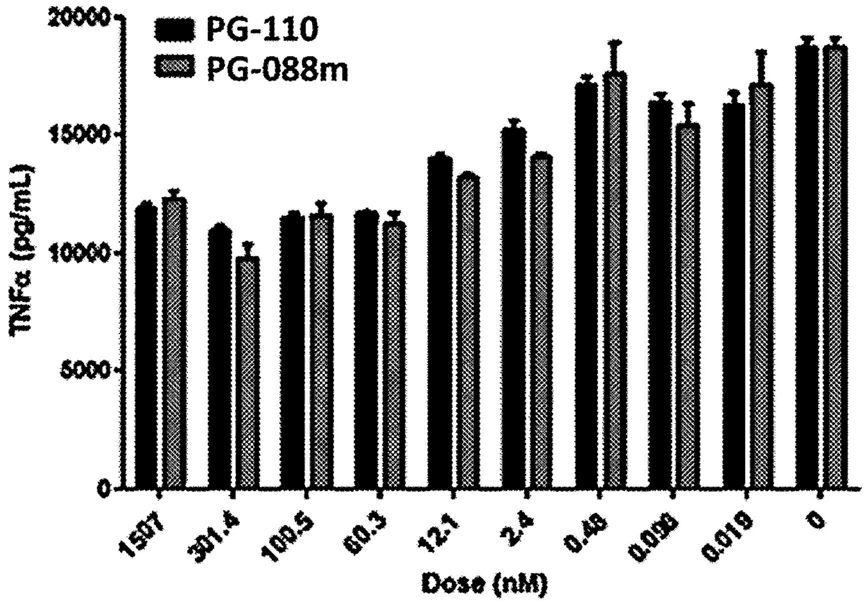
FIG. 35*c* is a graph showing the results of quantitatively analyzing, by the ELISA analysis, the release level of TNF-α in the macrophage according to the treatment concentrations of the fusion proteins PG-110 and PG-088m according to one exemplary embodiment of the present invention.

As a result, as shown in FIGS. 35*a* to 35*c*, all fusion proteins containing IL-10Vm according to one exemplary embodiment of the present invention were found to inhibit TNF-α secretion in macrophages in a concentration-dependent manner. The significant difference according to the type of fusion protein was not found. The results indicate that the monomeric IL-10 variant protein (IL-10Vm) according to one exemplary embodiment of the present invention properly works even when the monomeric IL-10 variant protein is linked to the C-terminus of the NTIG protein.

5-3: Analysis of IgE-Binding Ability

The present inventors analyzed the affinity of the fusion protein (FcεRIα-NTIG-IL-10Vm) prepared in Example 3-3 with mouse IgE and human IgE through the bio-layer interferometry analysis (BLI).

For the analysis, the present inventors first attached the FcεRIα-NTIG protein having no IL-10Vm as a control group and the fusion protein prepared in Example 3-3 to a 96-well plate using a Dip and Read™ Amine Reactive 2nd Generation (AR2G) Reagent Kit (forteBio, Cat No. 18-5092). Specifically, 200 µl of D. W. was dispensed into a 96-well plate, and then an amine biosensor included in the kit was inserted to perform hydration for 10 minutes. Subsequently, after 200 µl of D. W. was additionally dispensed, EDC and NHS were mixed at 1:1 in an amount of 1/20 of the required sample amount and then diluted with D. W., and 200 μl of the resultant was dispensed into the 96-well plate. Next, the FcεRIα-modified IgG4 Fc protein and the FcεRIα-NTIG-IL-10Vm fusion protein were diluted to 10 μg/ml in a 10 mM acetate solution having a pH of 5.0, and then 200 μl of the resultant was added to the 96-well plate. After 200 μl of 1 M ethanolamine was added to the 96-well plate, the biosensor plate and the sample plate were placed in an Octet®-K2 instrument and measured. After the measurement was completed, 200 μl of a 1× kinetics buffer solution was added to the sample plate, and then a baseline was determined. Thereafter, anti-DNP mouse IgE (Sigma) was diluted with the 1× kinetics buffer solution to various concentrations (50 pM to 3.125 nM), 200 μl of the resultant was dispensed to the sample plate, and then bio-layer interferometry (BLI) was measured using the Octet®-K2 instrument.

marrow-derived mast cells obtained from a mouse were washed with an HBSS buffer solution, adjusted so that the concentration was $5\times10^5$ cells/60 μl, and then dispensed into 96-well plate. 20 μl of the sample reacted with IgE and the test drug was added to previously prepared mast cells, and the resultant was cultured for 25 minutes in an incubator with conditions of 37° C. and 5% $CO_2$. Next, 20 μl of DNP BSA (500 ng/ml) was added, the resultant was cultured again for 30 minutes in the incubator with conditions of 37° C. and 5% $CO_2$ and centrifuged at 4° C. at a rate of 1,500 rpm, and 30 μl of a supernatant was separated. 30 μl of the separated supernatant and 30 μl of a substrate (4-nitrophenyl N-acetyl-p-glucosaminide, 5.84 mM) were mixed and cultured for 25 minutes in the incubator with conditions of 37° C. and 5% $CO_2$. 400 μl of a 0.1 M sodium carbonate buffer solution (pH of 10) was mixed and the reaction was terminated.

TABLE 13

| | FcεRIα-modified IgG4 Fc | | | PG-110 (FcεRIα-NTIG-IL-10Vm) | | |
|---|---|---|---|---|---|---|
| Parameter | First | Second | Third | First | Second | Third |
| Average $K_D$ (nM) | 0.364 | 0.478 (Average: 0.594) | 0.940 | 0.224 | 0.282 (Average: 0.284) | 0.346 |
| Average $K_{on}$ (1/Ms) | $1.23\times10^5$ | $1.49\times10^5$ | $1.66\times10^5$ | $1.52\times10^5$ | $1.44\times10^5$ | $1.39\times10^5$ |
| Average $K_{dis}$ (1/s) | $4.48\times10^{-5}$ | $7.10\times10^{-5}$ | $1.56\times10^{-4}$ | $3.40\times10^{-5}$ | $4.06\times10^{-5}$ | $4.82\times10^{-5}$ |
| Average $R^2$ | 0.996 | 0.999 | 0.997 | 0.999 | 0.999 | 0.999 |

Figure 36A:
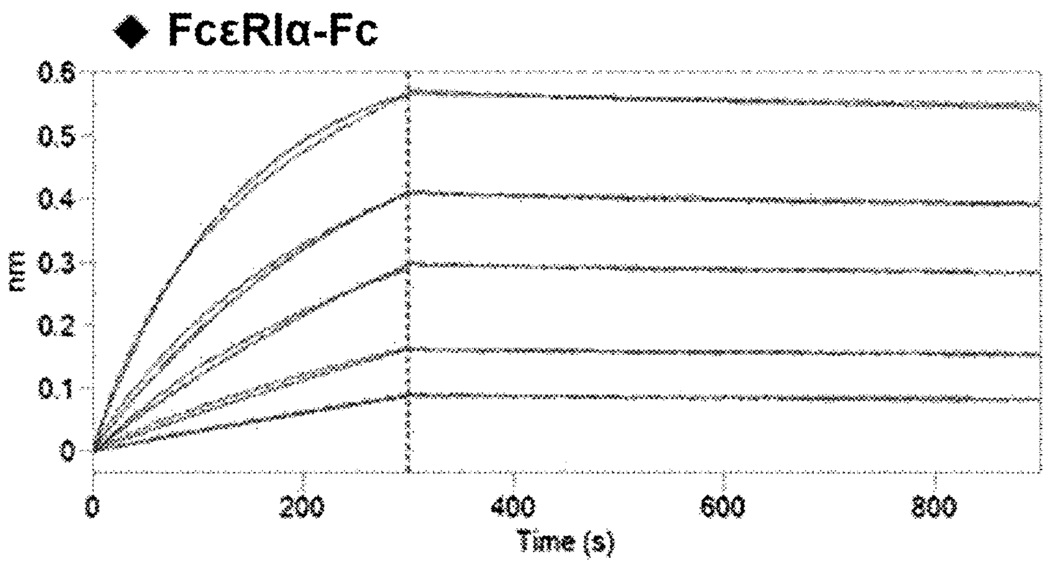
FIG. 36*a* is a series of graphs showing the results of analyzing, by the BLI analysis, affinity of FcεRIα-modified IgG4 Fc (upper part) as Comparative Example and a fusion protein FcεRIα-NTIG-IL-10Vm (lower part) of Example 3-3 of the present invention with mouse IgE.
Figure 36A:
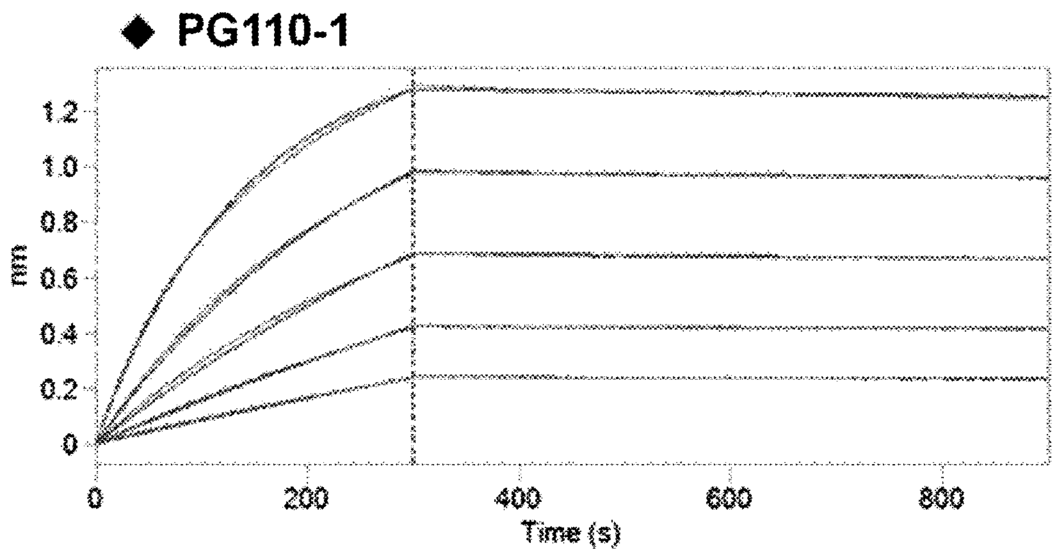

As a result, as shown in FIG. 36*a* and Table 13, the $K_D$ value of the fusion protein (FcεRIα-NTIG-IL-10Vm) according to one exemplary embodiment of the present invention was 0.284 nM, which was slightly lower than that of FcεRIα-modified IgG4 F as a control group. However, the difference is not a significant difference, and thus it was found that the binding ability to IgE was not decreased by the addition of the monomeric IL-10 protein.

In addition to the above results, in order to measure the binding degree of human FcεRIα and human IgE used in the present invention, the present inventors analyzed the affinity of the fusion protein (PG-110) of Example 3-3 with human IgE using the abovementioned BLI method.

TABLE 14

| | PG-110 (FcεRIα-NTIG-IL-10Vm) |
|---|---|
| Average $K_D$ (nM) | 0.346 |
| Average $K_{on}$ (1/Ms) | $2.19\times10^5$ |
| Average $K_{dis}$ (1/s) | $7.59\times10^{-5}$ |
| Average $R^2$ | 0.9955 |

Figure 36B:
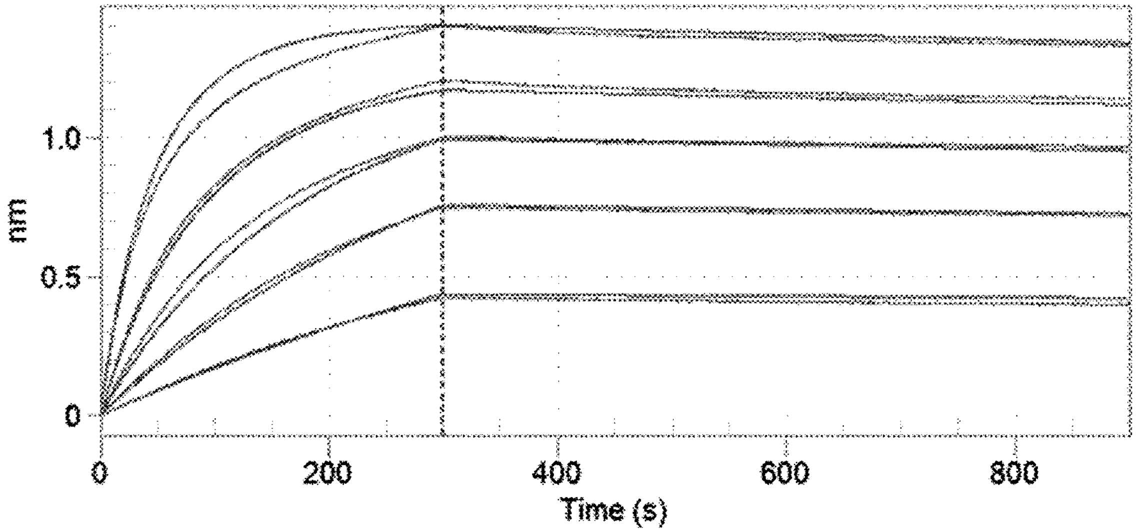
FIG. 36*b* is a graph showing the results of analyzing, by the BLI analysis, affinity of the fusion protein FcεRIα-NTIG-IL-10Vm of Example 3-3 of the present invention with human IgE.

As a result, as shown in FIG. 36*b* and Table 14, the affinity of the fusion protein according to one exemplary embodiment of the present invention with human IgE was also similar to the affinity with mouse IgE.

5-4: Analysis of Inhibitory Activity Against IgE

Subsequently, the present inventors investigated whether the fusion protein (FcεRIα-NTIG-IL-10Vm) prepared in Example 3-3 exhibited inhibitory activity against IgE by an in vitro experiment.

For the investigation, specifically, FcεRIα-modified IgG4 Fc as a control group and the fusion protein (PG-110) of Example 3-3 as an experimental material were sequentially diluted to various concentrations to prepare samples, and the samples were mixed with 1 μl/ml of anti-DNP mouse IgE and reacted at room temperature for 30 minutes. Then, nated. Thereafter, the relative amounts of β-hexominidase secreted from the mast cells were compared by measuring the absorbance at 405 nm, and an effect of suppressing mast cells according to the concentration of each drug was checked. The analysis was independently conducted three times and an average thereof was obtained.

Figure 37:
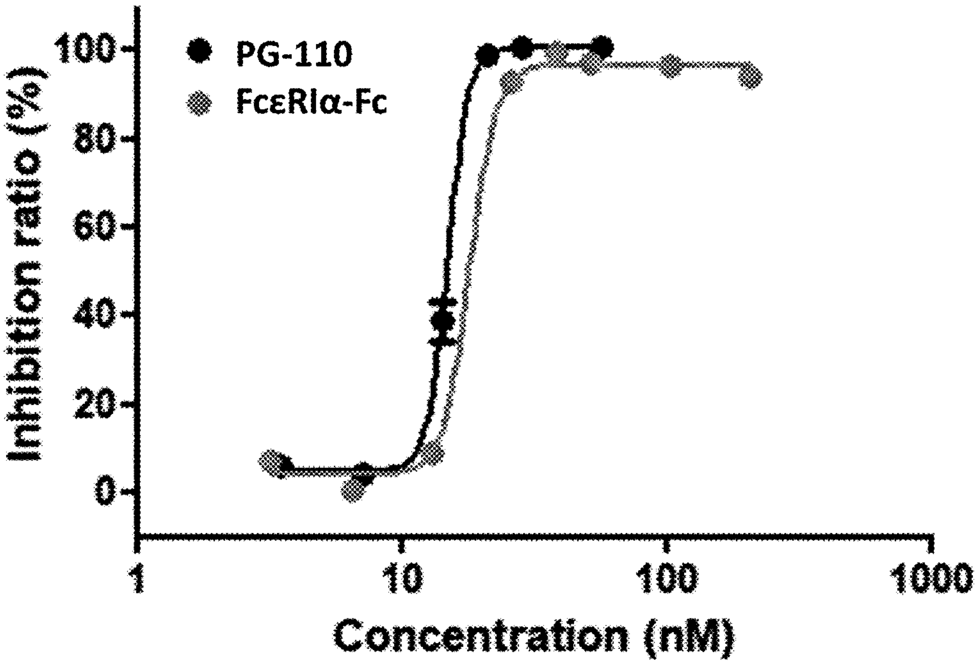
FIG. 37 is a graph showing the results of analyzing, through β-hexosaminidase release analysis, IgE inhibitory activity of the fusion protein PG-110 according to one exemplary embodiment of the present invention and FcεRIα-modified IgG4 Fc according to one exemplary embodiment of the present invention.

As a result, as shown in FIG. 37 and Table 15, the fusion protein PG-110 according to one exemplary embodiment of the present invention inhibited the activity of IgE in a concentration-dependent manner, the degree thereof was similar to that of FcεRIα-modified IgG4 Fc as the control group, but $IC_{50}$ of the fusion protein PG-110 according to one exemplary embodiment of the present invention was slightly lower than that of the FcεRIα-modified IgG4 Fc.

TABLE 15

| | $IC_{50}$ (nM) | | | |
|---|---|---|---|---|
| Test material | First test | Second test | Third test | Fourth test |
| FcεRIα-modified IgG4 Fc | 19.58 | 17.88 | 22.31 | 19.92 |
| PG-110 | 21.64 | 14.78 | 14.42 | 16.947 |

Experimental Example 6: Analysis of Binding to CD40L

The present inventors investigated the binding affinity of PG-400 and PG-410 respectively prepared in Examples 4-2 and 4-3 of the present invention with human CD40L through the BLI analysis.

For the investigation, specifically, 200 μl of distilled water was dispensed onto a 96-well black flat-bottom plate, a biosensor tray was placed on the hydrated black plate, and then an amine biosensor was inserted to perform hydration for 10 minutes. Then, 200 μl of distilled water was dispensed onto a new 96-well black sample plate, EDC and NHS were mixed at 1:1 in an amount of 1/20 of the required amount and then diluted with distilled water, and the 200 μl of the resultant was dispensed into the 96-well black sample plate. Next, human CD40L (Peptrotech, Korea) was diluted to 5 μg/ml in a 10 mM acetate solution (pH of 6.0), and then 200 μl of the resultant was added to the 96-well black sample plate. 200 μl of 1 M ethanolamine was added to the plate, the biosensor plate and the sample plate were placed in an Octet®-K2 instrument, and the degree of binding of CD40L was measured on the amine biosensor. After the measurement was completed, the 96-well black sample plate was taken out from the measuring instrument, 200 μl of a 1× kinetics buffer solution was mixed, and a baseline was set. PG-410 and PG-400, which are analytes, were sequentially diluted with the 1× kinetics buffer solution so that the concentrations were 200 to 12.5 nM, and then 200 μl of the resultant was dispensed into the 96-well black sample plate. The sample plate was placed again in the Octet®-K2 instrument, and then the degree of binding to CD40L was measured by the BLI analysis.

TABLE 16

| Analyte | PG-400 | PG-410 |
|---|---|---|
| $K_D$ (nM) | 0.36 nM | <1E−12 |
| $K_{on}$ (1/Ms) | 8.47E+05 | 1.96E+05 |
| $K_{dis}$ (1/s) | 3.11E−04 | <1E−07 |

Figure 38:
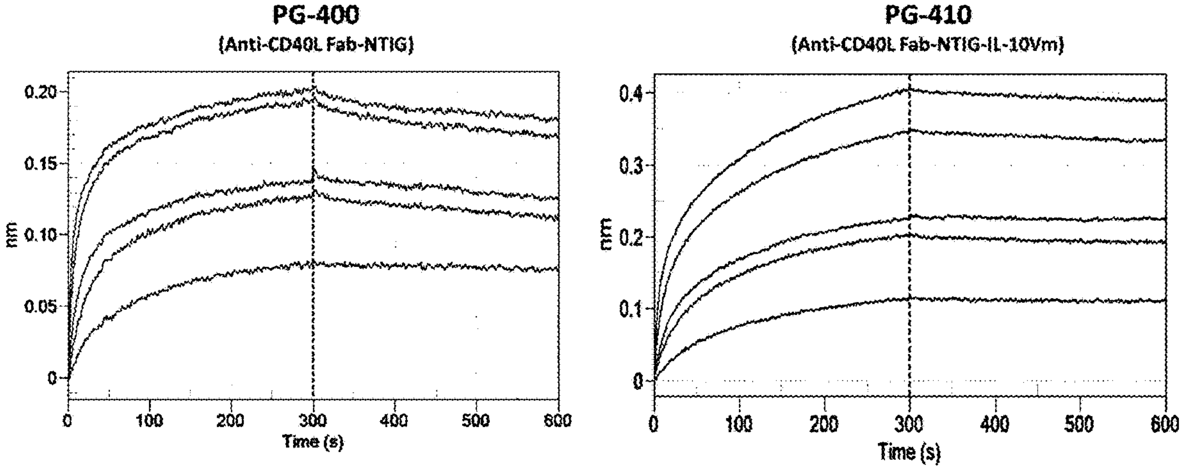
FIG. 38 is a graph showing the results of analyzing, by the BLI analysis, binding affinity of the fusion proteins PG-400 (left side) and PG-410 (right side) according to one exemplary embodiment of the present invention with CD40L.

As a result, as shown in FIG. 38 and Table 16, the fusion protein (PG-410) according to one exemplary embodiment of the present invention had a $K_{on}$ value for CD40L which is 4.3 times lower than that of the PG-400, but had a $K_D$ value of fM or less (<1E-12), which indicates a very high binding affinity, and consequently, it was confirmed that the PG-400 and PG-410 proteins can bind to human CD40L well. Here, it was found that PG-410, which is the fusion protein (anti-CD40L-NTIG-IL-10Vm) according to one exemplary embodiment of the present invention, bound to CD40L with a very high binding affinity.

Experimental Example 7: Pharmacokinetic Analysis of PG-110

The present inventors checked the pharmacokinetic profile (PK) by comparing the half-life, the area under the curve (AUC), the highest concentration in the blood ($C_{max}$), and the like of the bispecific fusion protein (PG-110), which was prepared above, according to Example 3-3.

Specifically, the fusion protein (PG-110) to be tested was administered to three male Sprague Dawley (SD) rats per group by subcutaneous (SC), intravenous (IV), intraperitoneal (IP), and intramuscular (IM) routes at a dose of 1 mg/kg. Blood was obtained prior to injection and after 0.5, 1, 5, 10, 24, 48, 72, 120, 168, 240, and 336 hours after injection, and then stored at room temperature for 30 minutes to cause aggregation. Aggregated blood was centrifuged at 3,000 rpm for 10 minutes, and then a serum of each sample was obtained and stored in a cryogenic freezer. The concentrations of the fusion proteins according to one exemplary embodiment of the present invention in sera were analyzed using an IgG-Fc Quantitation set (Bethyl, Cat #E80-104, Lot #E80-104-30), which can specifically detect Fc among the administered proteins.

Figure 39:
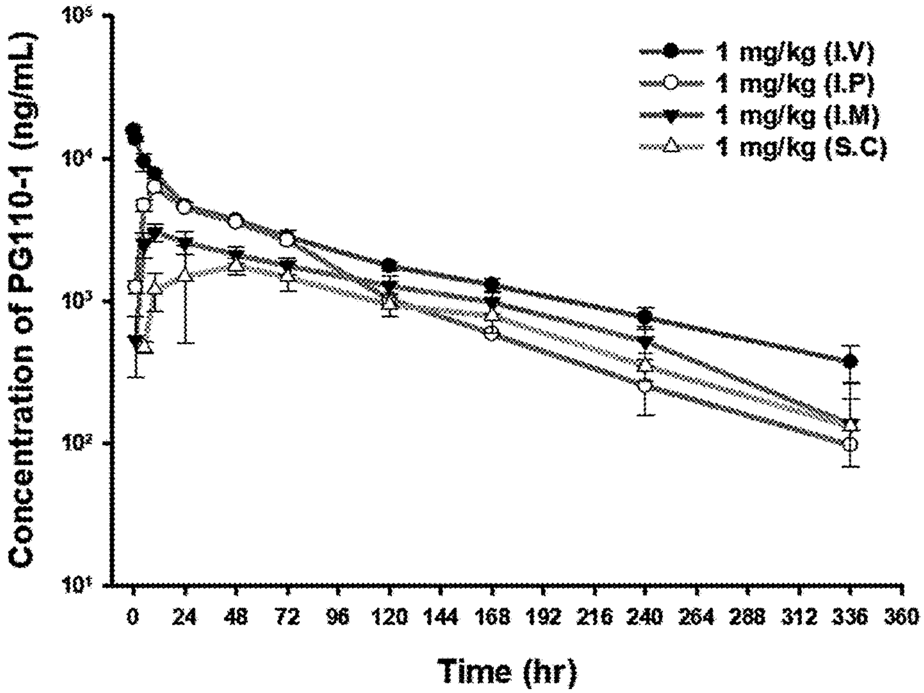
FIG. 39 is a graph showing the results of analyzing pharmacokinetic profiles according to various administration routes (SC, IV, IP, and IM) of the fusion protein PG-110 according to one exemplary embodiment of the present invention.

As a result, as shown in FIG. 39, it was found that the physiologically active protein to which NTIG was fused can be maintained in the body for a long time regardless of the administration route.

The present invention has been described with reference to the abovementioned Examples and Experimental Examples, but the description is merely exemplary, and those skilled in the art could understand that various modifications and other equivalent embodiments can be made therefrom. Therefore, the real technical protection scope of the present invention shall be determined by the technical spirit of the appended claims.

INDUSTRIAL AVAILABILITY

The NTIG protein according to one exemplary embodiment of the present invention is a fusion partner of various biologically active proteins, and increases the therapeutic effect of the biologically active protein by effectively increasing the half-life of the biologically active protein as well as enables safer drug delivery by minimizing effector functions such as ADCC and CDC, which are disadvantages of the Fc fusion protein. Therefore, the NTIG protein according to one exemplary embodiment of the present invention can be effectively used in the preparation of protein medicines.

What is claimed is:

1. An immunoglobulin Fc domain variant protein comprising the amino acid sequence selected from the group consisting of SEQ ID NOs: 5 to 9.

2. A fusion protein, wherein at least one biologically active protein is linked to an N-terminus and/or a C-terminus of the immunoglobulin Fc domain variant protein of claim 1.

3. The fusion protein of claim 2, wherein the biologically active protein is linked to the N-terminus or the C-terminus of the immunoglobulin Fc domain variant protein through a linker peptide or a hinge region of an antibody.

4. The fusion protein of claim 2, wherein the biologically active protein is a cytokine, an enzyme, a blood coagulation factor, an extracellular domain of a membrane receptor, a growth factor, a peptide hormone, or an antibody mimetic.

5. A polynucleotide which encodes the immunoglobulin Fc domain variant protein of claim 1 or the fusion protein of claim 2.

6. A recombinant vector comprising the polynucleotide of claim 5.

7. A homodimer comprising the fusion protein of claim 2.

8. A heterodimer comprising the fusion protein of claim 2.

9. The heterodimer of claim 8, wherein the immunoglobulin Fc domain variant protein has a knobs-into-holes structure.

10. A composition comprising, as an active ingredient, at least one selected from the group consisting of the fusion protein of claim 2, the homodimer of claim 7, and the heterodimer of claim 8.

11. A method for prolonging the half-life in vivo of a biologically active protein, the method comprising a step for administering, to a subject, a fusion protein obtained by fusing the biologically active protein to the immunoglobulin Fc domain variant protein of claim 1, or a homodimer or a heterodimer which contains the fusion protein, wherein the immunoglobulin Fc domain variant protein prolongs the half-life in vivo of the biologically active protein compared to the Fc region of conventional IgG1 or IgG4.

* * * * *